(12) United States Patent
Sibbett et al.

(10) Patent No.: US 9,439,837 B2
(45) Date of Patent: Sep. 13, 2016

(54) COMPOSITION

(75) Inventors: Wilson Sibbett, Fife (GB); Christian Thomas Alcuin Brown, Fife (GB); Animesh Jha, Yorkshire (GB); Steven John Milne, Yorkshire (GB); Colin Robinson, Yorkshire (GB); Mandeep Singh Duggal, Yorkshire (GB); Kyriacos Jack Toumba, Yorkshire (GB)

(73) Assignees: University of Leeds (GB); The University Court of the University of St. Andrews (GB)

( * ) Notice: Subject to any disclaimer, the term of this patent is extended or adjusted under 35 U.S.C. 154(b) by 0 days.

(21) Appl. No.: 13/878,399

(22) PCT Filed: Oct. 10, 2011

(86) PCT No.: PCT/GB2011/051938
§ 371 (c)(1),
(2), (4) Date: Jun. 13, 2013

(87) PCT Pub. No.: WO2012/046082
PCT Pub. Date: Apr. 12, 2012

(65) Prior Publication Data
US 2013/0260341 A1   Oct. 3, 2013

(30) Foreign Application Priority Data

Oct. 8, 2010 (GB) .................................. 1016970.4

(51) Int. Cl.
*A61K 6/033* (2006.01)
*A61K 6/00* (2006.01)
*A61K 6/04* (2006.01)
(Continued)

(52) U.S. Cl.
CPC ........... *A61K 6/0017* (2013.01); *A61B 5/0088* (2013.01); *A61C 19/003* (2013.01); *A61K 6/0008* (2013.01); *A61K 6/033* (2013.01); *A61K 6/043* (2013.01); *A61K 6/0085* (2013.01)

(58) Field of Classification Search
None
See application file for complete search history.

(56) References Cited

U.S. PATENT DOCUMENTS 3,873,327 A * 3/1975 Duff ..................... A61K 6/0067
106/35
4,048,300 A * 9/1977 Tomlinson ............... A61K 8/21
424/49
(Continued)

FOREIGN PATENT DOCUMENTS

CN        1 723 915 A    1/2006
JP      2008 069048 A    3/2008
WO  WO 2009076491 A2 *  6/2009

OTHER PUBLICATIONS

W Wang, D Shi, J Lian, Y Guo, L Wang, RC EWing. "Luminescent hydroxylapatite nanoparticles by surface functionalization." Applied Physics Letters, vol. 89, 2006, pp. 183106-1 to 183106-3.*
(Continued)

*Primary Examiner* — Isaac Shomer
(74) *Attorney, Agent, or Firm* — Brinks Gilson & Lione; Ryan L. Marshall

(57) ABSTRACT

The present invention relates to a photosensitive composition comprising synthetic nanocrystalline hydroxyapatite or a synthetic precursor thereof doped with a rare earth ion, the use of the composition in restorative or cosmetic dentistry, a process for preparing the composition and a method of generating an image of an exposed dentinal surface of a tooth.

9 Claims, 42 Drawing Sheets

Figure 1:
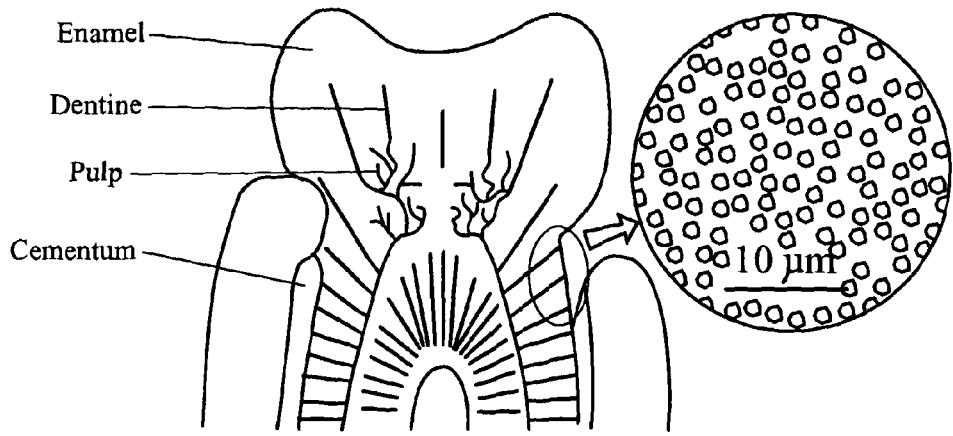

(51) Int. Cl.
*A61B 5/00* (2006.01)
*A61C 13/15* (2006.01)

(56) References Cited

U.S. PATENT DOCUMENTS

| | | | |
|---|---|---|---|
| 4,083,955 A | | 4/1978 | Grabenstetter et al. |
| RE33,221 E | * | 5/1990 | Brown ............... A61K 8/24 106/35 |
| 5,545,254 A | * | 8/1996 | Chow et al. ............... 106/35 |
| 5,605,677 A | * | 2/1997 | Schumann ........... A61K 8/21 424/49 |
| 5,752,833 A | | 5/1998 | Yamamoto |
| 5,833,959 A | * | 11/1998 | Atsumi ............... A61K 8/24 106/35 |
| 2002/0164291 A1 | | 11/2002 | Cozean et al. |
| 2009/0042161 A1 | * | 2/2009 | Jodaikin ............ A61C 19/063 433/80 |
| 2010/0040668 A1 | | 2/2010 | Riman et al. |

OTHER PUBLICATIONS

C Yang, p. Yang, W Wang, S Gai, J Wang, M Zhang, J Lin. "Synthesis and characterization of Eu-doped hydroxyapatite through a microwave assisted microemulsion process." Solid State Sciences, vol. 11, 2009, pp. 1923-1928.*

Chun Yang, et al., "Synthesis and characterization of Eu-doped hydroxyapatite through a microwave assisted microemulsion process," *Solid State Sciences*, 11:1923-1928 (Jul. 22, 2009).

Database WPI, Week 200643, Thomson Scientific, London, GB; AN 2006-415705 XP002680458 (Jan. 25, 2006).

Database WPI, Week 200827, Thomson Scientific, London, GB; AN 2008-D75925 XP002680457 (Mar. 27, 2008).

International Search Report for corresponding International Application No. PCT/GB2011/051938, mailed Aug. 7, 2012 (4 pages).

Lin, Y., et al., "Preparation, Characterization and Antibacterial Property of Cerium Substituted Hydroxyapatite Nanoparticles," *Journal of Rare Earths, International Academic Publishers*, Beigjing, CN, 25(4):452-456 (Aug. 1, 2007).

Written Opinion for corresponding International Application No. PCT/GB2011/051938, mailed Aug. 7, 2012 (7 pages).

* cited by examiner

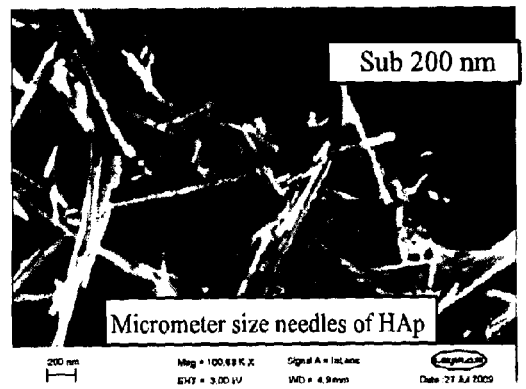
Figure 11a
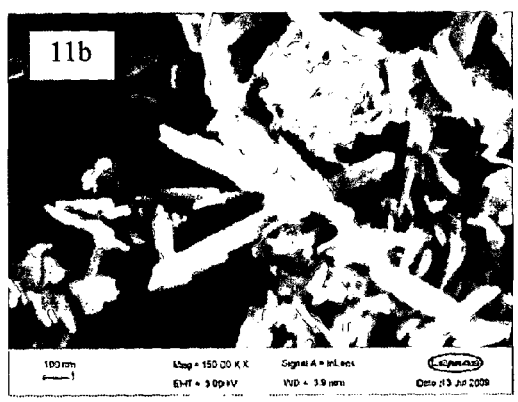 
Figure 11b                Figure 11c
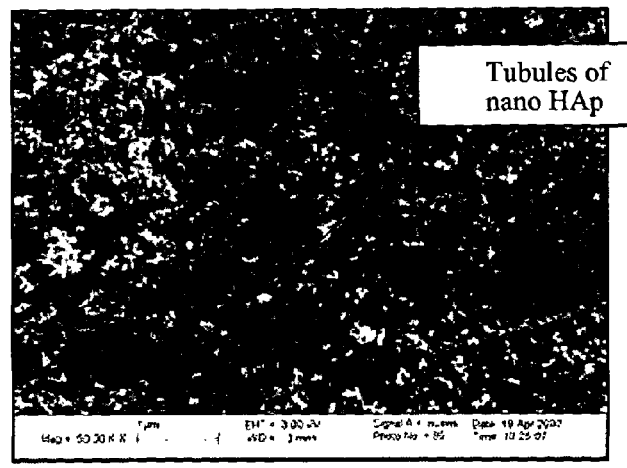
Figure 12

(a) (b)

(a) (b)

COMPOSITION

REFERENCE TO EARLIER FILED APPLICATIONS

This application is a 371 national phase of PCT/GB2011/051938, filed Oct. 10, 2011, and claims the benefit of Great Britain Application No. 1016970.4, filed Oct. 8, 2010, the disclosures of which are incorporated, in their entirety, by this reference.

The present invention relates to a photosensitive composition (eg a photosensitive CaP mineral composition) comprising nanocrystalline hydroxyapatite doped with a rare earth ion, the use of the composition in restorative or cosmetic dentistry, a process for preparing the composition and a method of generating an image of an exposed dentinal surface of a tooth.

A dental condition is acutely painful. A fear of invasive techniques which frequently involve a drill discourages many people from attending a dental surgery. As a result, severe long-term dental problems commonly arise. For example, the only long-term solution for the treatment and recurrence of dental caries is mechanical drilling and filling. This is highly invasive and painful due to damage to hard and soft tissue. On recurrence, the cavities tend to grow deeper and more inaccessible and are often enlarged by the mechanical tools used in the clinical procedure. The size of the cavities therefore varies significantly from sub-hundred micrometer in the early-stage (compared with 1-5 µm pores in the structures of skeletal minerals) to mm in the advanced stage.

FIG. 1 is a schematic illustration of the structure of a tooth. Dentine has fluid-filled cylindrical microchannels (tubules) which extend from the pulp to the outer edge of the tooth and terminate at the dentine-enamel or dentine-cementum junction. The number density and average diameter of tubules at the pulpal region are generally taken to be about 45000 per $mm^2$ and about 2.5 µm respectively and at the dentine-enamel junction to be about 20000 per $mm^2$ and about 0.9 µm respectively. The dentine may be classified as intertubular or peritubular. Intertubular dentine consists of a fibrous network of collagen with deposited nanocrystalline mineral (predominantly hydroxyapatite). The peritubular lining is a more highly mineralized tissue with a greater proportion of hydroxyapatite and fewer collagen fibres.

Discomfort from dentine hypersensitivity is experienced commonly by large sections of the population. The inset in FIG. 1 shows a portion of an SEM micrograph of an etched section of dentine showing exposed open dentine tubules (circled) simulating extreme hypersensitivity. According to a generally accepted hydrodynamic theory, thermal, chemical and tactile stimuli generate fluid movement within tubules which can trigger the nerve endings in the pulp and result in pain. This is exacerbated as a result of exposure of the tubule openings to the oral environment owing to gum recession or loss of enamel. Poor dental hygiene, overvigorous brushing, attrition and acid erosion are contributory factors. Gum recession gives very rapid and extensive exposure of the tubule openings as the thin cementum layer on the surface of dentine is easily abraded.

To some extent, sensitivity is reduced by the formation of a natural barrier in the form of a smear layer of 1-5 µm thickness on the surface of the dentine. The smear layer contains naturally generated debris but does not sufficiently alleviate the condition as it is readily removed by (for example) brushing or chewing.

Conventional treatment of dentine hypersensitivity is frequent and repeated and is based on tubule occlusion and/or a nerve desensitisation agent (see Martens et al: *Effect of anti-sensitive toothpastes on opened dentinal tubules and on two dentin-bonded resins*: Clinical Preventive Dentistry. 1991 13:23-28; and Ling T Y Y et al: *An investigation of potential desensitizing agents in the dentine disc model: a scanning electron microscopy study*. Journal of Oral Rehabilitation. (1997) 24 (3) 191-203). Specially formulated toothpastes containing micron-sized inorganic particles are available to encourage the formation of a smear layer to physically block the tubules. They may also contain chemical agents to desensitise the neural response (see Miller S et al: *Evaluation of a new dentrifice for the treatment of sensitive teeth*. Journal of Clinical Dentistry (1994) 5:71-79). However the conventional treatments are generally short term and the condition is frequently recurrent.

Another approach is the application of potassium oxalate by clinicians. By reacting with calcium ions present in the oral environment, potassium oxalate forms insoluble calcium oxalate by demineralisation-remineralisation processes which involve dissolution-precipitation of hydroxyapatite $[Ca_{10}(PO_4)_6(OH)_2]$. The solid product helps to seal the tubules and suppress fluid-movement (see Pashley et al: *The use of oxalate to reduce dentin permeability under adhesive restorations*. American Journal of dentistry 14, 89-94, 2001). Similarly the application of casein phosphopeptides which carry amorphous calcium phosphate aids the natural re-mineralisation process via the precipitation of released calcium and phosphate ions. In this case, the active ingredient can readily be administered via chewing gum (see Bannon M et al: *Amorphous Calcium Phosphate Casein Phosphopeptide (ACP-CCP) as a dentinal hypersensitivity treatment agent*. Journal of Dental Research 74 (3) 754-754 MAR 1995). Slow-release fluoride beads bonded onto teeth to prevent cavities have a beneficial effect in reducing sensitivity (see M E J Curzon and K J Toumba: *In vitro and in vivo assessment of a glass slow fluoride releasing device*: a pilot study. Brit. Dent. J., 196, 543-546, 2004).

A Nd-YAG crystal based pulsed laser operating at 1064 nm has been widely used in surgical dentistry for paediatric and adult oral health. The laser is used frequently for cutting enamel and poses the risk of collateral damage because at the laser wavelength none of the overtones or the combination IR absorption bands for the enamel mineral exists (ie phosphate, $CO_3^{2-}$, $OH^-$ or $H_2O$). The lack of sufficient absorption of 1064 nm laser radiation creates a thermal load situation in which a significant part of laser energy is utilised in heating the surrounding healthy tissue. In current surgical practice, avoidance of damage arising from such heating is prevented by rinsing with water and air cooling.

Neither calcium ions nor phosphate ions have strong absorption bands in the near infrared region (800-2000 nm). However phosphate ions have harmonics in the region of 2500 nm which overlap the fundamental $OH^-$ ion band in the region 2700 to 3000 nm. Since the harmonics are much weaker (typically 1000 to 100000 times weaker) in intensity than the fundamental mode, the energy absorption via the harmonics are also proportionally less. This means that when pulsed laser energy is used for a surgical procedure involving a hydroxyapatite mineral, the risk of collateral damage to surrounding healthy tissues and heat generation above the tolerable limit of 41° C. is a major concern.

The present invention is based on the recognition that a composition containing synthetic nanocrystalline hydroxyapatite $(Ca_{10}(PO_4)_6(OH)_2)$ doped with rare earth ions is sufficiently stable in vivo to physically occlude dentinal tubules whilst being photosensitive to laser irradiation.

Thus viewed from a first aspect the present invention provides a photosensitive composition comprising (preferably consisting essentially of):
synthetic nanocrystalline hydroxyapatite or a synthetic precursor thereof doped with a rare earth ion; and
one or more synthetic minerals of formula $CaHPO_4.xH_2O$ (wherein x is 0, 1 or 2).

Synthetic nanocrystalline hydroxyapatite (nHAp) or a synthetic precursor thereof doped with a rare earth ion in accordance with the photosensitive composition of the invention is advantageously capable of forming a permanent barrier to a dentinal tubule to combat hypersensitivity, dental caries and tooth decay. The photosensitive composition exhibits a high surface area and reactivity whilst its agglomerates may still be sufficiently small to occlude or enter a micron-scale tubule and act as a scaffold for tissue growth and promote mineralisation to effectively and permanently seal the tubule. The rare earth ion serves to provide an excellent non-radiative pathway for radiation quenching. In seeking to combat dental conditions or to facilitate restorative or cosmetic dentistry, this advantageously permits the exploitation of short-pulsed laser irradiation to promote densification (eg sintering). Furthermore rare earth ions have a strong tendency to form rare earth phosphates at the expense of OH and $HPO_4$ ions which means that the formation of carbonate via bicarbonate at OH sites (which is the cause of weak bonding in the lattice) is reduced. Thus the photosensitive composition when sintered exhibits an enhanced ability to withstand acid attack in the oral environment.

The rare earth ion typically substitutes calcium in the crystal lattice of the nanocrystalline hydroxyapatite or synthetic precursor thereof.

The synthetic precursor of synthetic nanocrystalline hydroxyapatite may be octacalcium phosphate.

Preferably the photosensitive composition comprises synthetic nanocrystalline hydroxyapatite doped with a rare earth ion.

Preferably the (or each) of the one or more $CaHPO_4.xH_2O$ minerals is doped with the rare earth ion. The rare earth ion typically substitutes calcium in the crystal lattice of the one or more $CaHPO_4.xH_2O$ minerals.

Preferably x is 0 or 2.

Preferably the one or more $CaHPO_4.xH_2O$ minerals is monetite and/or brushite.

Preferably the rare earth ion and calcium have a substantially similar ionic radius (eg an ionic radius within ±15%). This advantageously facilitates the substitution of calcium by the rare earth ion in nanocrystalline hydroxyapatite and optionally in the one or more $CaHPO_4.xH_2O$ minerals.

In a preferred embodiment, the nanocrystalline hydroxyapatite or synthetic precursor thereof is fluoride ion-substituted. In a preferred embodiment, the (or each) of the one or more $CaHPO_4.xH_2O$ minerals is fluoride ion-substituted. Substitution of hydroxide ions by fluoride ions in nanocrystalline hydroxyapatite or synthetic precursor thereof advantageously redresses the charge imbalance caused by the substitution of calcium (2+) with rare earth ion (3+).

In a preferred embodiment, the nanocrystalline hydroxyapatite or synthetic precursor thereof is further doped with aluminium ions. In a preferred embodiment, the (or each) of the one or more $CaHPO_4.xH_2O$ minerals is doped with aluminium ions. Aluminium ions have a strong tendency to form aluminium phosphate at the expense of OH and $HPO_4$ ions which means that the formation of carbonate via bicarbonate at OH sites (which is the cause of weak bonding in the lattice) is reduced. Thus this photosensitive composition when sintered exhibits an enhanced ability to withstand acid attack in the oral environment.

In a preferred embodiment, the nanocrystalline hydroxyapatite or synthetic precursor thereof is fluoride ion-substituted and doped with aluminium ions.

In the nanocrystalline hydroxyapatite doped with a rare earth ion, the rare earth ion is present in an amount relative to nanocrystalline hydroxyapatite in excess of 100 ppm. Preferably the rare earth ion is present in an amount relative to nanocrystalline hydroxyapatite in the range 100 to 50000 ppm.

Preferably the rare earth ion exhibits absorption bands which substantially match or overlap one or more absorption bands of the synthetic nanocrystalline hydroxyapatite. Particularly preferably the rare earth ion exhibits absorption bands which substantially match or overlap one or more absorption bands of one or more of the $OH^-$ ion, $CO_3^{2-}$ ion, phosphate ion or water (eg the first harmonic of the phosphate band or the fundamental OH band).

Preferably the rare earth ion exhibits absorption bands in or overlapping the range 1400 to 1800 nm.

Preferably the rare earth ion exhibits absorption bands in or overlapping the range 2700 to 3500 nm.

Preferably the rare earth ion exhibits absorption bands in or overlapping the range 4000 to 4500 nm.

Preferably the rare earth ion exhibits absorption bands in or overlapping the range 1900 to 2100 nm.

The rare earth ion may be a lanthanide ion. The rare earth ion may be selected from one or more of the group consisting of a cerium, gadolinium, holmium, thulium, dysprosium, erbium, ytterbium and neodymium ion.

Preferably the rare earth ion is selected from one or more of the group consisting of a dysprosium, ytterbium, erbium, holmium and thulium ion. Particularly preferably the rare earth ion is an erbium, ytterbium, holmium or thulium ion. More preferably the rare earth ion is an erbium, ytterbium or thulium ion. Especially preferably the rare earth ion is an erbium ion.

The rare earth ion may be impregnated in a casein-phospholipid. This embodiment may be useful in dental surface imaging.

In a preferred embodiment, the nanocrystalline hydroxyapatite is further doped with a co-dopant. The co-dopant may usefully exhibit absorbtion or excitation at (for example) desirable wavelengths (for example visible wavelengths). The co-dopant may exhibit broad absorbtion bands which can be exploited to minimise heat dissipation during photosintering and enhance safety. The co-dopant may be a transition metal ion or rare earth ion.

The co-dopant may be an ytterbium ion. The co-dopant may be an iron ion or chromium ion.

Preferably the co-dopant is present in an amount relative to nanocrystalline hydroxyapatite of 0.01 wt % or less.

Typically the predominant phases of the photosensitive composition are the synthetic nanocrystalline hydroxyapatite doped with a rare earth ion and the one or more $CaHPO_4.xH_2O$ minerals. The photosensitive composition may be a solid solution of hydroxyapatite, brushite and monetite. Monetite may predominate. The amount of the synthetic nanocrystalline hydroxyapatite or synthetic precursor thereof doped with a rare earth ion in the photosensitive composition is typically at least 25 wt %. The amount of the one or more $CaHPO_4.xH_2O$ minerals in the photosensitive composition is typically at least 50 wt %.

The photosensitive composition may further comprise one or more secondary calcium phosphate phases. The one or more secondary calcium phosphate phases may be present in an amount of 25 wt % or less.

The photosensitive composition may further comprise one or more dopant source phases. The one or more dopant source phases may be one or more of the group consisting of calcium fluoride, stannous fluoride, aluminium chloride, aluminium phosphate and tetraethyl orthosilicate. Preferably the photosensitive composition further comprises $CaF_2$ and $AlPO_4$.

In a preferred embodiment, the nanoparticles of synthetic nanocrystalline hydroxyapatite or synthetic precursor thereof doped with a rare earth ion are protein conjugated. Protein conjugation may accelerate mineralisation.

The photosensitive composition may be nanoparticulate. The nanoparticles of synthetic nanocrystalline hydroxyapatite or synthetic precursor thereof doped with a rare earth ion (or of the photosensitive composition) may be substantially flat, substantially rod-like, platelets, needles or whiskers. Preferably the nanoparticles of synthetic nanocrystalline hydroxyapatite or synthetic precursor thereof doped with a rare earth ion (or of the photosensitive composition) are platelets.

Preferably the photosensitive composition is capable of at least partially occluding a dentinal tubule in a tooth.

Preferably the photosensitive composition is capable of at least partially occluding a dentinal tubule to a depth of at least 1 μm.

The photosensitive composition may be capable of substantially fully (eg fully) occluding a dentinal tubule in a tooth.

Preferably the photosensitive composition is capable of at least partially (eg substantially fully) occluding a major proportion of the dentinal tubules in a tooth. The major proportion may be 80% or more, preferably 90% or more.

Preferably the photosensitive composition is capable of substantially fully occluding a major proportion of the dentinal tubules in a tooth. The major proportion may be 60% or more, preferably 70% or more.

The synthetic nanocrystalline hydroxyapatite doped with a rare earth ion (or the photosensitive composition) may have particle lengths in the range 30-600 nm, preferably in the range 30-145 nm.

The synthetic nanocrystalline hydroxyapatite doped with a rare earth ion (or the photosensitive composition) may have an average particle length in the range 30-370 nm, preferably 40-320 nm, particularly preferably 50 to 110 nm, more preferably about 70 nm.

The synthetic nanocrystalline hydroxyapatite doped with a rare earth ion (or the photosensitive composition) may have particle diameters in the range 25-50 nm, preferably in the range 25-35 nm.

The synthetic nanocrystalline hydroxyapatite doped with a rare earth ion (or the photosensitive composition) may have an average particle diameter in the range 20-50 nm, preferably in the range 25-40 nm, particularly preferably in the range 25-35 nm, more preferably about 30 nm.

The synthetic nanocrystalline hydroxyapatite doped with a rare earth ion (or the photosensitive composition) may have an average particle aspect ratio in the range 2.4 to 10, preferably 2.4 to 3.8.

The photosensitive composition may be in a sintered (eg photosintered) or non-sintered form. The photosensitive composition may be a powder.

Generally the photosensitive composition may be obtained by any of a number of techniques including:

(1) solid-state reactions (see for example Ramachandra R et al *Solid state synthesis and thermal stability of HAP and HAP—β-TCP composite ceramic powders*. J. Mater. Sci. Mater. Med. 8 511-518. 1997; and Gutman E (1997) *Mechanochemistry of Materials*, Cambridge International Science Publishing, Cambridge, UK);

(2) co-precipitation (see for example Rhee S H and Tanaka J 1998 *Hydroxyapatite coating on a collagen membrane by biomimetic method*. Journal of American Ceramic Society 81 3029-3031; and Cuneyttas A et al (1997) *An investigation of the chemical synthesis and high-temperature sintering behaviour of calcium hydroxyapatite (HA) and tricalcium phosphate (TCP) bioceramics*. Journal Of Materials Science; Materials In Medicine 8: 91-96);

(3) sol-gel techniques (see for example Jillavenkatesa A and Condrate R A (1998) *Sol-gel processing of hydroxyapatite*. Journal of Materials Science. 33: 4111-4119; and Liu D et al. (2002) *Structural evolution of sol-gel-derived hydroxyapatite*. Biomaterials 23: 1679-1687); and (4) hydrothermal synthesis (see for example Riman R E et al: 2002 Solid State Ionics 151 393-402; and Liu J et al. (2003) *The influence of pH and temperature on the morphology of hydroxyapatite synthesized by hydrothermal method*. Ceramics International 29 629-633).

Preferably the photosensitive composition is obtained or obtainable by hydrothermal synthesis.

Preferably the photosensitive composition is obtained or obtainable by co-precipitation.

In a preferred embodiment, the photosensitive composition is obtained or obtainable by a process comprising:

(a) preparing an aqueous mixture of a calcium ion-containing solution, a phosphate ion-containing solution and a rare earth ion-containing dopant solution at a pH in the range 5 to 14;

(b) causing the formation of nanocrystalline hydroxyapatite doped with a rare earth ion; and (c) isolating the photosensitive composition.

The source of the calcium ions in the calcium ion-containing solution may be a calcium salt (eg a carbonate, nitrate or chloride salt).

The source of the phosphate ions in the phosphate ion-containing solution may be a phosphate salt (eg a hydrogen phosphate salt).

The source of the rare earth ions in the rare earth ion-containing solution may be a rare earth salt such as an optionally hydrated carbonate, acetate, hydroxide, nitrate, oxide or halide salt (preferably an acetate, citrate, nitrate, chloride, fluoride or hydrated chloride salt). The amount of the source of the rare earth ions used to prepare the rare earth-containing solution is preferably 5 wt % or less (particularly preferably 1 to 5 wt %, more preferably 1 to 2 wt %) of the total weight of the source of calcium ions used to prepare the calcium ion-containing solution and the source of the phosphate ions used to prepare the phosphate ion-containing solution. Specific examples of the source of rare earth ions include $Tm(OH)_3$, $Er(OH)_3$, $Tm_2O_3$, $Yb_2O_3$, $Ho_2O_3$, $Er_2O_3$, $TmF_3$, $ErF_3$, $Tm(NO_3)_3 \cdot 5H_2O$, $Er(NO_3)_3 \cdot 5H_2O$ and $ErCl_3$.

The pH of the aqueous mixture in step (a) may be in the range 8 to 14, preferably in the range 8 to 12. The pH of the aqueous mixture in step (a) may be adjusted to be in the range 8 to 14, preferably in the range 8 to 12. The pH of the aqueous mixture may be adjusted by the addition of a base.

In step (a), the aqueous mixture may be aged (eg for 24 hours or more).

Step (b) may be carried out over a period in the range 3 to 72 hours, preferably 18 to 48 hours, particularly preferably 18 to 30 hours, more preferably about 24 hours.

Preferably step (b) is carried out substantially at ambient temperature (eg room temperature). Step (b) carried out substantially at ambient temperature advantageously permits nanocrystalline hydroxyapatite doped with a rare earth ion to be synthesised with nanoparticle sizes and morphology which offer desirable levels of coverage on coating a tooth.

Preferably step (b) is carried out at an elevated temperature. Step (b) carried out at an elevated temperature advantageously permits nanocrystalline hydroxyapatite doped with a rare earth ion to be synthesised with desirable particle sizes and morphology without the need for post-reaction high-temperature annealing. Step (b) may be carried out at a temperature in the range 80-350° C., preferably 80-250° C. (eg at about 200° C.).

In step (b), the aqueous mixture may be at an elevated vapour pressure.

The calcium ion-containing solution and the phosphate ion-containing solution in step (a) is preferably such that the molar ratio of Ca:P in the aqueous mixture is about 1.67. For example in step (a), the phosphate ion-containing solution may be added dropwise to the calcium ion-containing solution until the molar ratio of Ca:P in the aqueous mixture is about 1.67.

Preferably in step (a) a source of fluoride ions is added to the aqueous mixture. The amount of the source of fluoride ions added in step (a) is preferably 5 wt % or less (particularly preferably 2 wt % or less) of the total weight of the source of calcium ions used to prepare the calcium ion-containing solution and the source of the phosphate ions used to prepare the phosphate ion-containing solution. For example, the source of fluoride ions may be calcium fluoride or stannous fluoride. Calcium fluoride helps to solubilize the rare earth ions and to lower the laser melting temperature of the photosensitive composition. The incorporation of fluoride ions in the lattice contributes to acid resistance.

Preferably in step (a) a source of aluminium ions is added to the aqueous mixture. The amount of the source of aluminium ions added in step (a) is preferably such that the aluminium ions are present in an amount of 5 wt % or less (particularly preferably 2 wt % or less) of the total weight of the source of the calcium ions used to prepare the calcium ion-containing solution and the source of the phosphate ions used to prepare the phosphate ion-containing solution. The source of aluminium ions may be an aluminium salt. For example the source of aluminium ions may be aluminium nitrate, aluminium phosphate or aluminium trichloride hexahydrate.

Viewed from a further aspect the present invention provides a process for preparing a photosensitive composition as hereinbefore defined comprising:

(a) preparing an aqueous mixture of a calcium ion-containing solution, a phosphate ion-containing solution and a rare earth ion-containing solution at a pH in the range 5 to 14;

(b) causing the formation of synthetic nanocrystalline hydroxyapatite doped with a rare earth ion; and (c) isolating the photosensitive composition.

Steps (a), (b) and (c) may be as hereinbefore defined.

Photosensitization of nanocrystalline hydroxyapatite with a rare earth ion facilitates the efficient absorption of laser energy and promotes rapid ablation. This may be exploited to give efficient packing and sintering during tooth filling. Photosensitization minimises collateral damage of healthy tissue by keeping the temperature low (eg below 41° C.).

Viewed from a yet further aspect the present invention provides a method for combating (eg treating or preventing) a dental condition in a tooth of a human or non-human animal subject comprising:

(A) applying an amount of a photosensitive composition as hereinbefore defined or a physiologically tolerable formulation thereof to the tooth to cause at least partial occlusion of dentinal tubules; and (B) irradiating the amount of the photosensitive composition with laser irradiation so as to promote densification.

By exploiting the photosensitive composition, the method of the invention may minimize the risk of collateral tissue damage, the risk of plasmonic emission due to the presence of Ca and Ca+ states and the risk of generating reactive oxygen species via radiation absorption from the plasmonic transition and/or due to multi-photon absorption.

Preferably the rare earth ions exhibit absorption bands which substantially match or overlap one or more absorption bands of the synthetic nanocrystalline hydroxyapatite (eg the first harmonic of the phosphate band or the fundamental OH band). By targeting absorption bands, the method of the invention proceeds predominantly in a controlled manner by breaking the required bonds. Energy absorption becomes very efficient and may lead to rapid local densification.

The photosensitive composition may be formulated for use in the method of the invention in a physiologically tolerable formulation. The formulation may be a dispersion, suspension or paste. Preferably the formulation is a dispersion. Particularly preferably the dispersion is an aqueous, ketonic or alcoholic dispersion. For example, the dispersion is in acetone, water (eg distilled water), isopropanol, ethanol, methanol or an aqueous solution of sodium metaphosphate $[NaPO_3]_n$. Preferably the dispersion is in methanol or ethanol.

Typically synthetic nanocrystalline hydroxyapatite doped with a rare earth ion is present in the physiologically tolerable formulation in an amount of 0.5 w/v % or more, preferably 3 w/v % or more, particularly preferably 5 w/v % or more. An amount of synthetic nanocrystalline hydroxyapatite doped with a rare earth ion of 5 w/v % or more may form advantageously a complete coating similar to a smear layer on the tooth. The formation of a protective smear layer of synthetic nanocrystalline hydroxyapatite doped with a rare earth ion overlying occluded tubules is beneficial to combat sensitivity.

The dental condition may be dental caries, tooth wear or decay, sensitivity (eg acute hypersensitivity) or pain attributable to carious infection.

Preferably in step (A) the amount of the photosensitive composition or physiologically tolerable formulation thereof is applied to an exposed dentinal surface.

Preferably the laser irradiation is eye-safe.

Preferably the laser irradiation is infrared irradiation. Particularly preferably the laser irradiation is near infrared, mid infrared or short wavelength infrared irradiation. More preferably the laser irradiation is short wavelength infrared irradiation The wavelength of laser irradiation may be in the range 980 to 4500 nm (preferably 1400 to 3000 nm).

The wavelength of laser irradiation may be coincident with one or more absorption bands of the $OH^-$ ion, $CO_3^{2-}$ ion, phosphate ion or water.

Preferably the wavelength of laser irradiation is in the range 1400 nm to 1800 nm. A wavelength in the range 1450-1800 nm minimizes side-affects and allows (for example) more than one order of magnitude more pulse energy to be delivered to a subject whilst still retaining an eye-safe Class I classification according to the International Standard on the Safety of Laser Products (IEC 60825-1). A wavelength in the range 1400 to 1800 nm is advantageously coincident with the absorption bands of the OH$^-$ ion first harmonic.

Preferably the wavelength of laser irradiation is in the range 2700 to 3500 nm. A wavelength in the range 2700 to 3000 nm is advantageously coincident with the fundamental OH$^-$ ion absorbtion band and phosphate ion harmonics.

Preferably the wavelength of laser irradiation is in the range 1900 to 2100 nm. A wavelength in the range 1900 to 2100 nm is advantageously coincident with the absorption bands of the OH$^-$ ion overtone and $CO_3^{2-}$ harmonics.

Preferably the wavelength of laser irradiation is in the range 4000 to 4500 nm. A wavelength in the range 4000 to 4500 nm is advantageously coincident with the absorption bands of the OH$^-$ ion and $CO_2$ harmonics.

The laser may be a continuous wave laser (eg a near IR continuous wave laser). The laser may be a pulsed laser (eg an ultrashort pulsed laser). The laser may generate ultrashort pulses. The pulsed laser may be a pico, nano, micro or femtosecond pulsed laser. The laser may emit pulses of a length in the range 20 fs to 150 ps (eg about 135 ps). Preferably the pulsed laser is a femtosecond pulsed laser.

The laser may be (for example) a $CO_2$ laser, an Er-doped or Ho-doped Nd-YAG laser, a Tm-doped laser, a Ti-sapphire laser, a diode pumped laser (such as a Yb-doped or Cr-doped crystal laser) or a fibre optic laser.

The laser may be a short pulsed fibre laser in which the power is delivered (for example) using a silica fibre.

The pulse energy is typically in the range 1 nJ to 1 µJ. The pulses may be emitted with a repetition rate up to 10 GHz (eg 100 MHz). The average power of the laser may be sub-Watt.

The advantages of the photosensitive composition of the invention may be further exploited in methods which are solely cosmetic (non-restorative).

Viewed from a still yet further aspect the present invention provides a cosmetic method for whitening or veneering a tooth of a human or non-human animal subject comprising:

(1) applying an amount of a photosensitive composition as hereinbefore defined or a physiologically tolerable formulation thereof to a surface of the tooth other than a dentinal surface; and (2) irradiating the amount of the photosensitive composition with laser irradiation so as to promote densification.

Preferably in step (1) the photosensitive composition is applied solely to the enamel surface of the tooth.

A rare-earth ion emits radiation when excited at an absorption wavelength. In a further patentable aspect, the present invention is able to capture the emitted light to generate an image of (for example) a dental cavity into which a photosensitive composition of the invention has been administered.

Viewed from an even still yet further aspect the present invention provides a method for generating an image of an exposed dentinal surface of a tooth of a human or non-human animal subject comprising:

(A) administering an amount of a photosensitive composition as hereinbefore defined or a physiologically tolerable formulation thereof to the exposed dentinal surface;

(B) irradiating the photosensitive composition or physiologically tolerable formulation thereof with irradiation;

(C) capturing the radiation emitted by the photosensitive composition or physiologically tolerable formulation thereof; and (D) generating from the radiation emitted by the photosensitive composition or physiologically tolerable formulation thereof an image of the exposed dentinal surface.

The rapid provision of an image of the site of administration provides (for example) information on the state of crystallisation of the rare earth ion-containing dopant, the structure and morphology of the photosensitive composition or the health of the dentine.

The exposed dentinal surface may be a part of a dental cavity or a characteristic of dental caries.

Steps (B), (C) and (D) may be carried out spectroscopically. Steps (B), (C) and (D) may be carried out by IR, Raman or fluorescence spectroscopy.

Viewed from an even still further aspect the present invention provides a physiologically tolerable formulation as hereinbefore defined.

Viewed from a furthest aspect the present invention provides photosensitive composition as hereinbefore defined or physiologically tolerable formulation as hereinbefore defined for use in restorative or cosmetic dentistry.

Figure 2A:
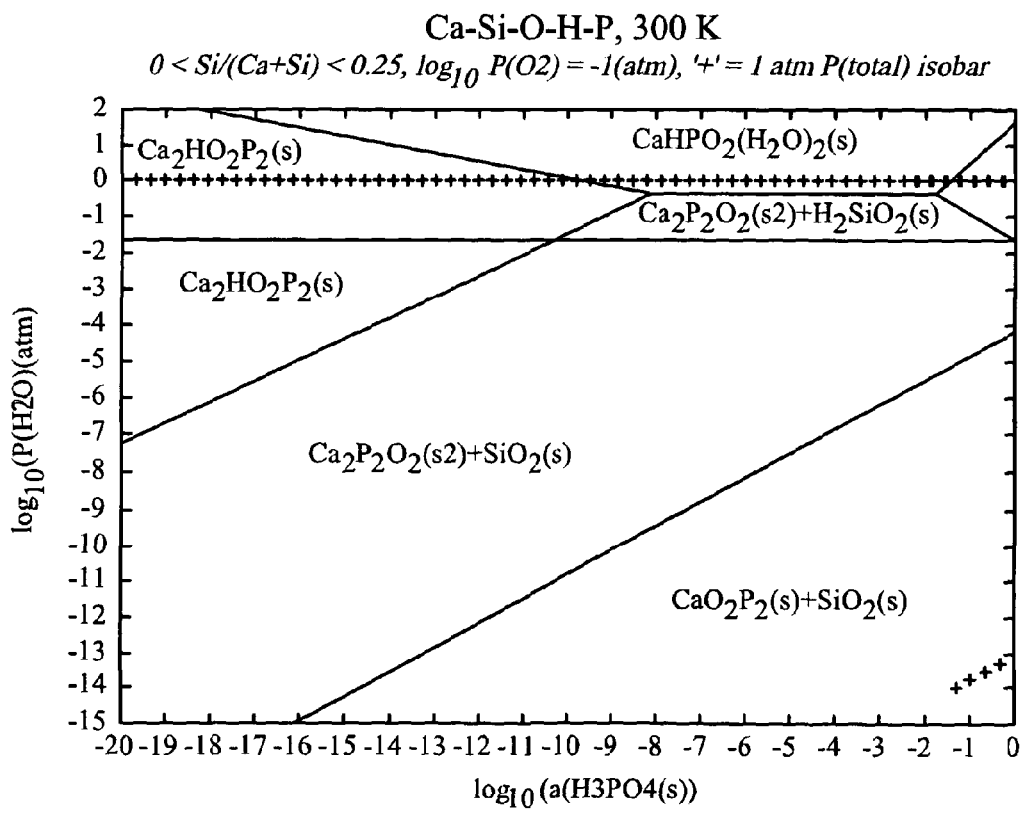
Figure 2B:
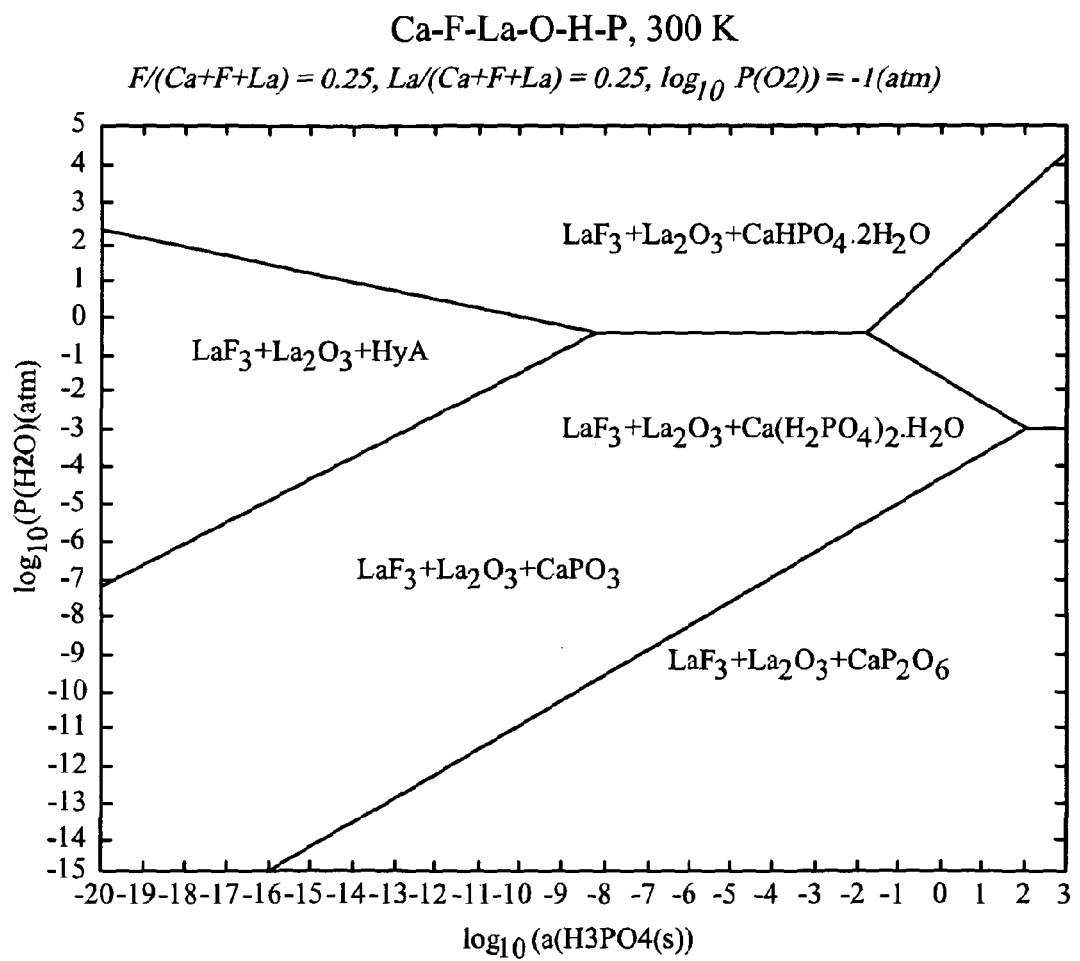
Figure 3:
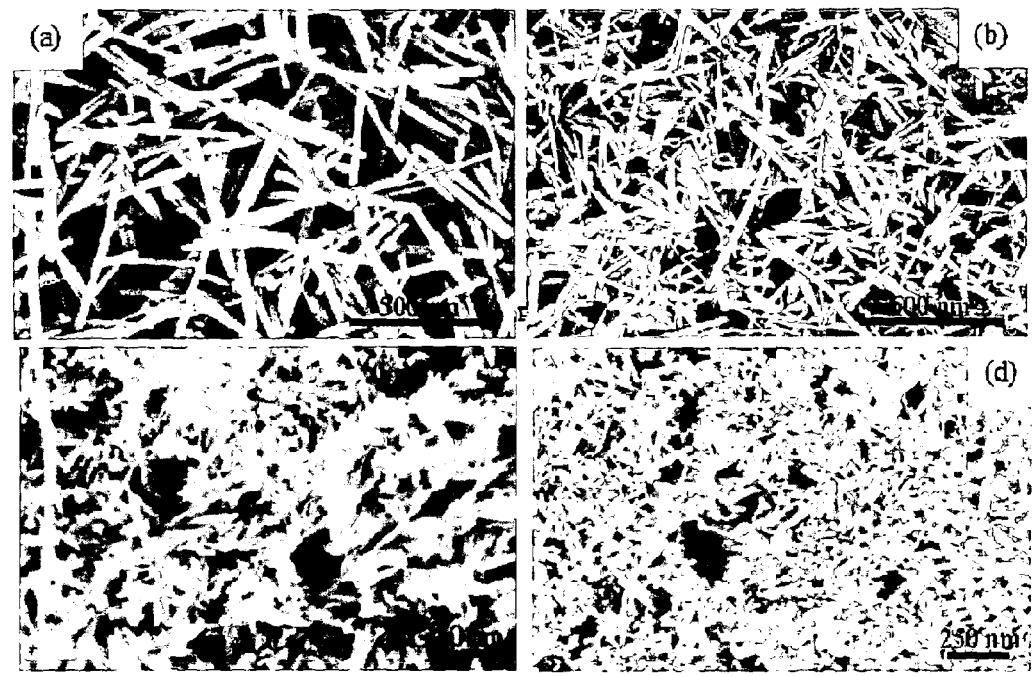
Figure 4:
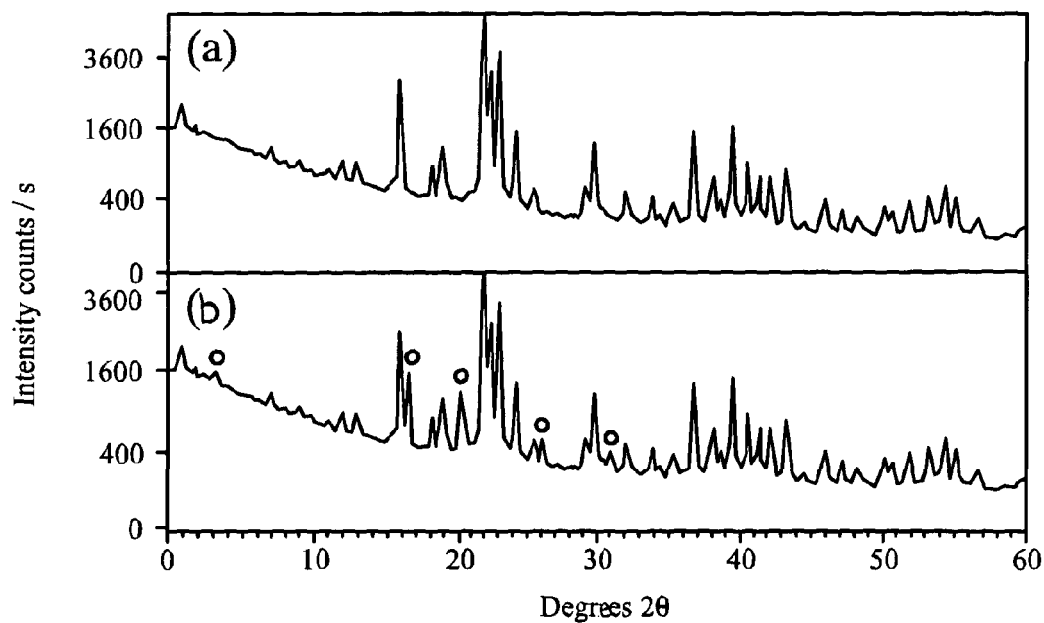
Figure 5:
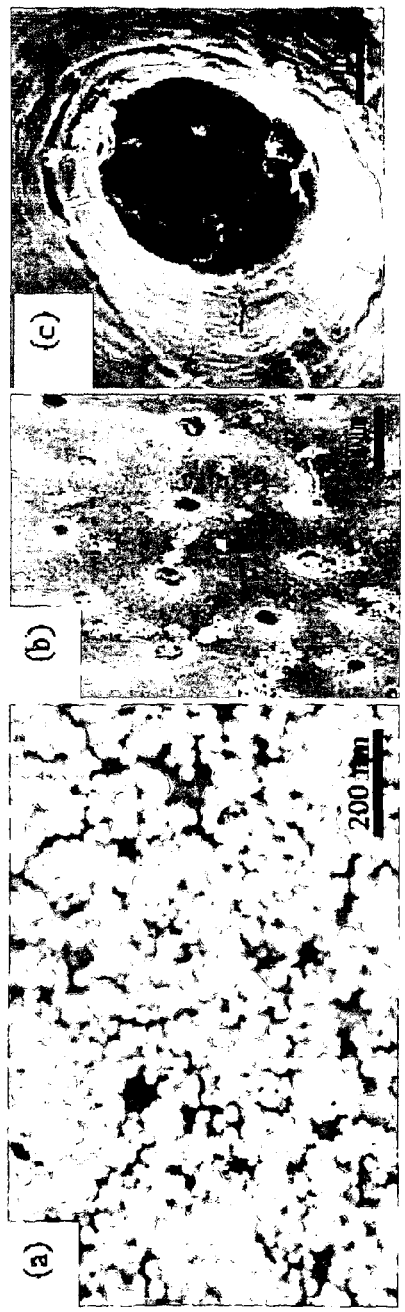
Figure 7:
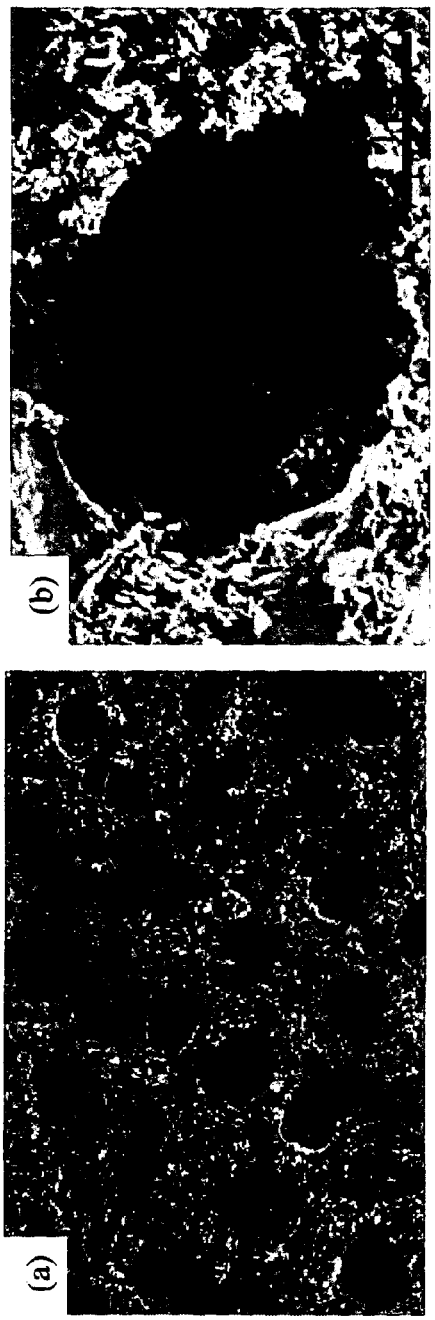
Figure 6:
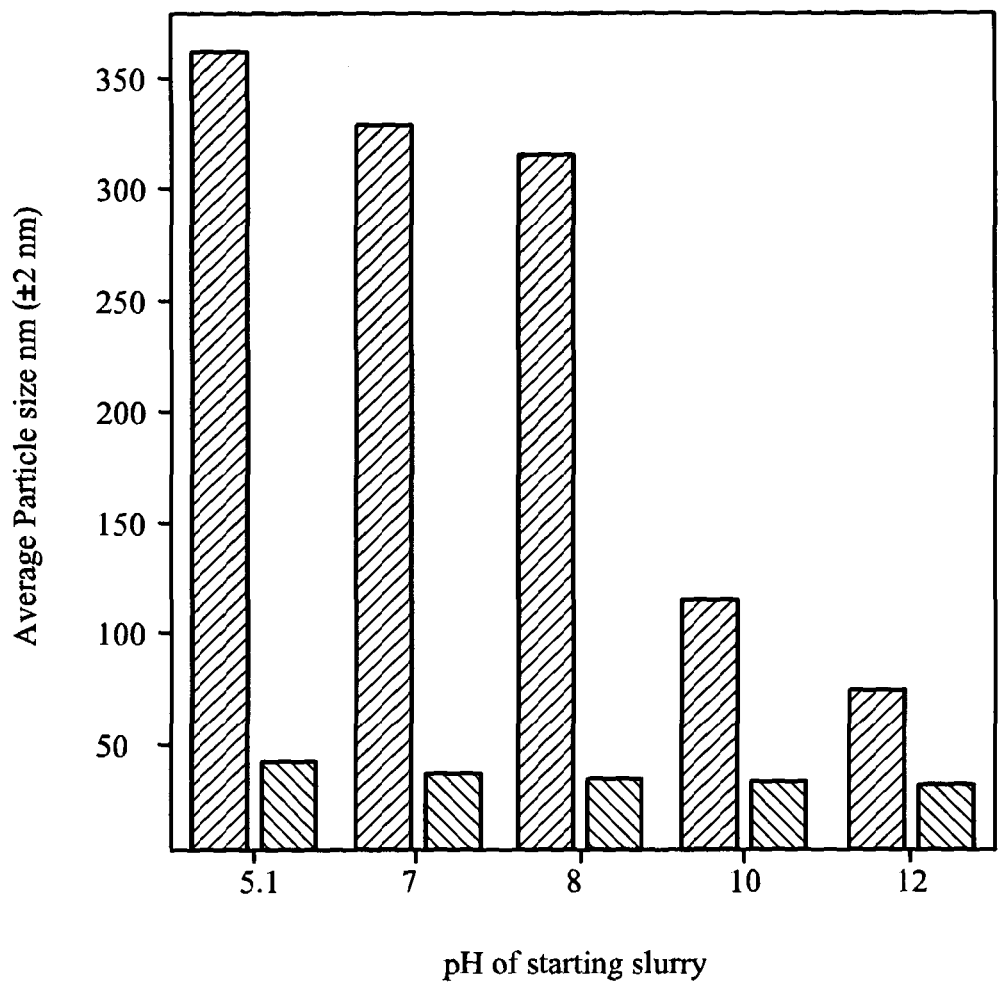
Figure 8:
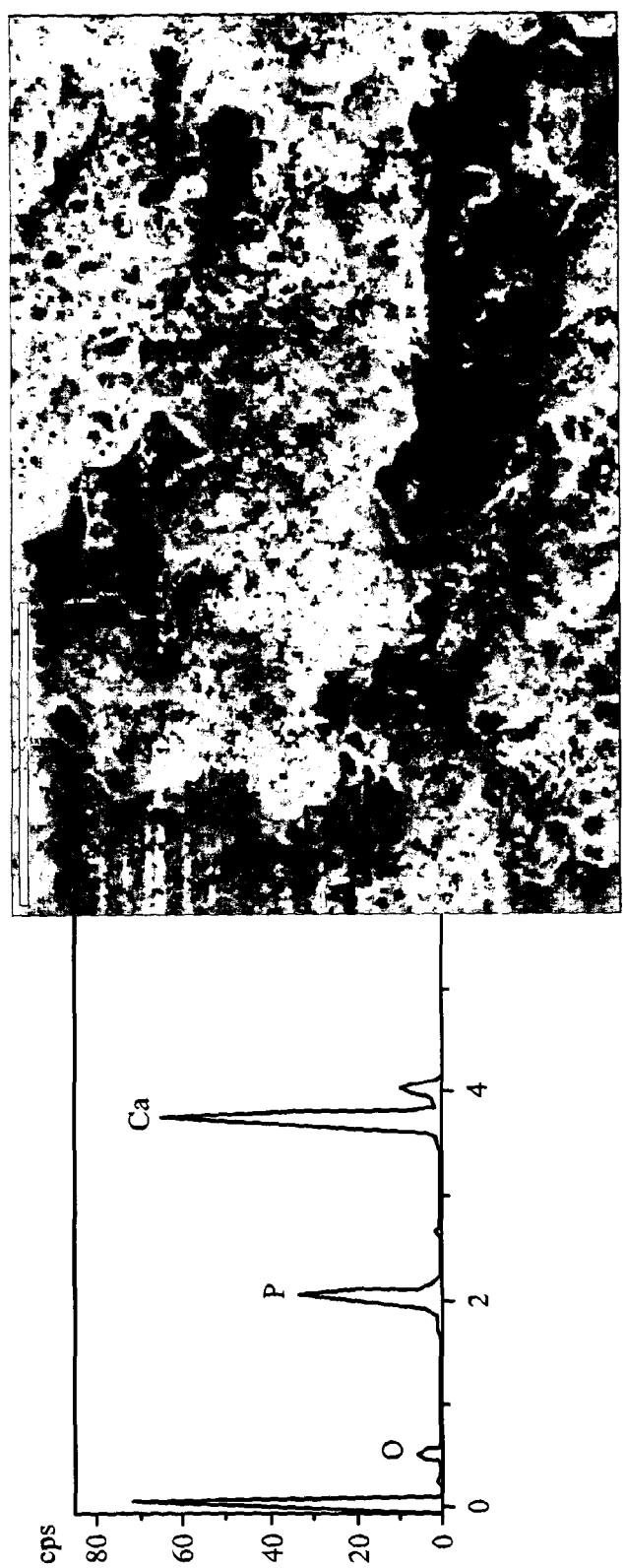
Figure 9A:
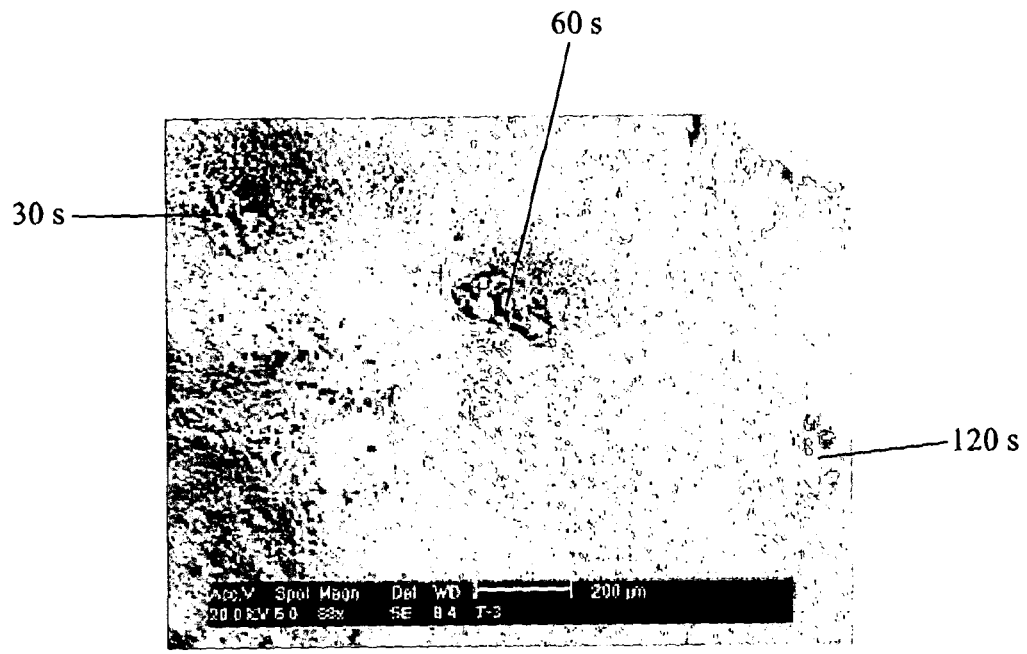
Figure 9B:
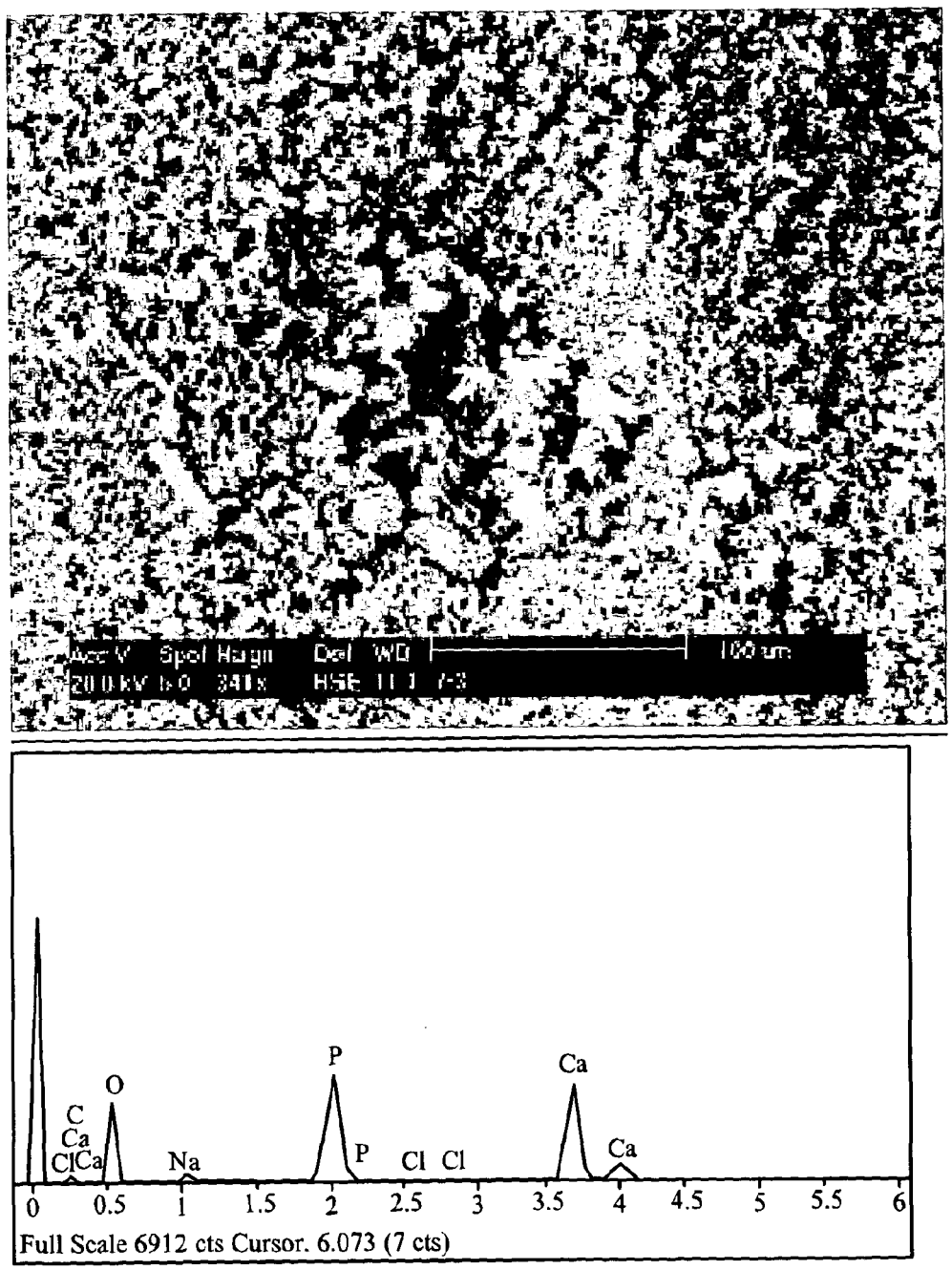
Figure 9C:
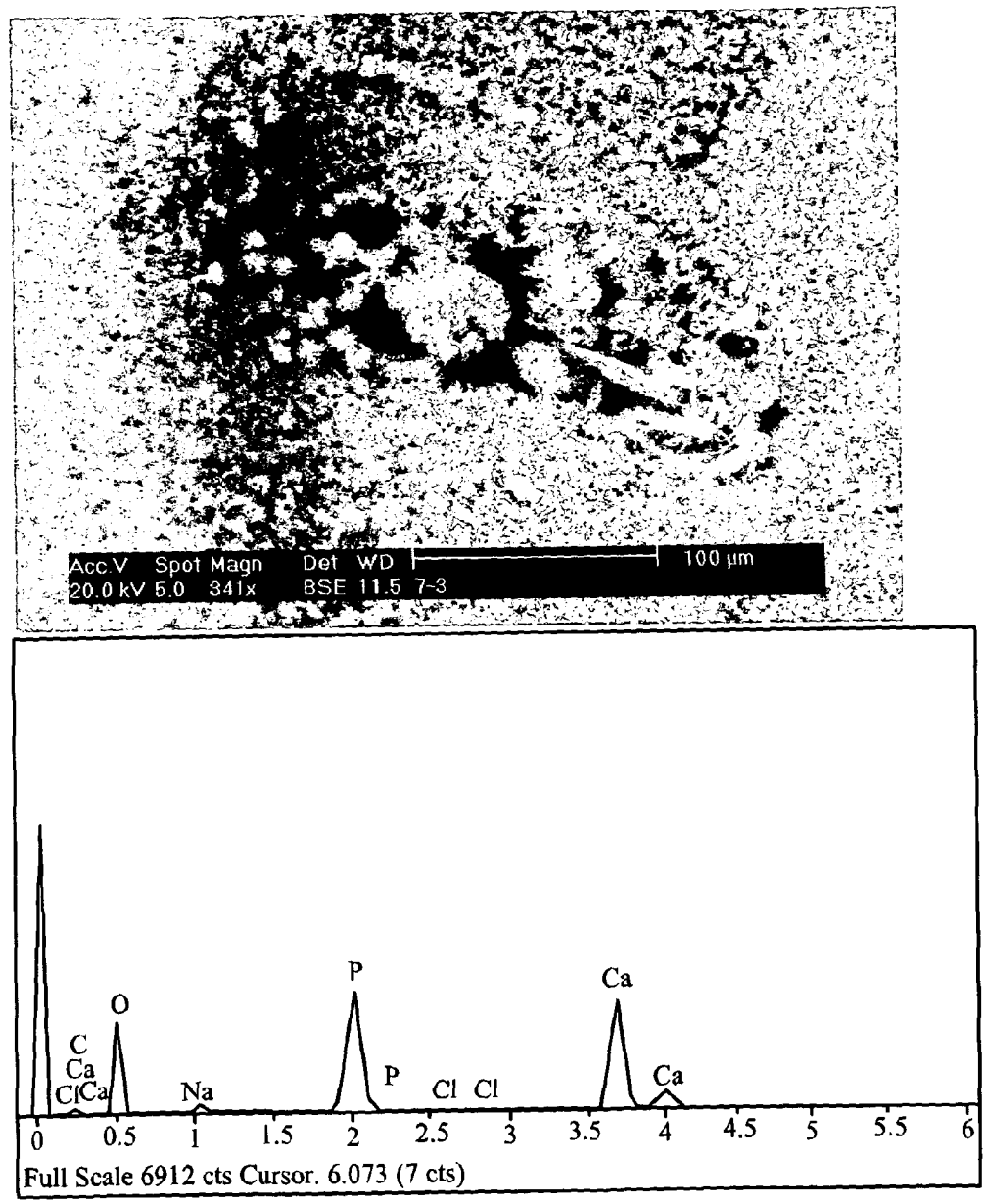
Figure 9D:
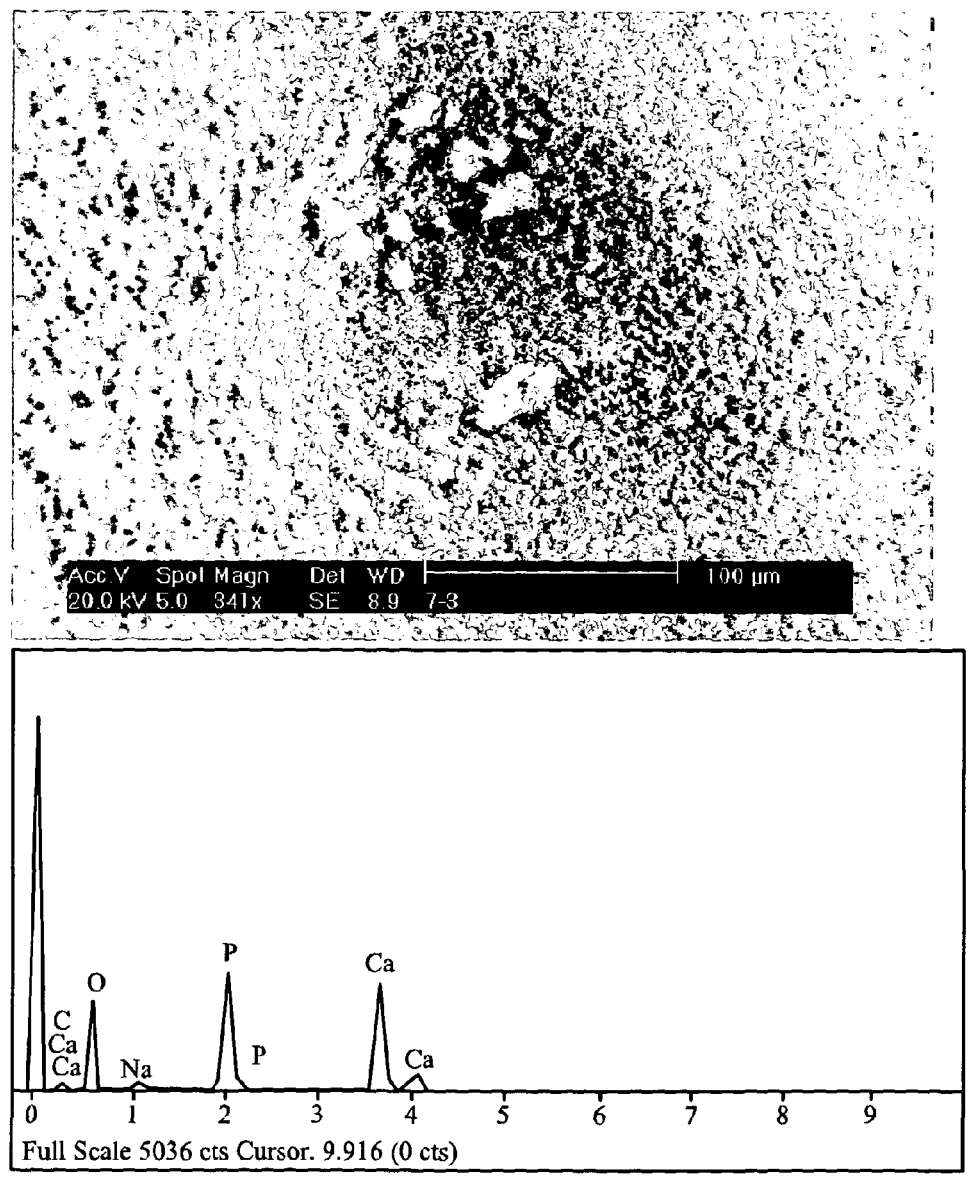
Figure 10:
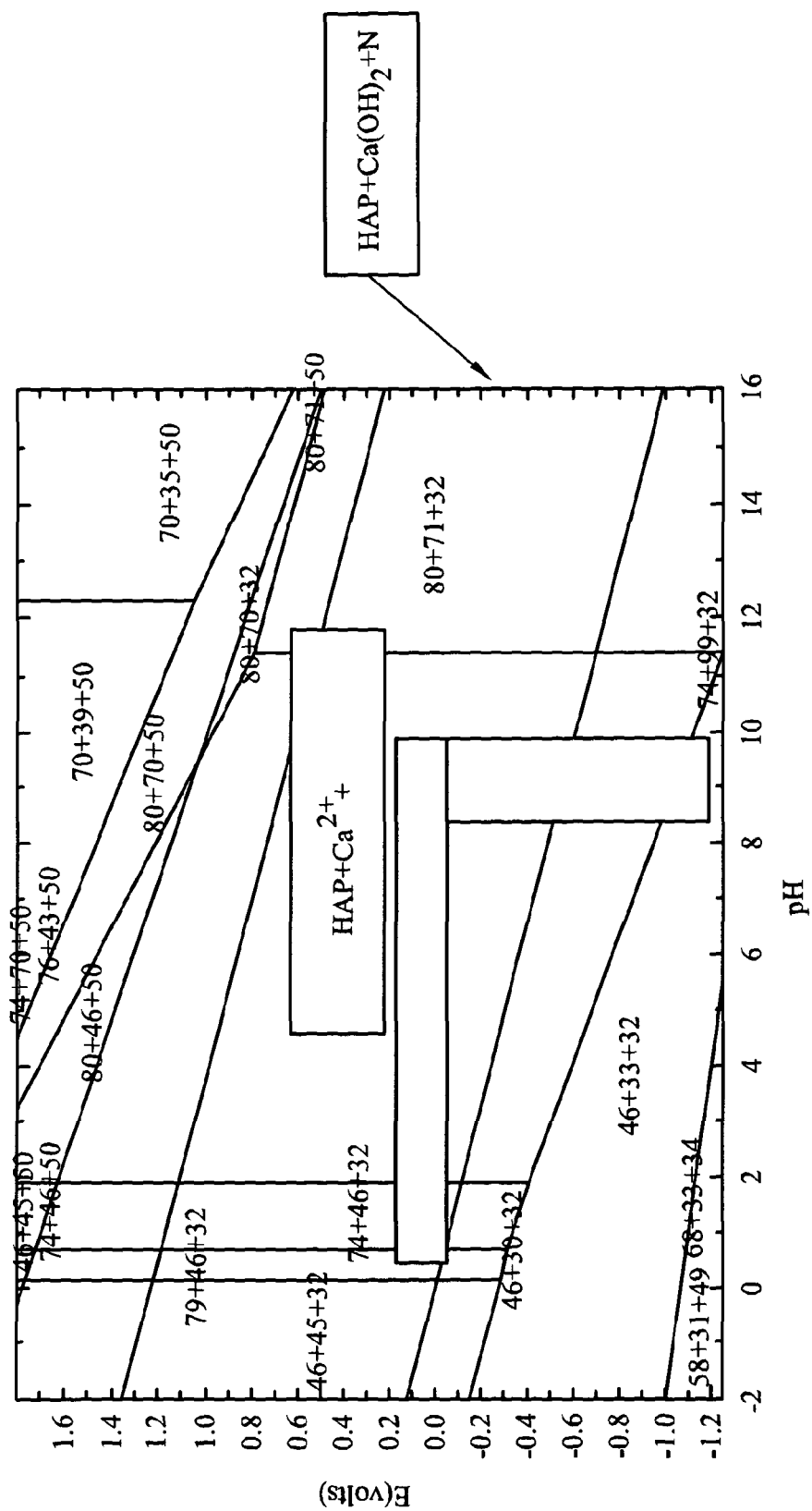
Figure 13:
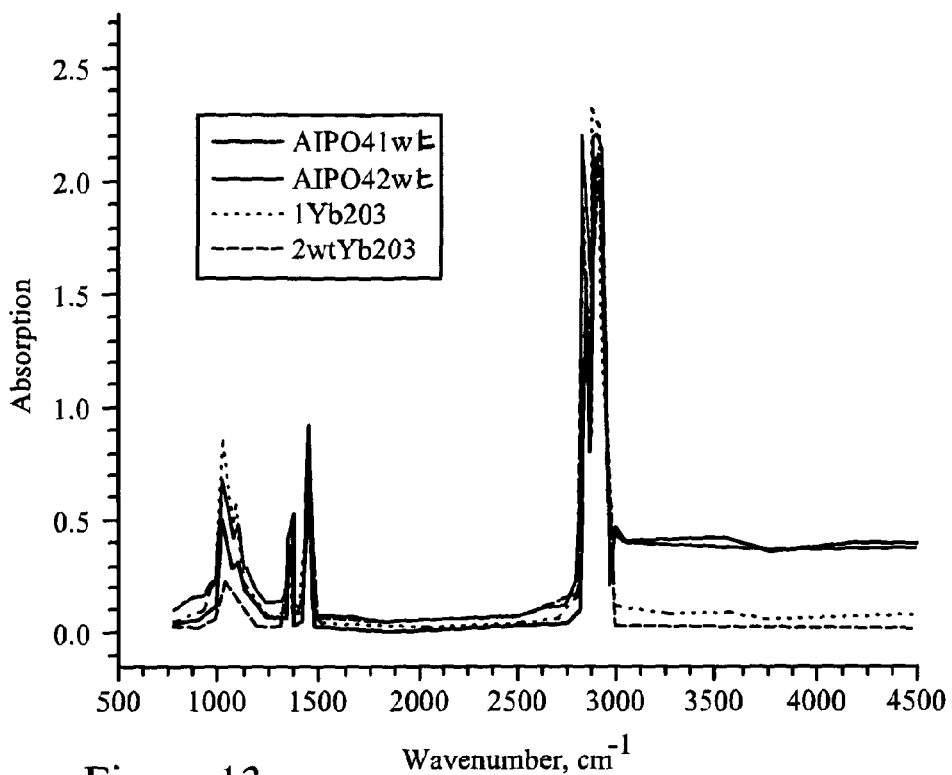
Figure 14:
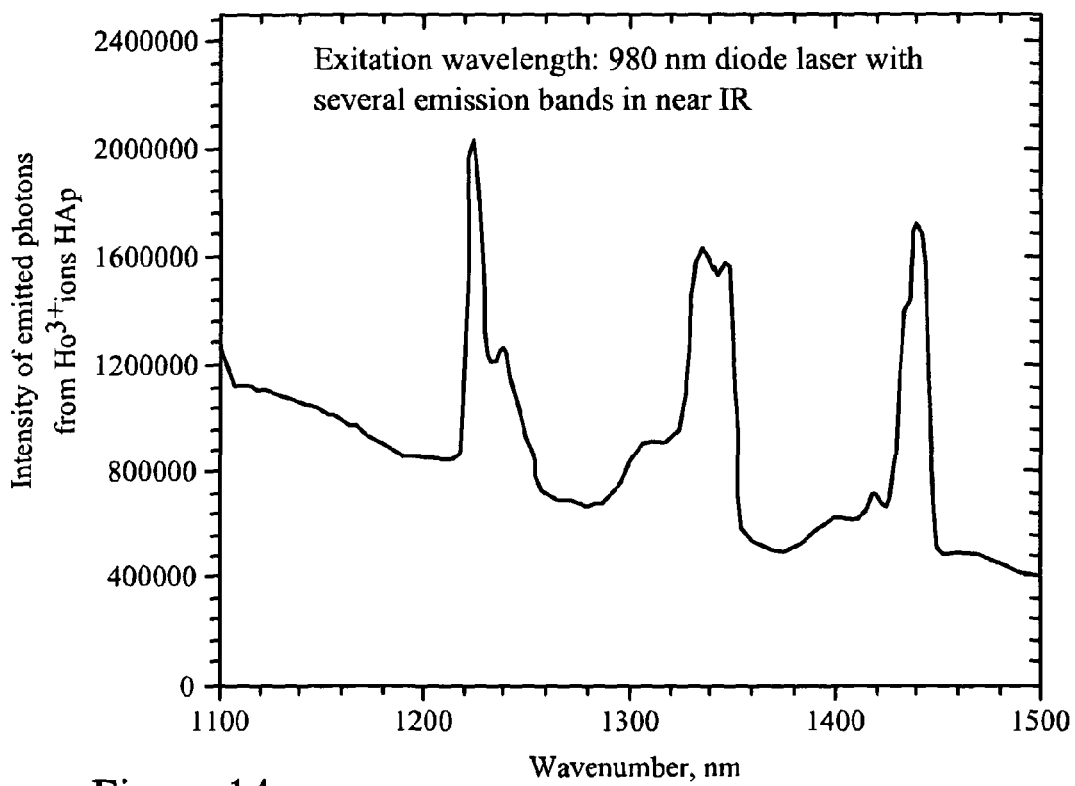
Figure 16:
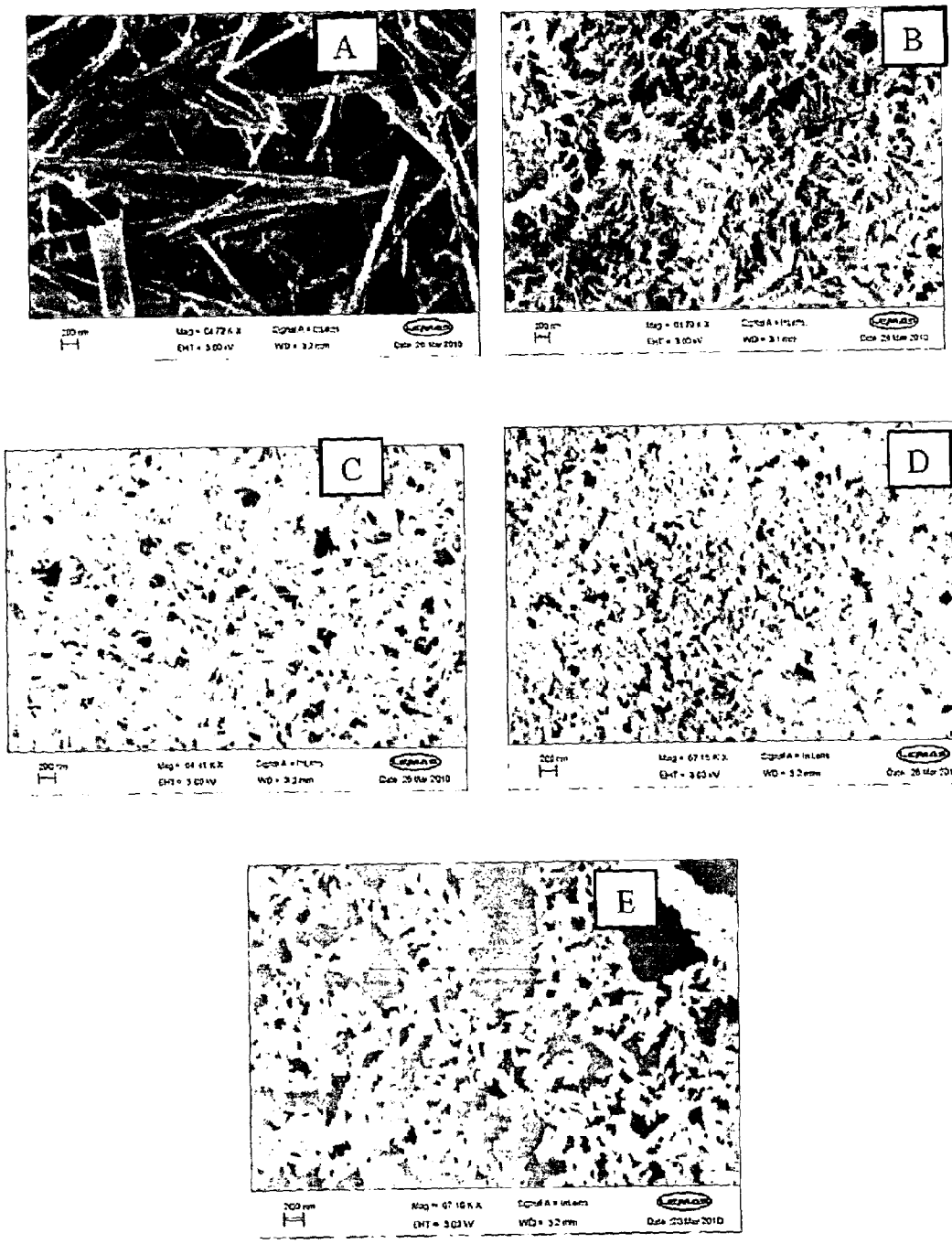
Figure 17:
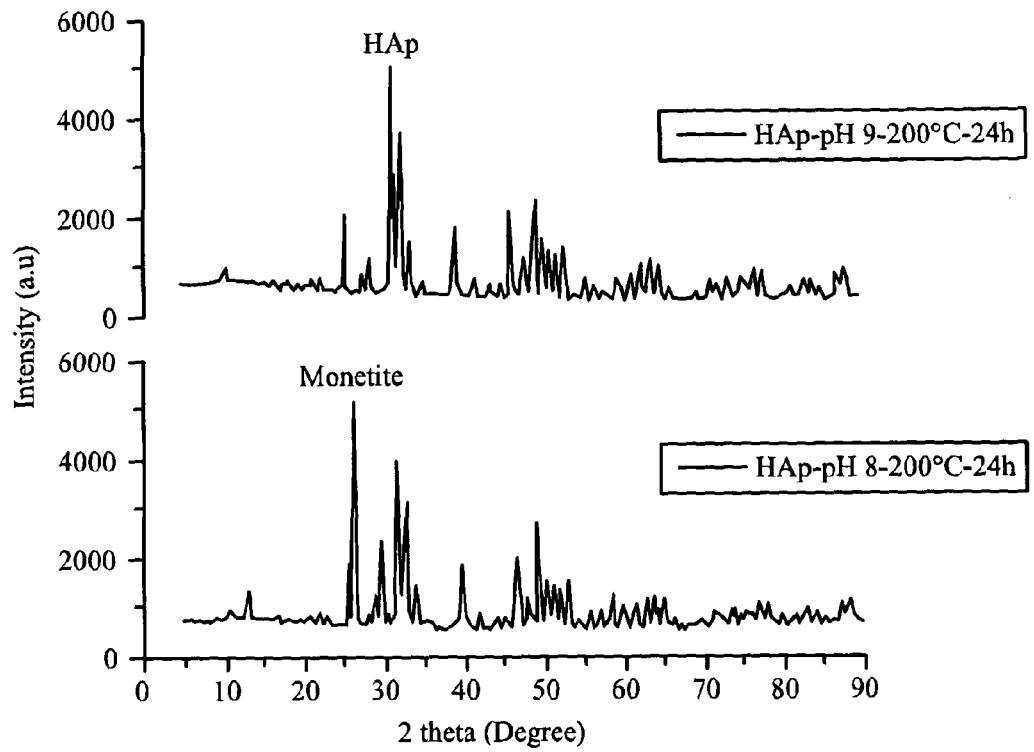
Figure 18:
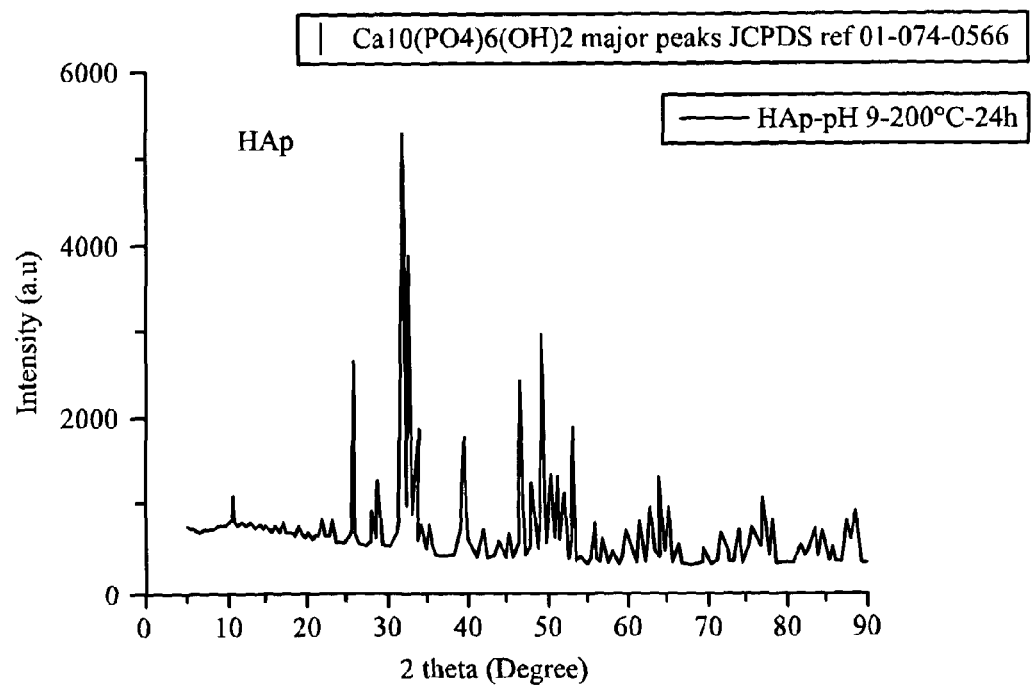
Figure 19:
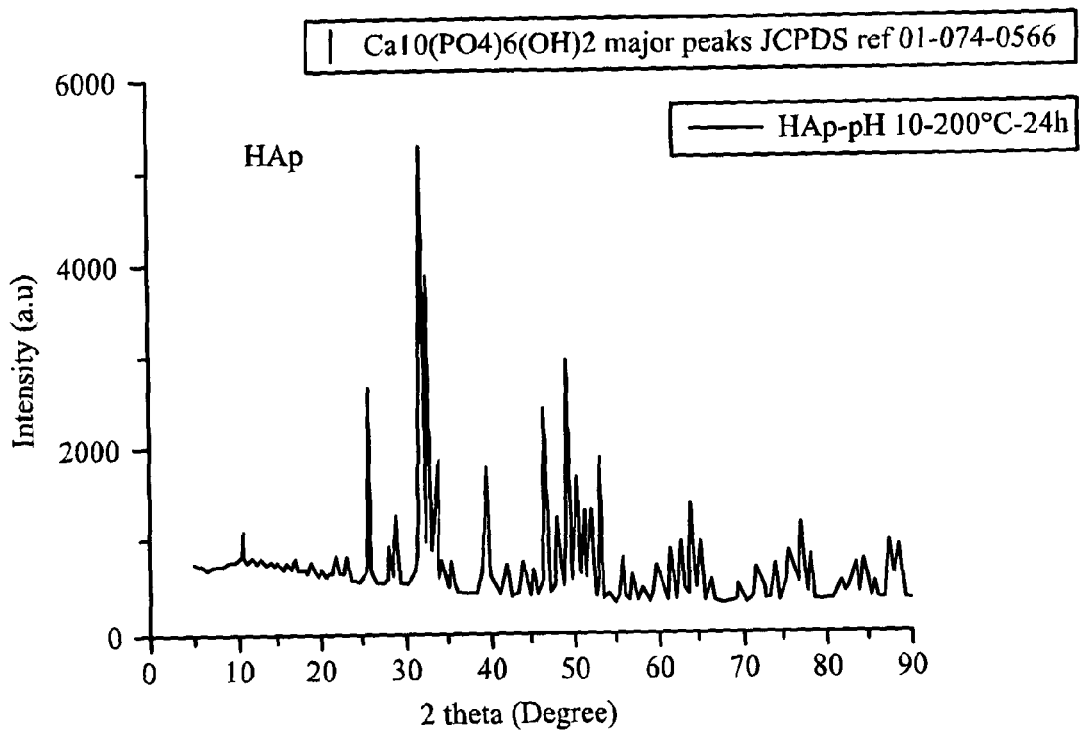
Figure 20:
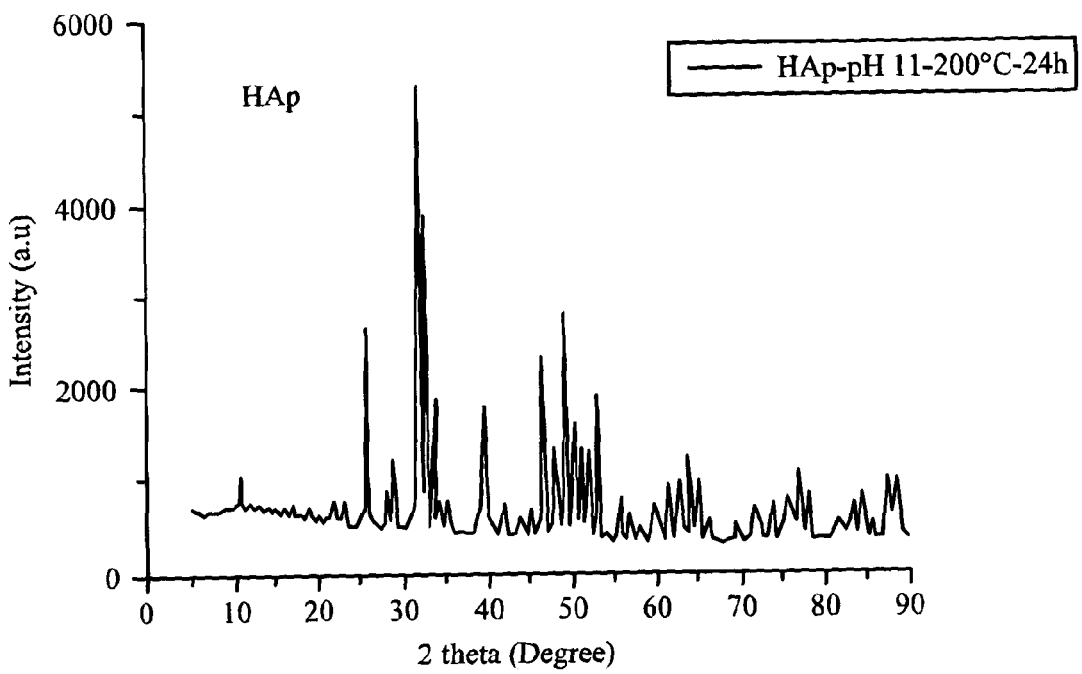
Figure 21:
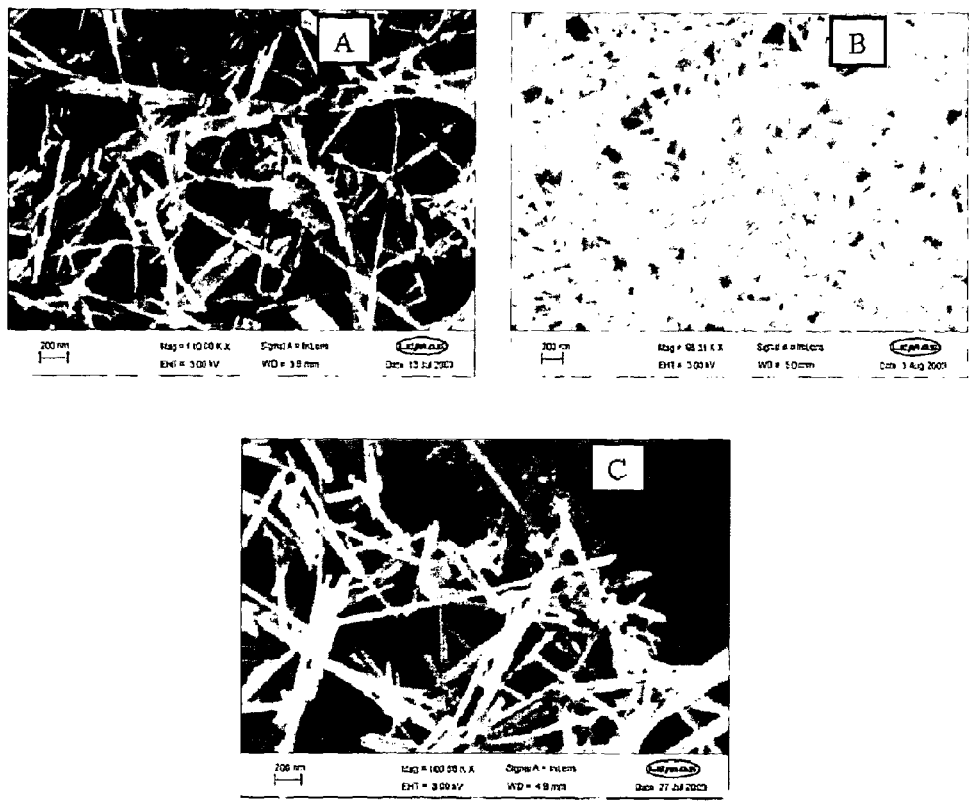
Figure 22:
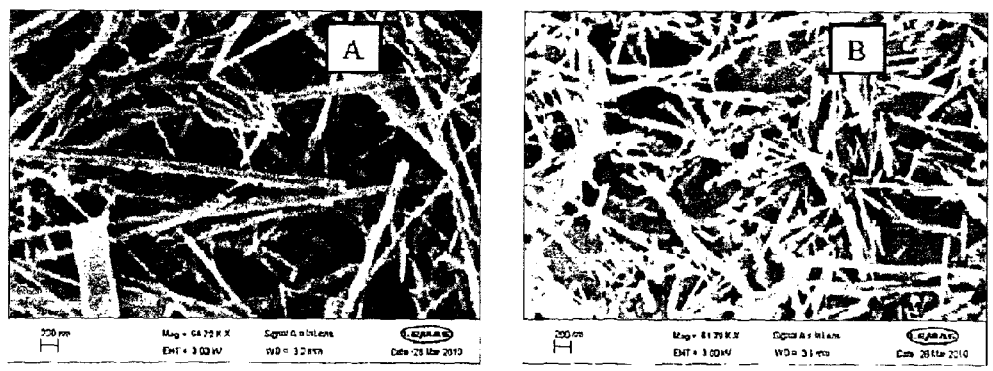
Figure 23:
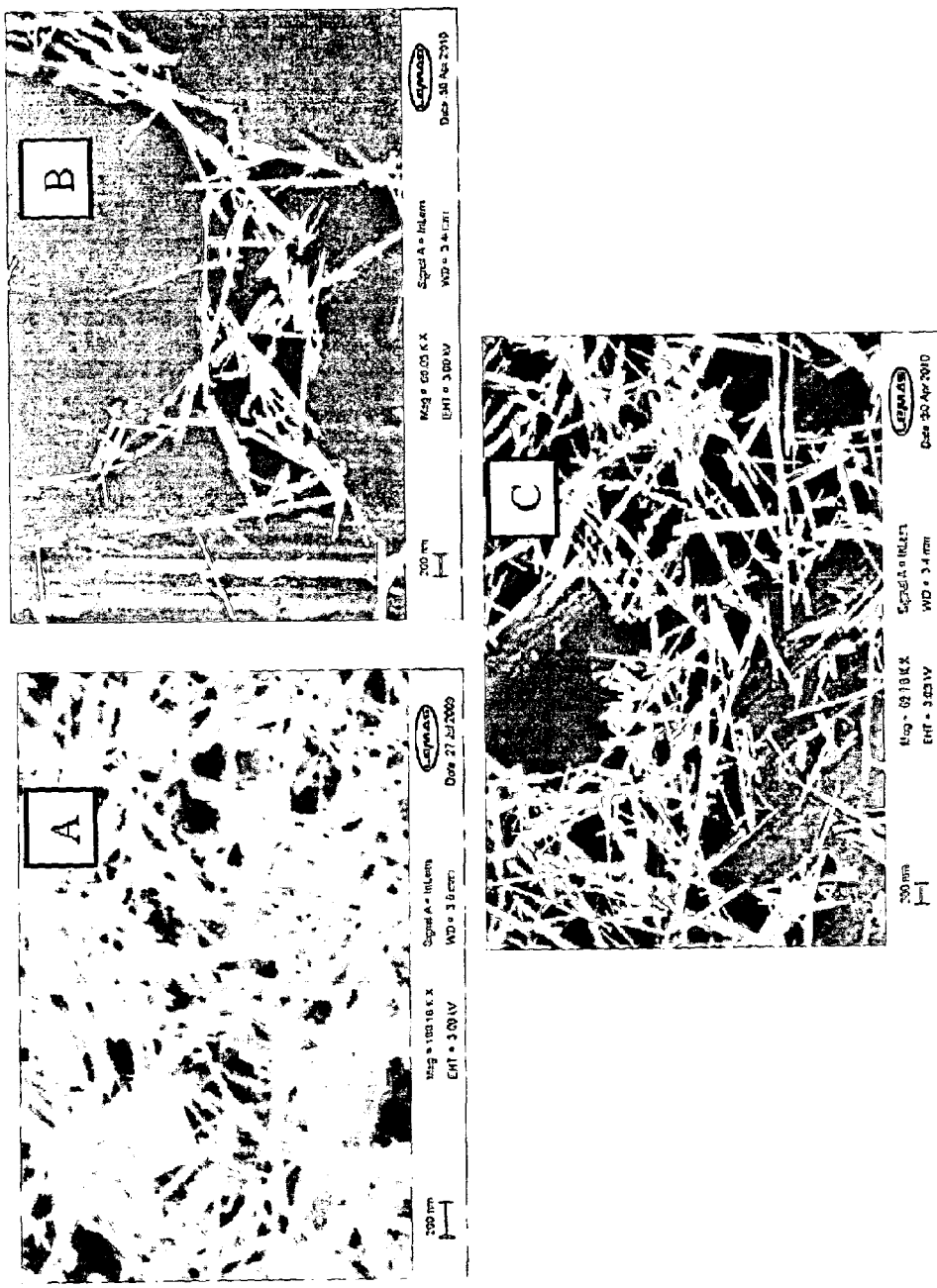
Figure 24:
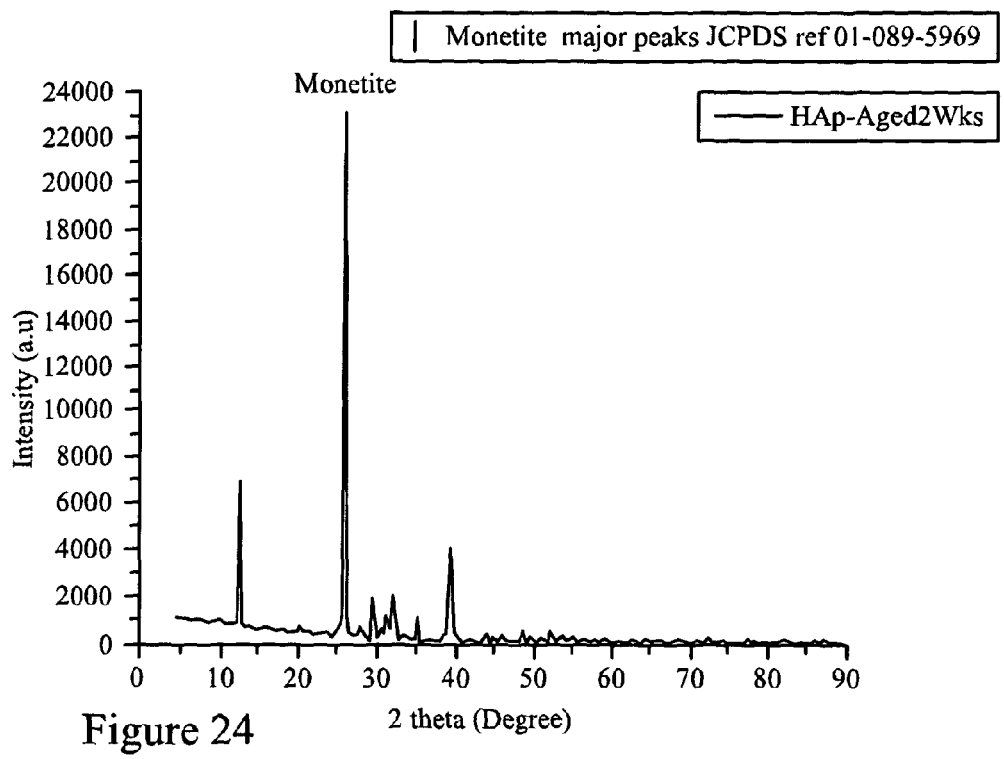
Figure 26:
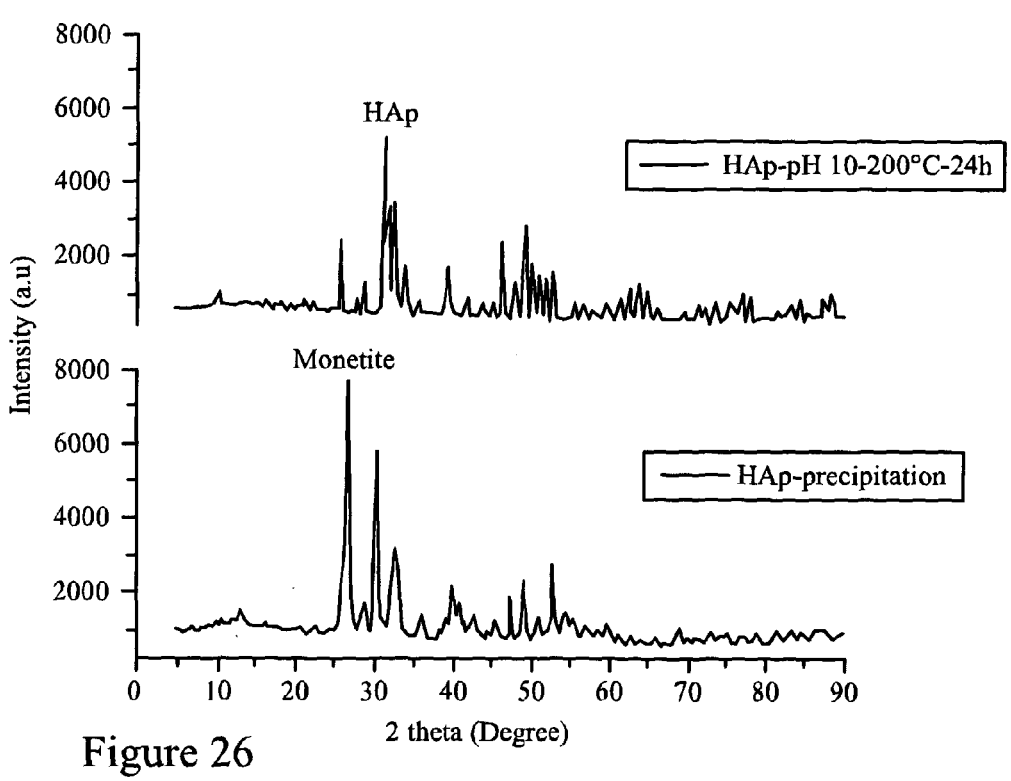
Figure 25:
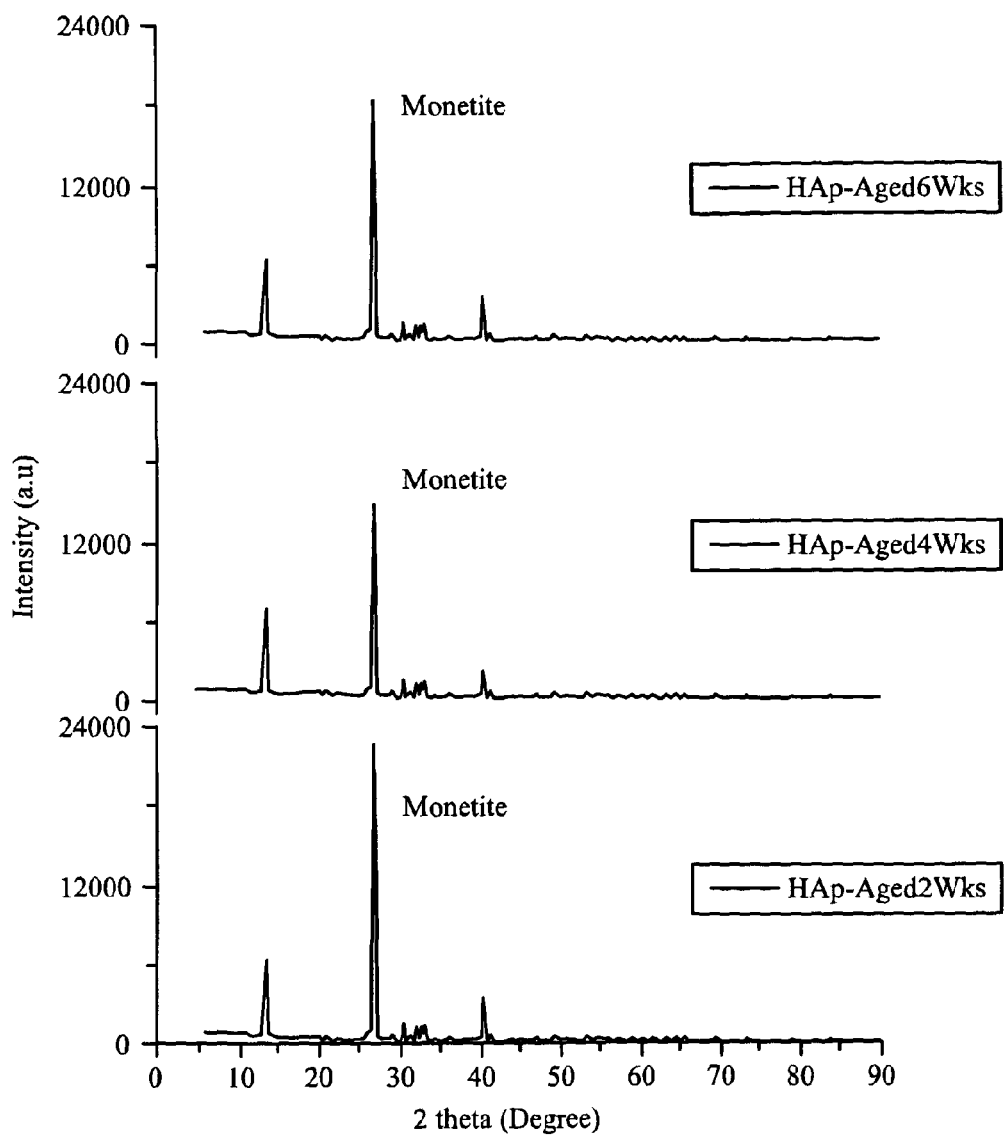
Figure 27:
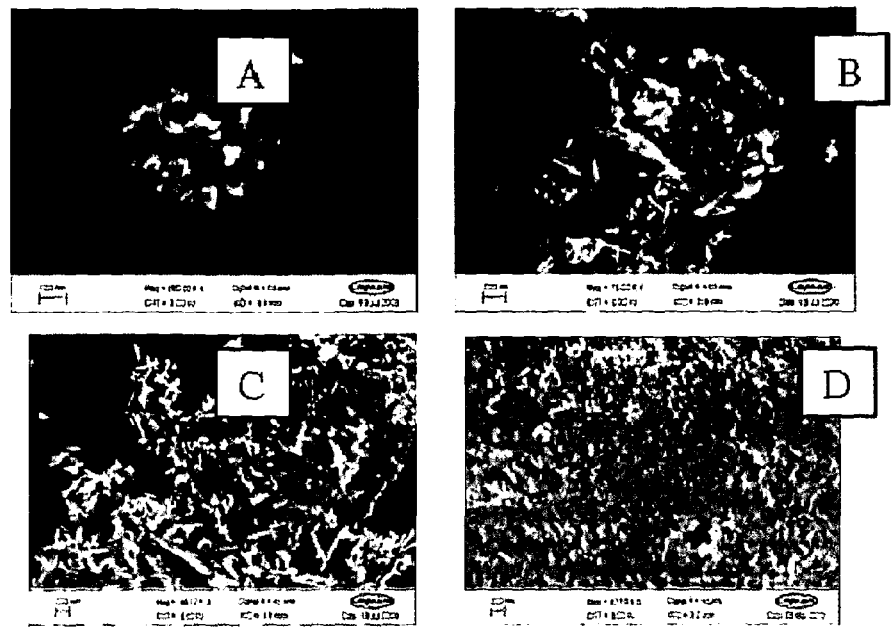
Figure 28:
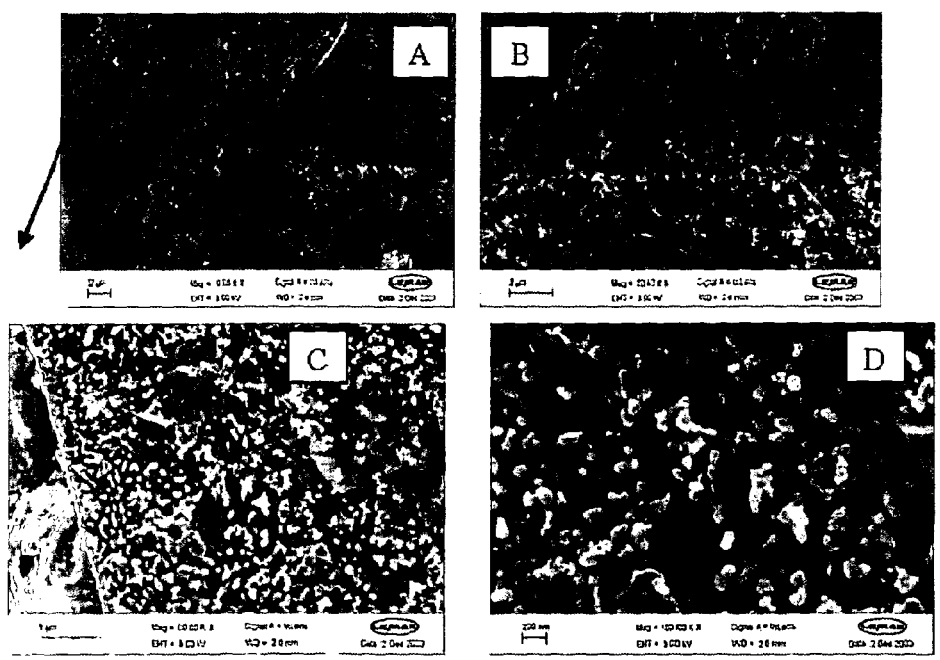
Figure 29:
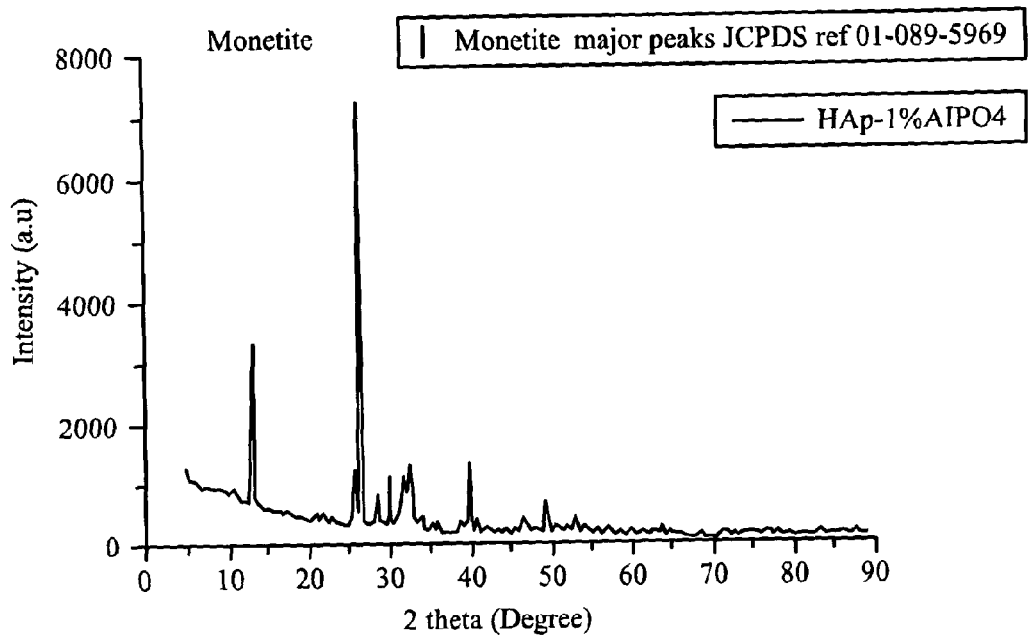
Figure 30:
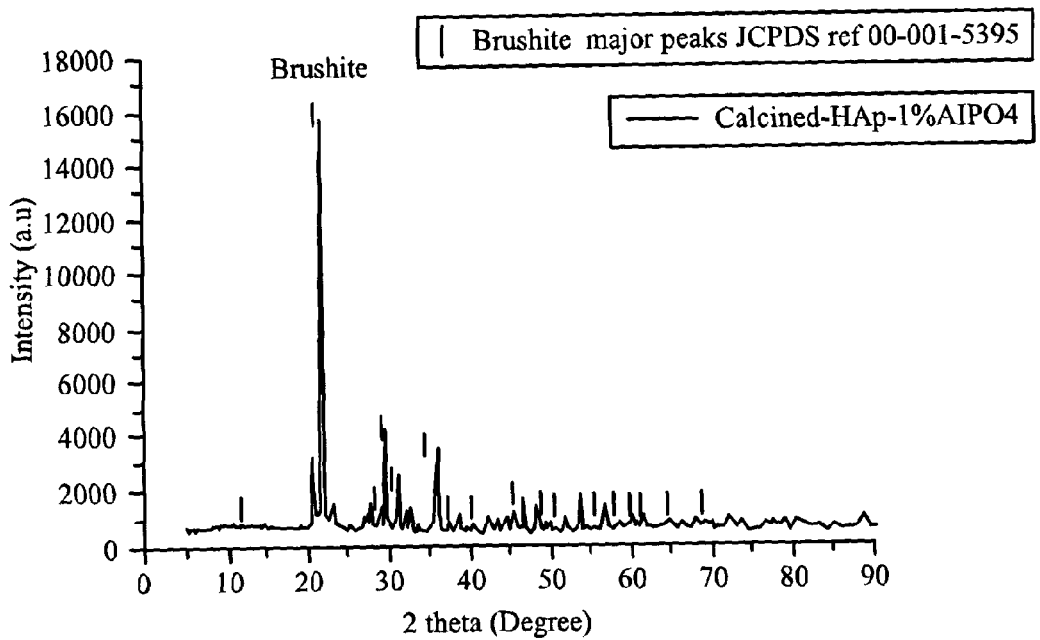
Figure 31:
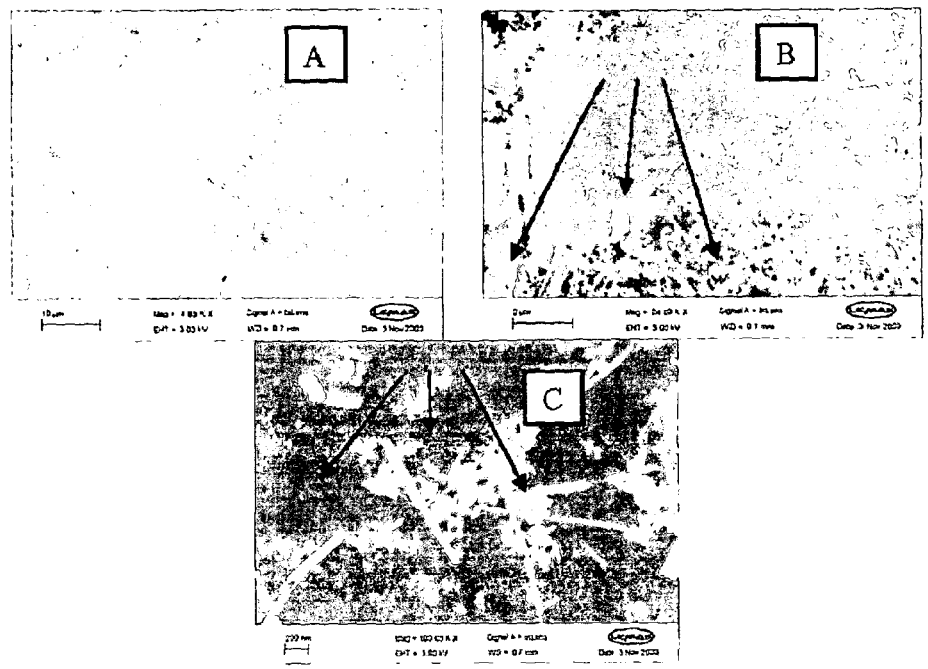
Figure 32:
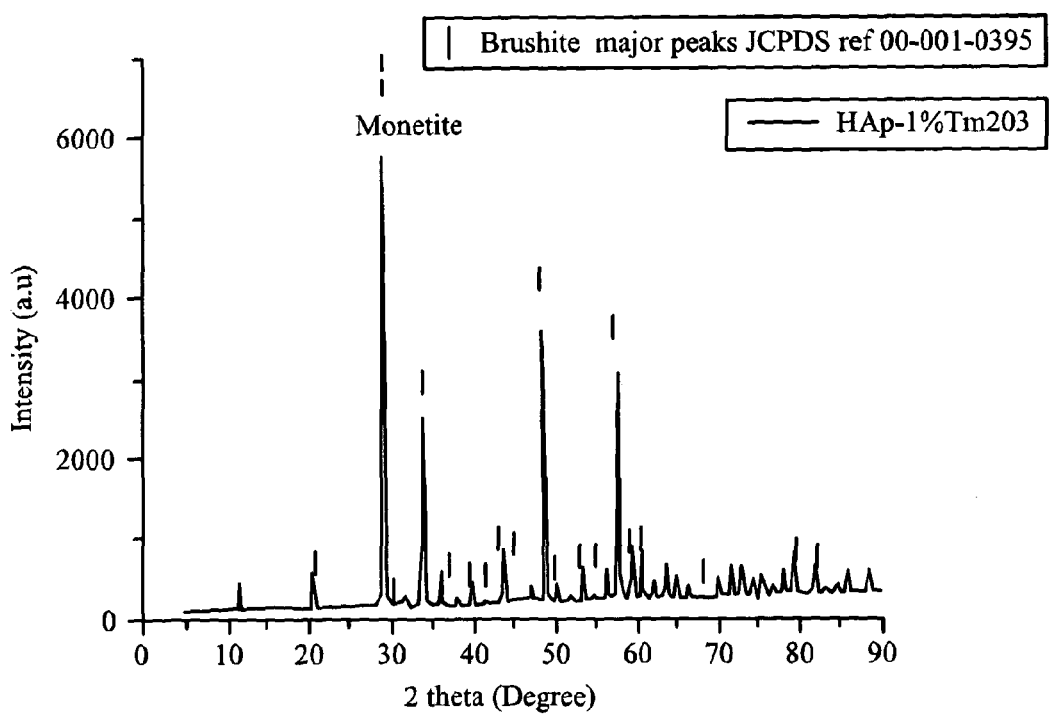
Figure 33:
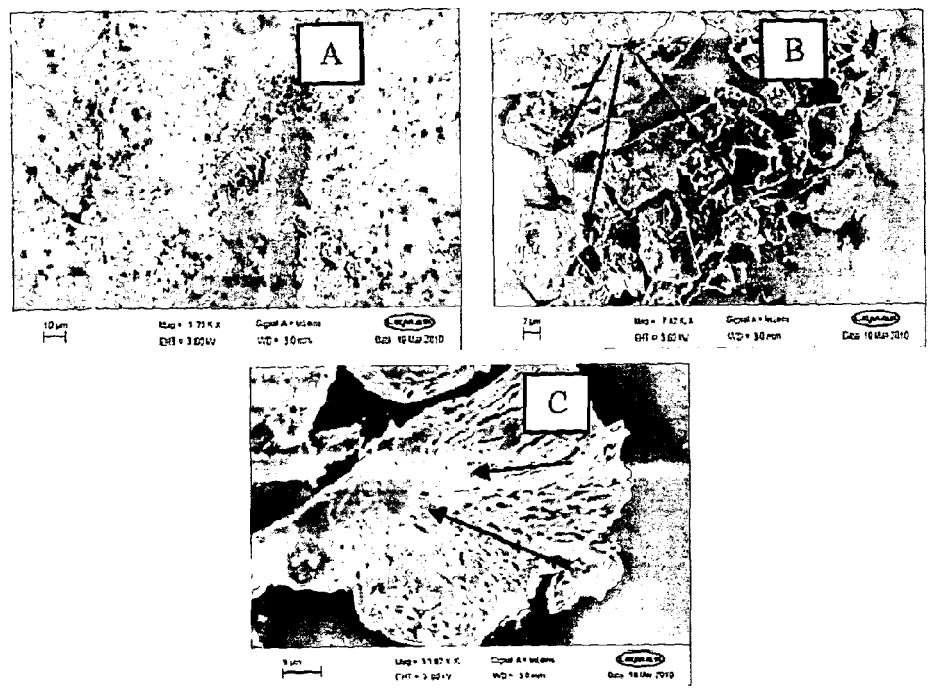
Figure 34:
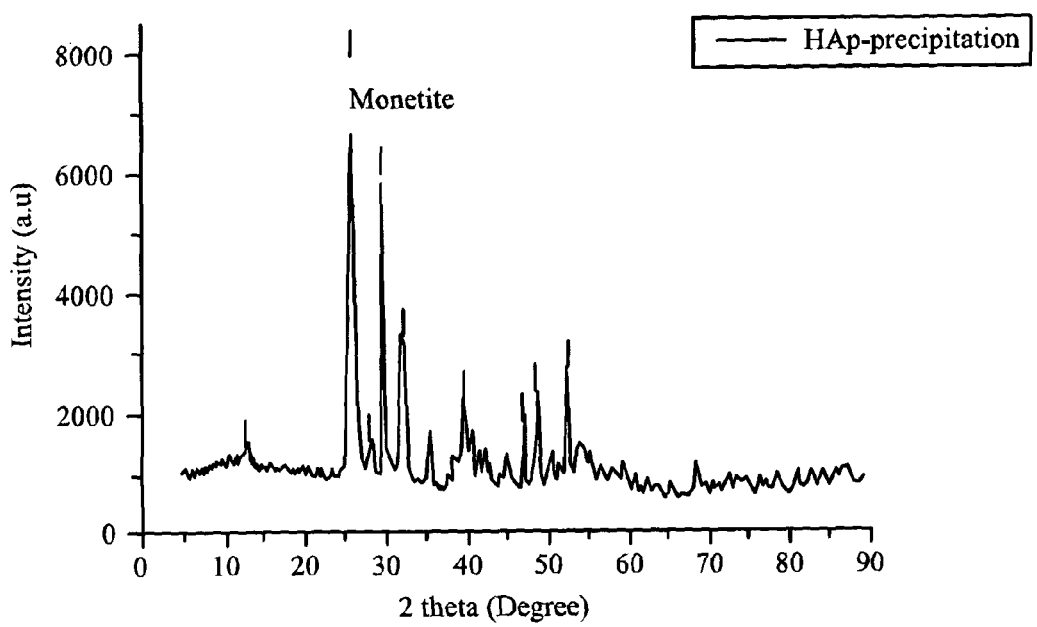
Figure 35:
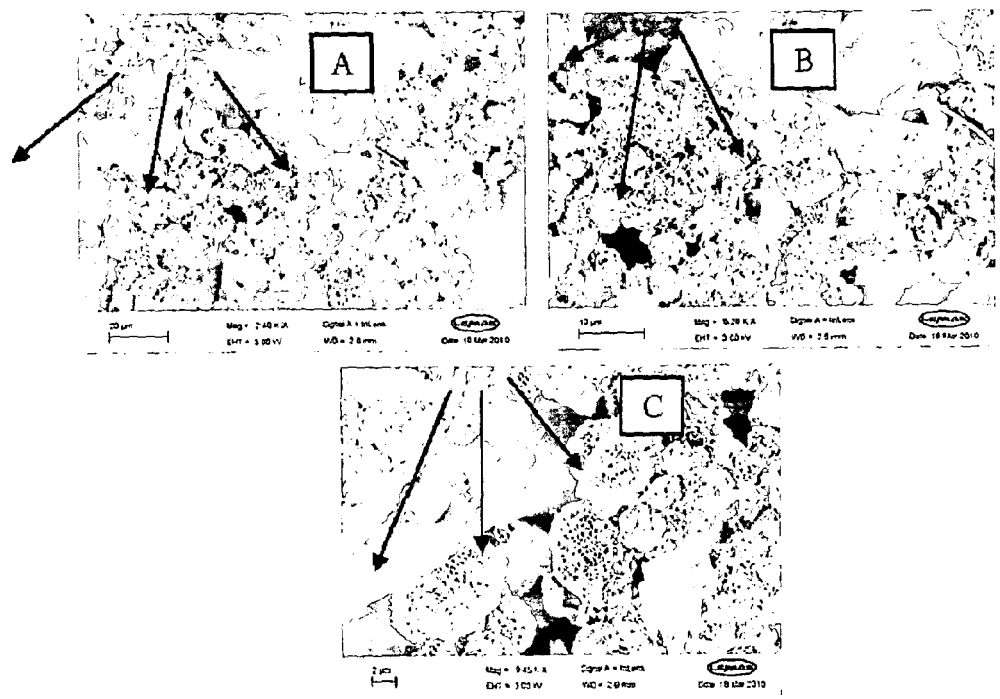
Figure 36:
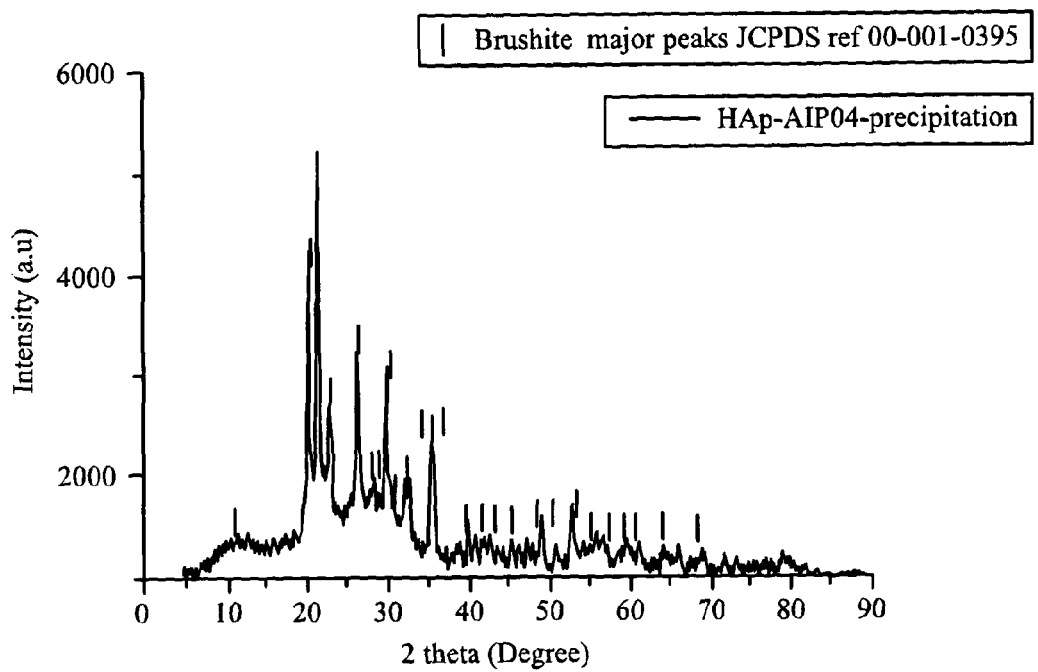
Figure 37:
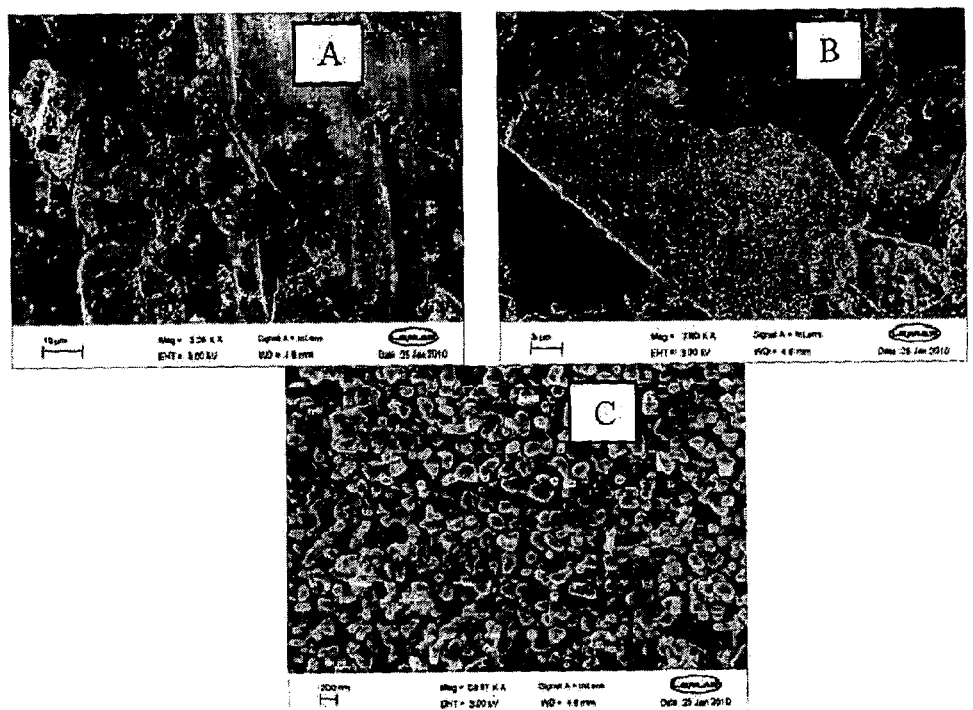
Figure 39:
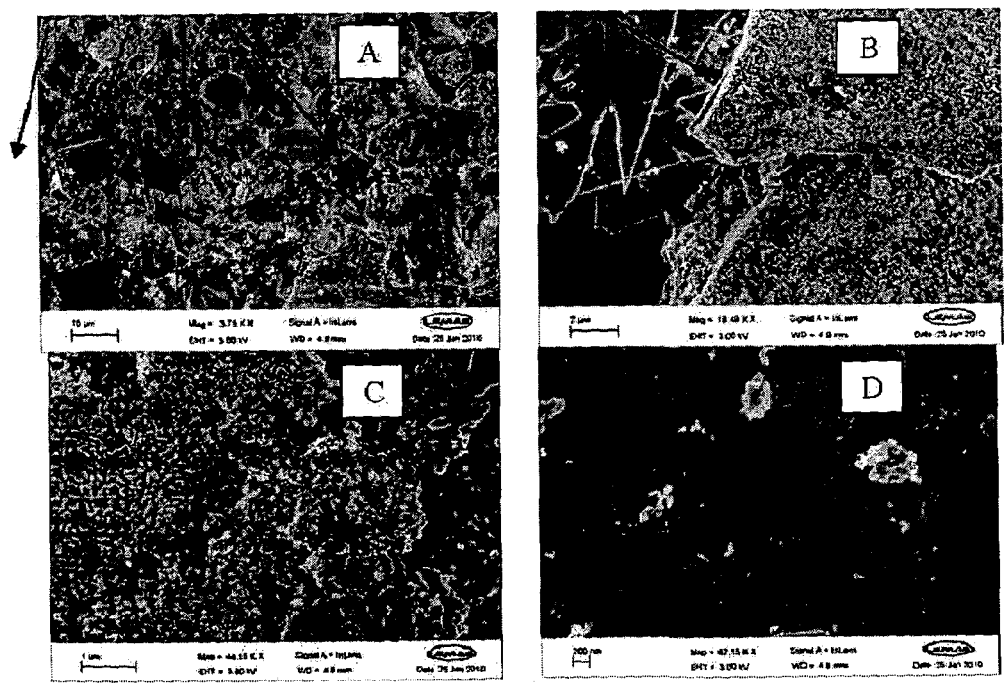
Figure 38:
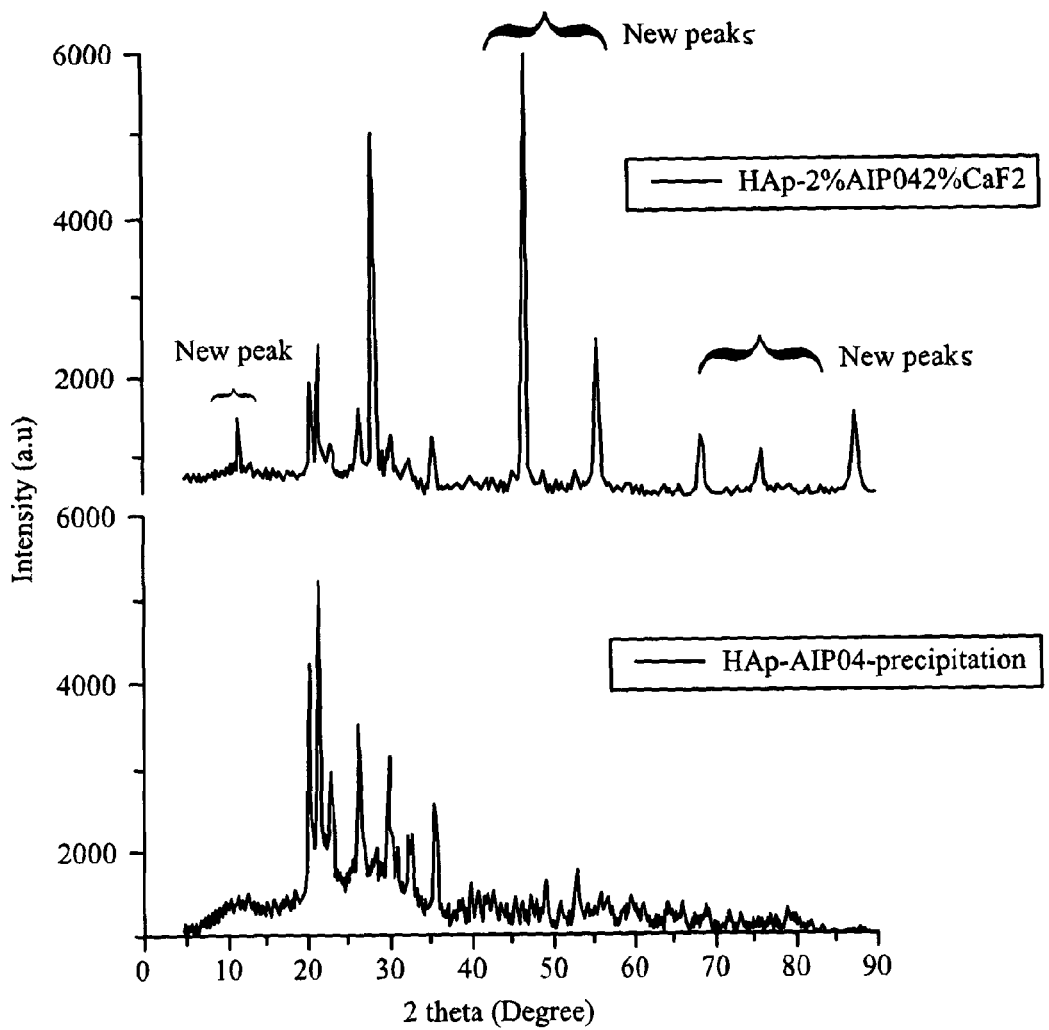
Figure 40:
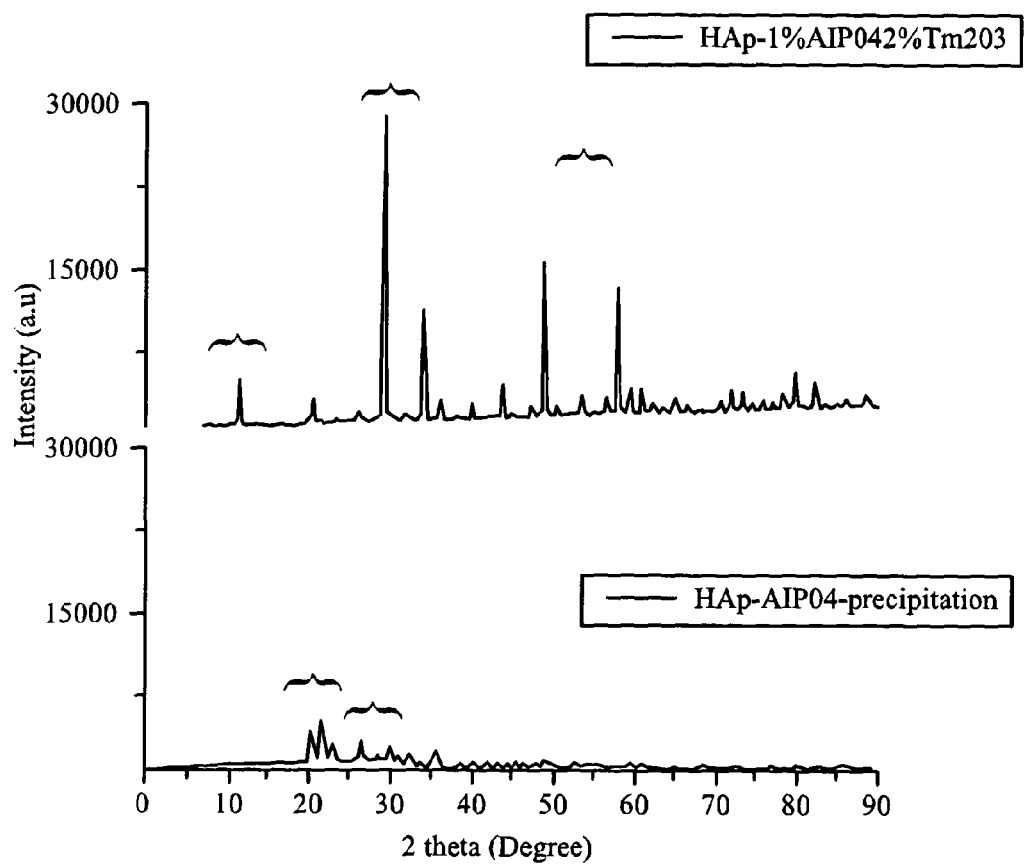
Figure 41:
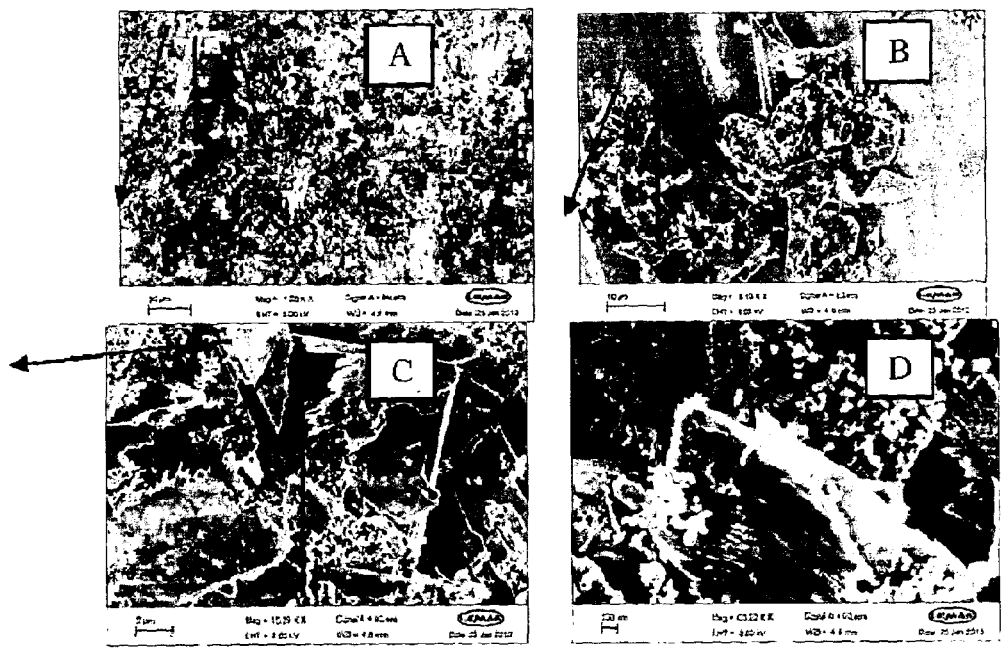
Figure 42:
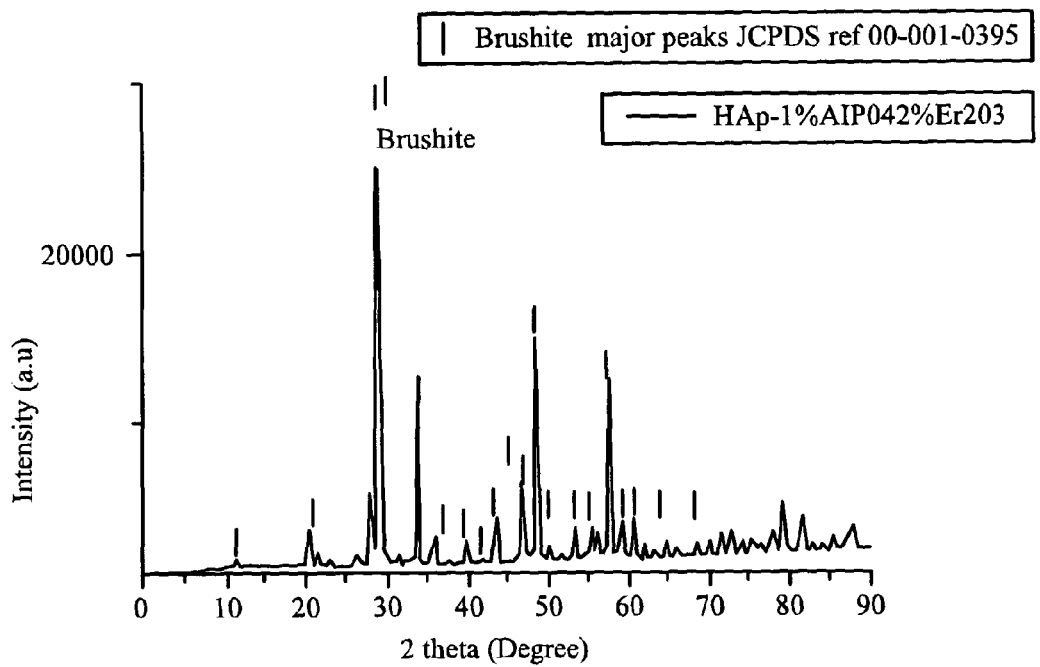
Figure 43:
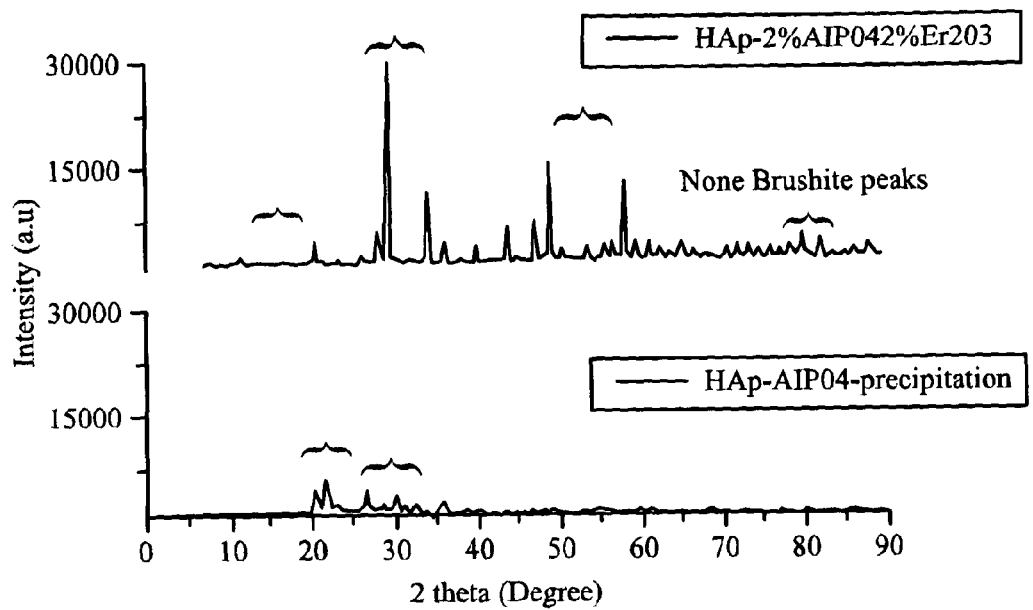
Figure 44:
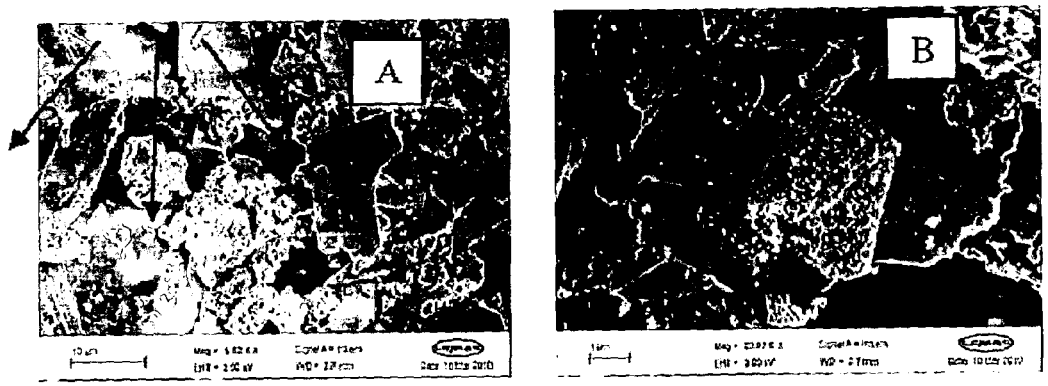
Figure 45:
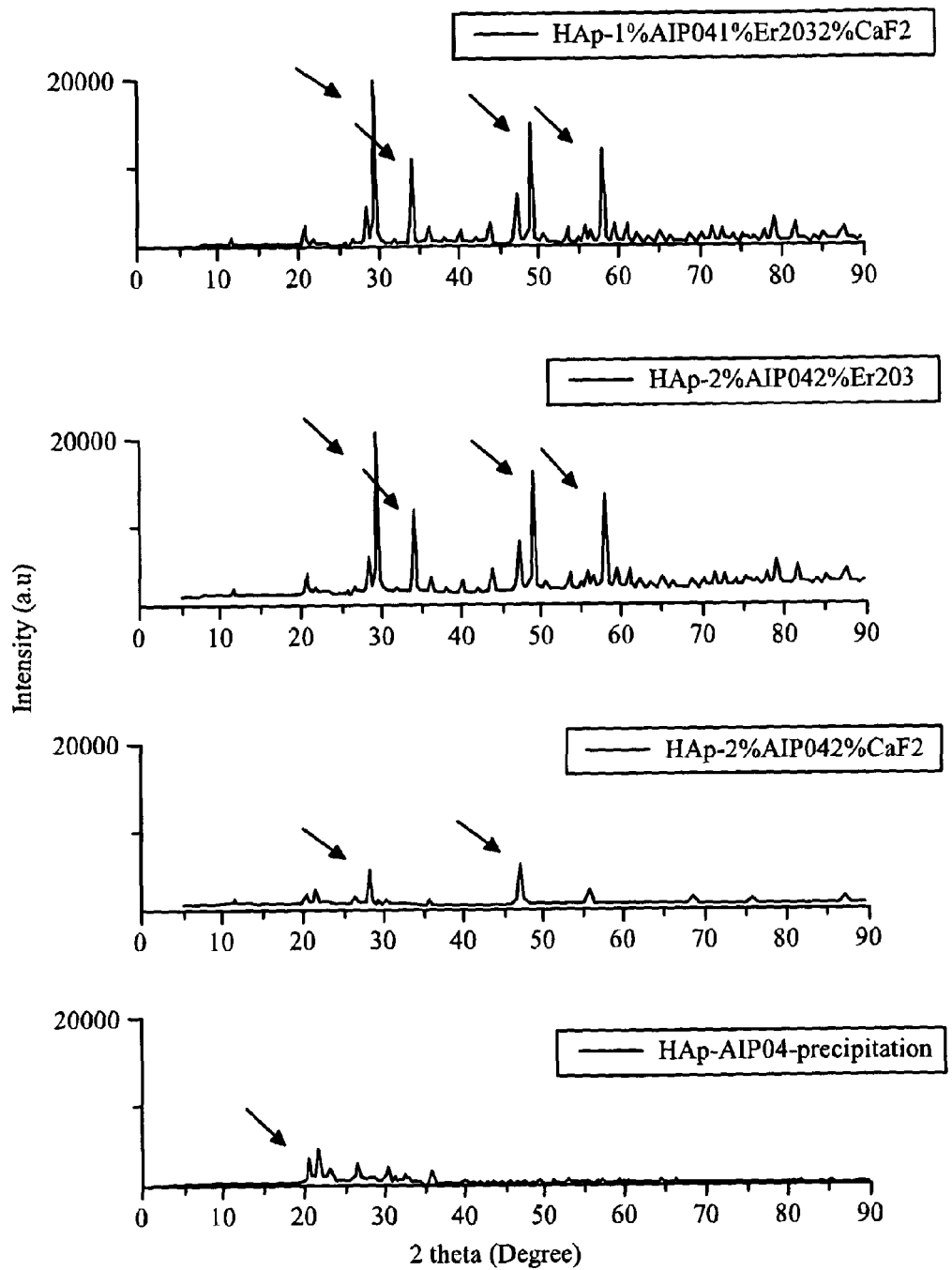
Figure 46:
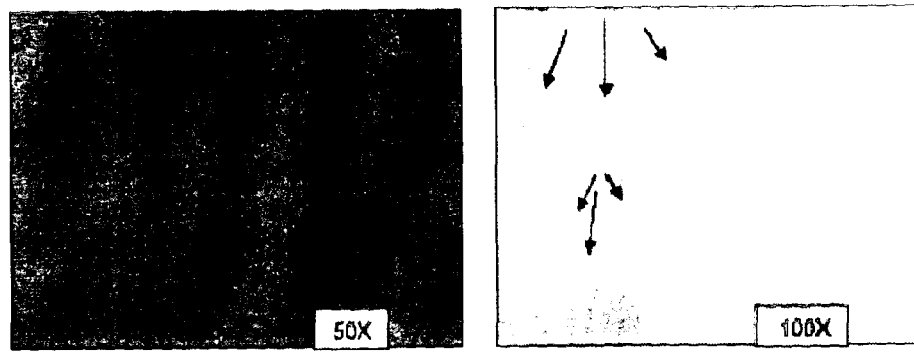
Figures 47, 48:
Figure 49:
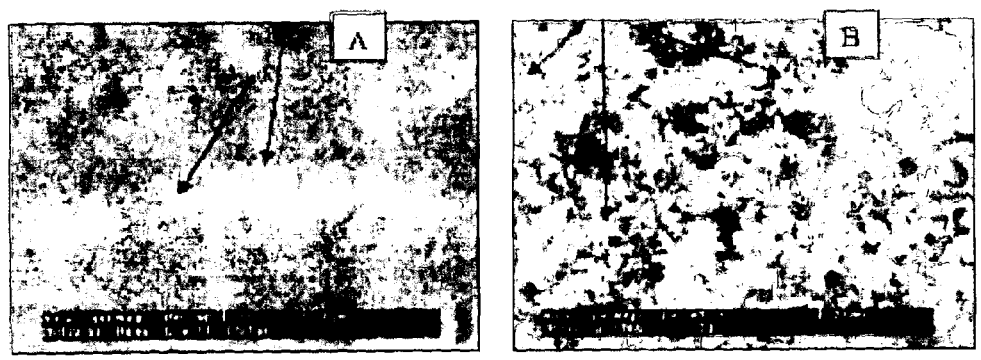
Figure 50:
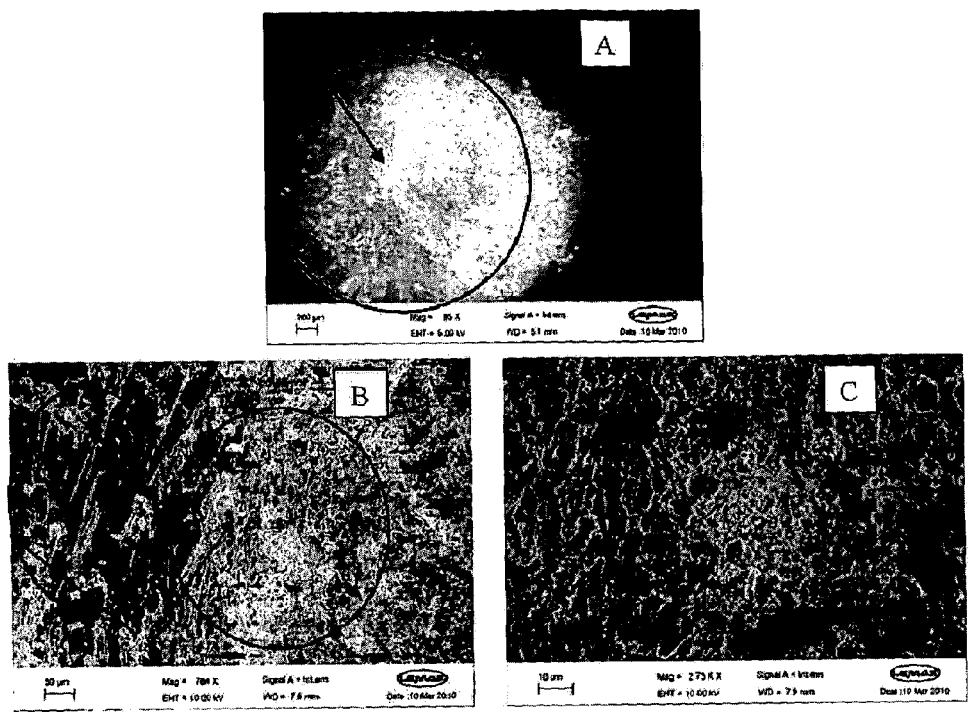
Figure 51:
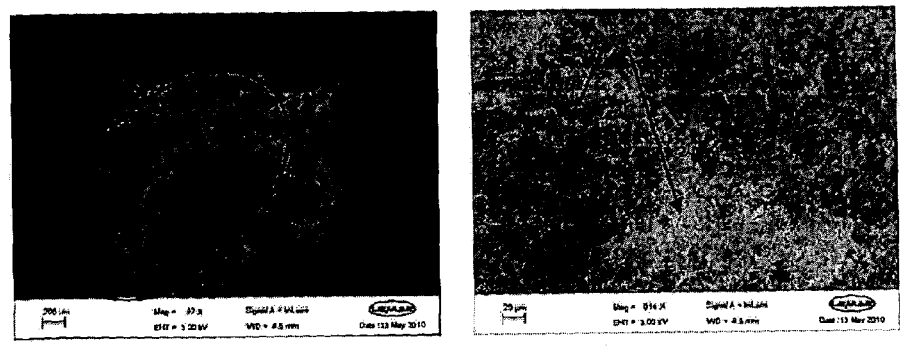
Figure 52:
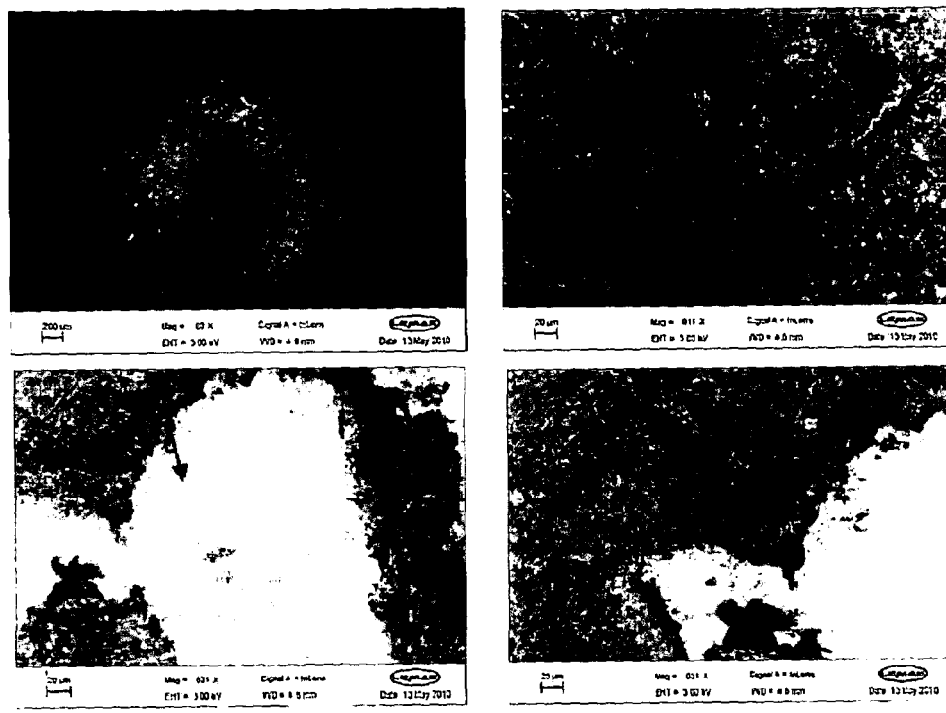
Figure 53:
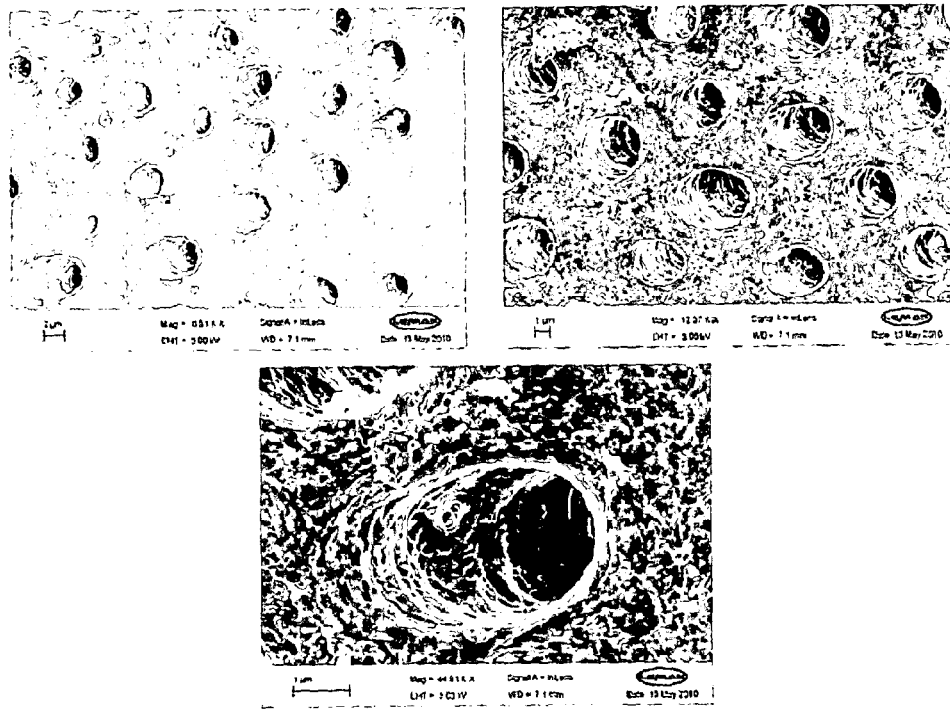
Figure 54:
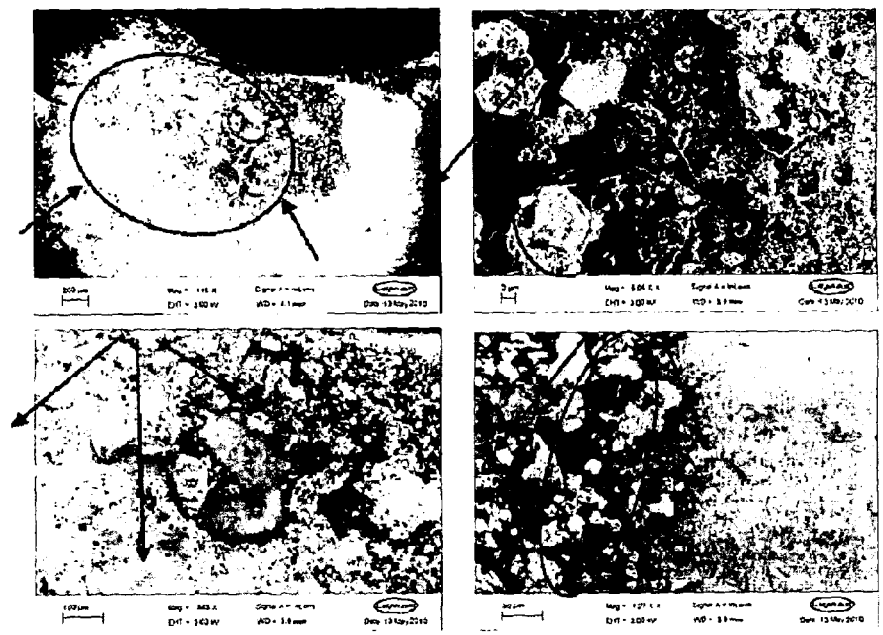
Figure 55:
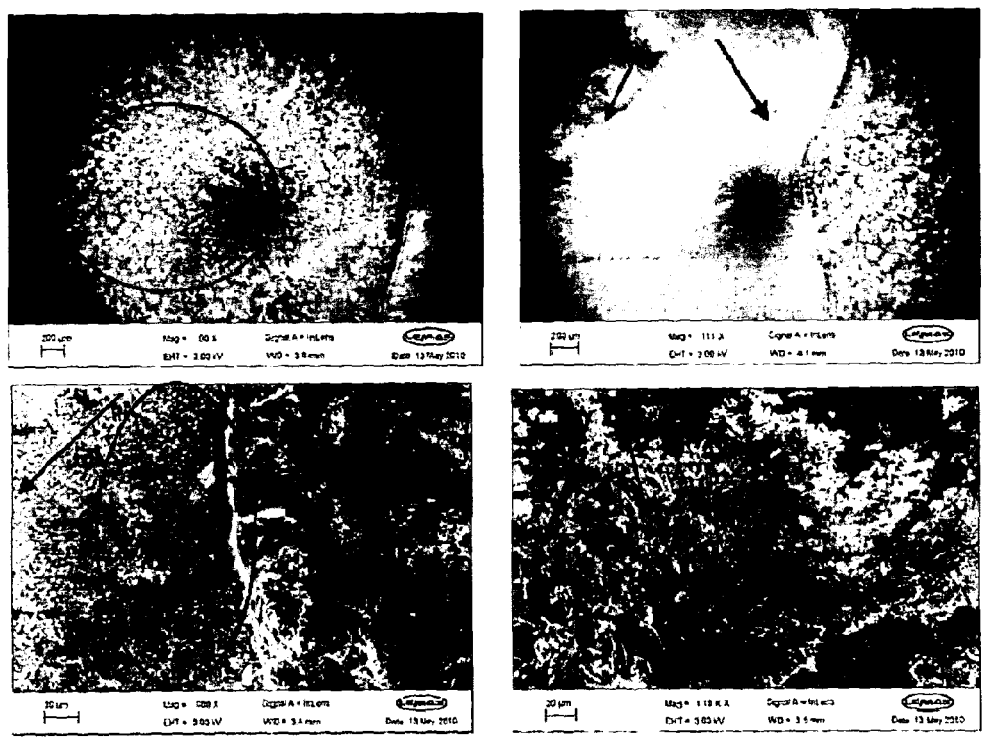
Figure 56:
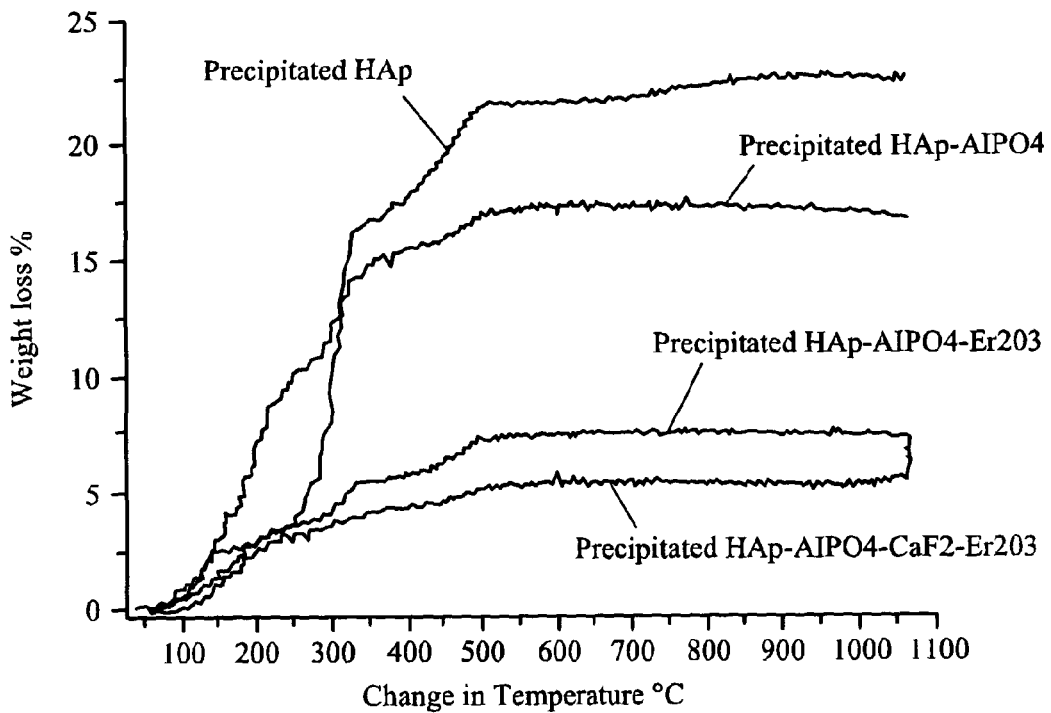
Figure 59:
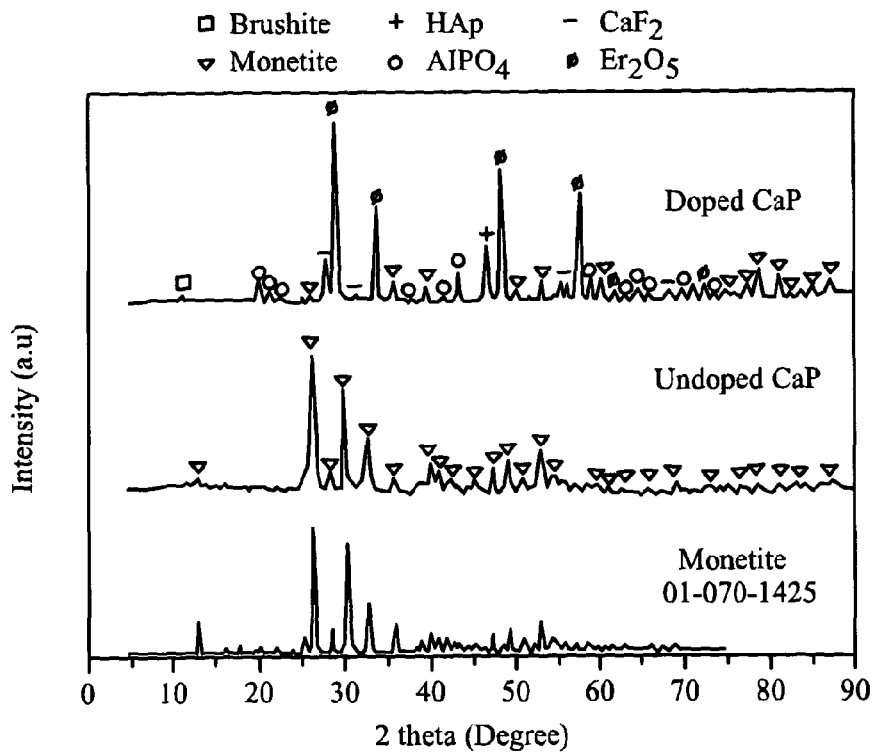
Figure 57:
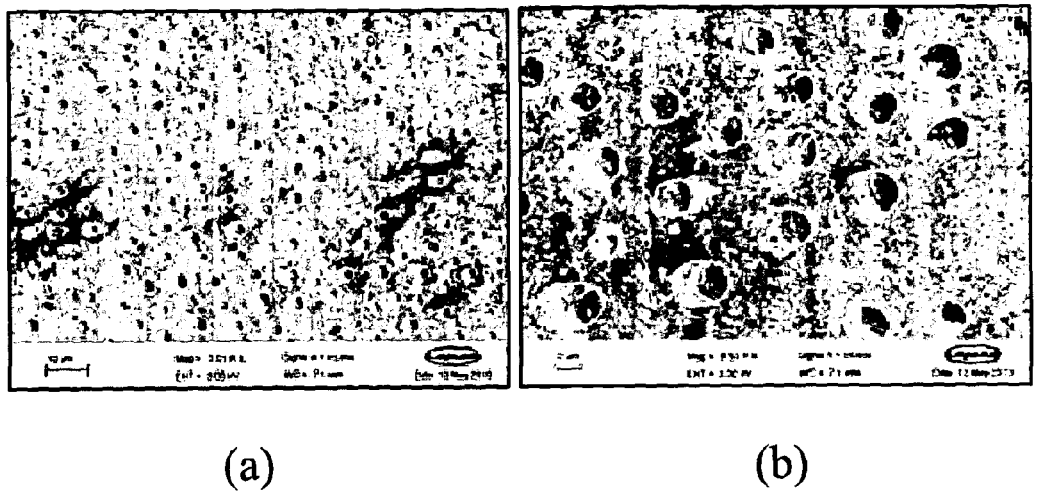
Figure 58:
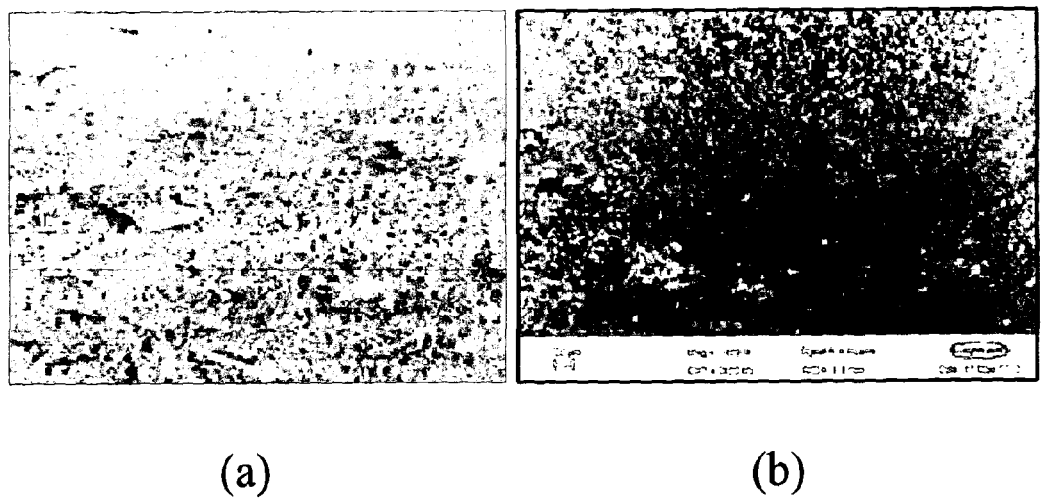
Figure 60:
Figure 61:
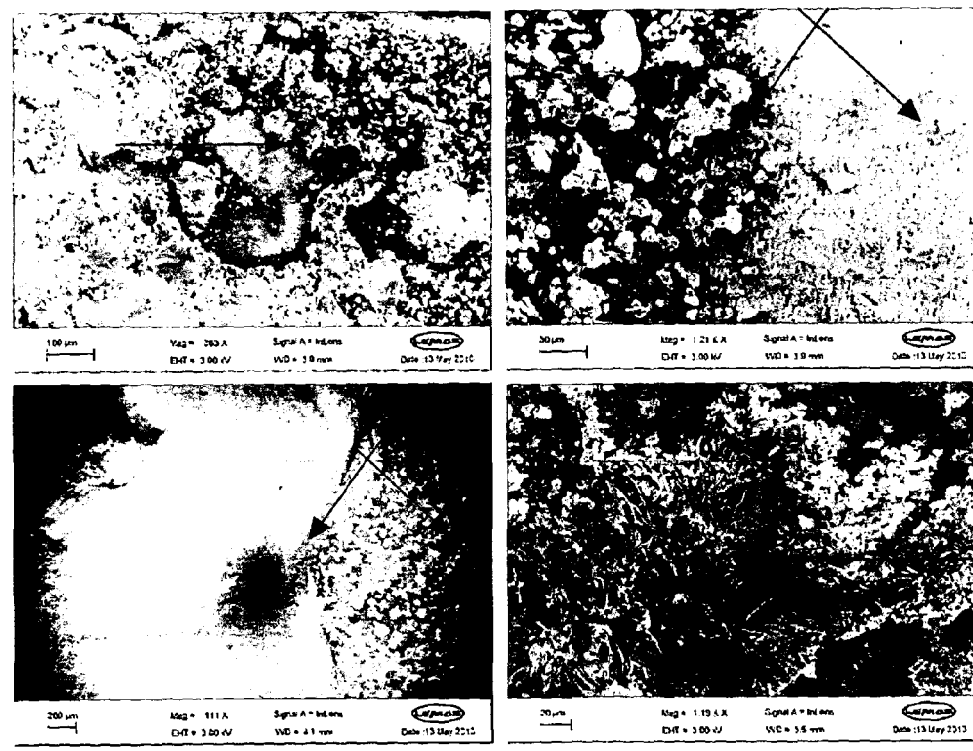
Figure 62:
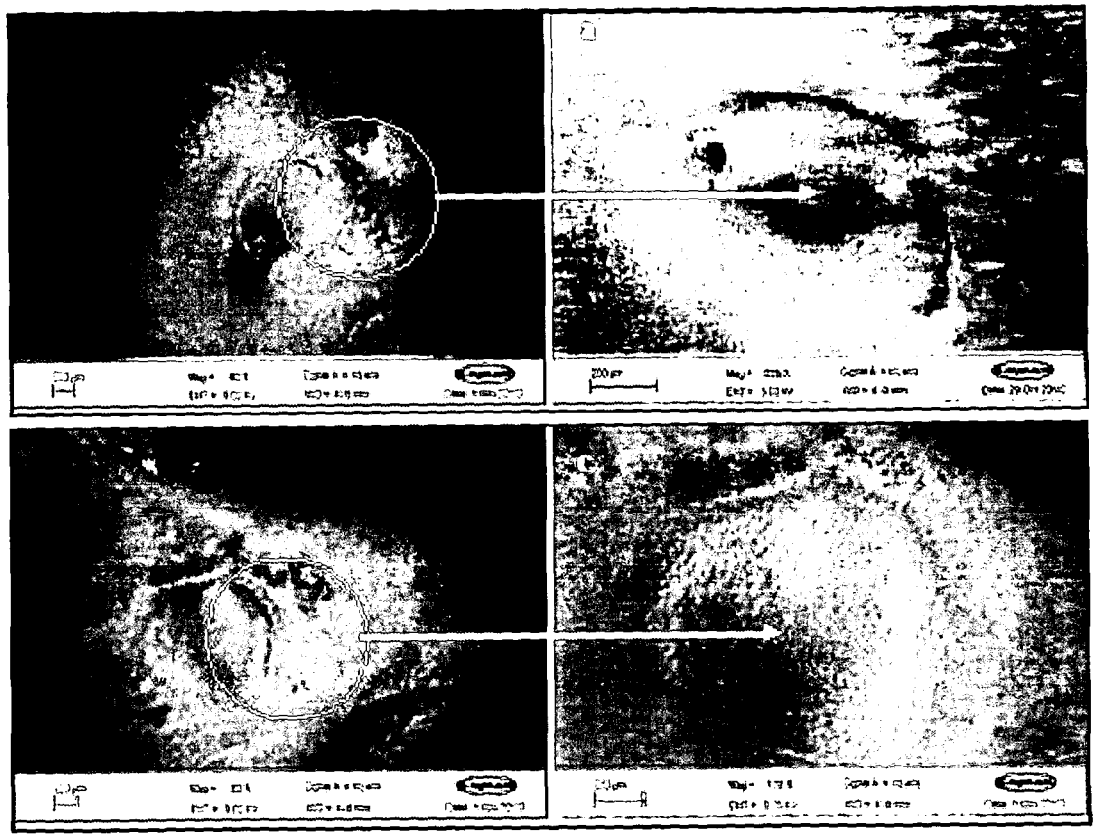
Figure 63:
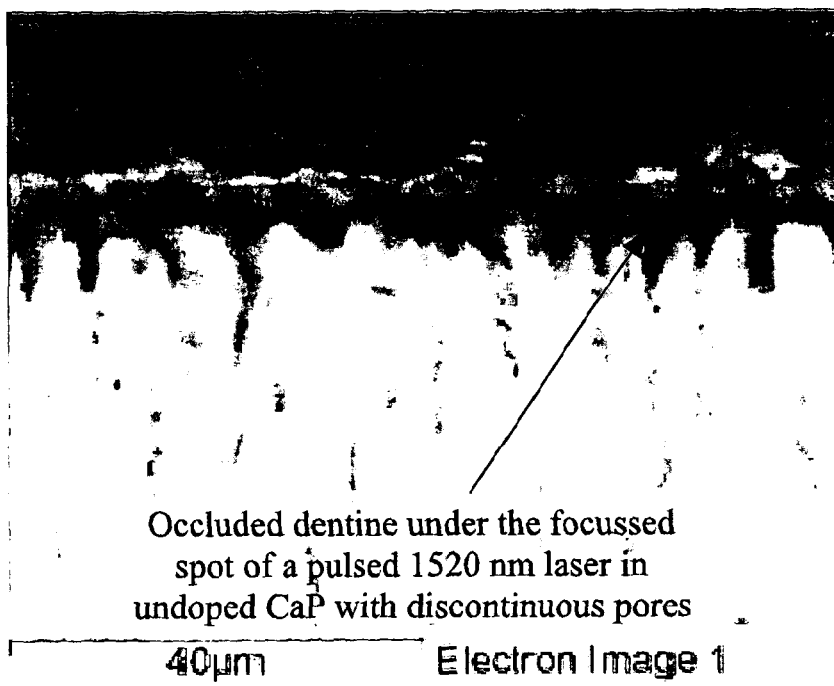
Figure 63:
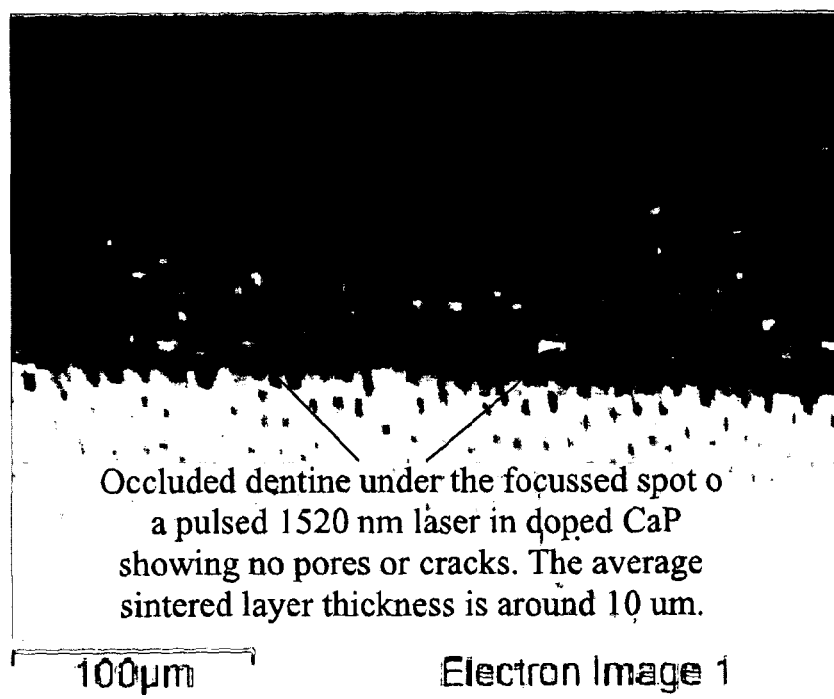

The present invention will now be described in a non-limitative sense with reference to Examples and the accompanying Figures in which:

FIG. 1: Schematic illustration of the structure of a tooth;

FIG. 2a: Predicted equilibrium phase composition in the Ca—Si—P—O—H system showing the presence of HAp and HAp with hydrated silica under atmospheric pressure conditions;

FIG. 2b: Predicted equilibrium phase composition in the Ca—La—F—P—O—H system;

FIG. 3: SEM micrographs of powders synthesized for 24 hrs at 200° C. from starting reaction slurries at (a) pH 5.1, (b) pH 8.0, (c) pH 10 and (d) pH 12;

FIG. 4: XRD patterns of powders prepared hydrothermally at 200° C. for (a) 24 hrs and (b) 48 hrs (marked peaks indicate $CaHPO_4$ and unmarked peaks indicate HAp);

FIG. 5: SEM image of a) nanosilica used for preliminary trials; (b) low and (c) high magnification images of dentine after infiltration with silica nanoparticles;

FIG. 6: Bar chart showing average particle length (left) and diameter (right) of HAp-containing particles synthesised from reaction slurries at pH 5.1-12;

FIG. 7: SEM micrographs of dentine treated with particles prepared at pH 12 ((a) Low magnification view showing frequency of tubule occlusion and (b) high magnification view indicating depth of infiltration below tubule opening);

FIG. 8: Coated tooth surface showing almost complete coverage of enamel with freshly prepared HAp-containing powder in ethanol (the accompanying EDX shows the presence of Ca, P and O elements);

FIG. 9a: A comparison of three different laser irradiated regions on the etched-face of human teeth coated with a nHAp-containing composition (laser specification 430 mW power, 135 fs pulse duration and 83 MHz repetition rate);

FIG. 9b: 30 second irradiation with laser specification 430 mW, 135 fs pulse duration and 83 MHz repetition rate;

FIG. 9c: 60 second irradiation with laser specification 430 mW, 135 fs pulse duration and 83 MHz repetition rate;

FIG. 9d: 120 second irradiation with laser specification 430 mW, 135 fs pulse duration and 83 MHz repetition rate;

FIG. 10: The hydrogen electrode potential (EH)-pH diagram for the synthesis of hydroxyl apatite with photo-activated lanthanide;

FIG. 11a: HAp-containing needles grown at 200° C. for 24 hours at pH 8;

FIGS. 11b and 11c: The microstructure of micrometer size HAp-containing needles and platelets grown at 140° C. and 80° C. respectively for 24 hours at pH 8;

FIG. 12: Coating over tubules exhibiting high surface coverage for treating hypersensitivity;

FIG. 13: FTIR analysis of nHAp-containing powder showing $Yb^{3+}$ ion absorption at around 1000 $cm^{-1}$, $OH^-$ first harmonic and fundamental bands at 1450 and 2900 $cm^{-1}$ respectively and the weak $Ho^{3+}$ band at around 1400 $cm^{-1}$;

FIG. 14: Fluorescence of a nHAp-containing composition excited with 980 nm laser diode exciting the $Ho^{3+}$ electronic states which emit at several wavelengths showing the effective absorption of photons and light emission;

FIGS. 15a-c: SEM micrographs of photoactivated Ho-doped nHAp-containing whiskers and crystals formed at 140° C. and pH 6, 9 and 14 respectively;

FIG. 16: Powders synthesized at 200° C. for 24 hrs at (A) an initial pH of 5.6 (B) an initial pH of 8 (C) an initial pH of 9 (D) an initial pH of 10 and (E) an initial pH of 11;

FIG. 17: Powder X-ray diffraction for HAp-containing powder prepared from pH 8 and 9 solutions by hydrothermal method at 200° C. for 24 hrs;

FIG. 18: Powder X-ray diffraction for HAp-containing powder prepared from pH 9 solutions by hydrothermal method at 200° C. for 24 hrs;

FIG. 19: Powder X-ray diffraction for HAp-containing powder prepared from pH 10 solutions by hydrothermal method at 200° C. for 24 hrs;

FIG. 20: Powder X-ray diffraction for HAp-containing powder prepared from pH 11 solutions by hydrothermal method at 200° C. for 24 hrs;

FIG. 21: HAp-containing powder synthesized at an initial pH of 5.6 at 80° C. for (A) 24 hrs (B) 48 hrs and (C) 72 hrs;

FIG. 22: HAp-containing powder synthesized at an initial pH of 5.6 at 200° C. for (A) 24 hrs and (B) 72 hrs;

FIG. 23: SEM of HAp-containing particles hydrothermally synthesized at 200° C. for 24 hrs after initial solutions were aged for (A) 2 weeks (B) 4 weeks and (C) 6 weeks;

FIG. 24: Powder X-ray diffraction for a HAp-containing composition prepared from solutions aged for 2 weeks and treated hydrothermally at 200° C. for 24 hrs;

FIG. 25: Powder X-ray diffraction for HAp-containing powders prepared from solutions aged for 2, 4 and 6 weeks and treated hydrothermally at 200° C. for 24 hrs;

FIG. 26: Powder X-ray diffraction for HAp-containing powders prepared hydrothermally at pH 10 at 200° C. for 24 hrs and by chemical precipitation at room temperature;

FIG. 27: HAp-containing powder synthesized at pH 10 (A) at 100° C. for 24 hrs (B) at 140° C. for 24 hrs (C) at 140° C. for 72 hrs and (D) at 200° C. for 24 hrs;

FIG. 28: SEM images for a composition containing HAp doped with 1 wt % aluminium phosphate and hydrothermally treated at 80° C. for 10 hrs ((A) and (B) show platelet morphology of particles while (C) and (D) show the process by which these platelets might have formed);

FIG. 29: Powder X-ray diffraction for a composition containing 1 wt % aluminium phosphate doped HAp prepared by hydrothermal method at 80° C. for 10 hrs;

FIG. 30: Powder X-ray diffraction for a powder containing 1 wt % aluminium phosphate doped HAp heated (calcined) from room temperature to 1000° C.;

FIG. 31: SEM images for a composition containing HAp doped with 1 wt % thulium oxide and hydrothermally treated at 80° C. for 10 hrs showing different particle size and shapes ranging from a short rod-like shape to platelets;

FIG. 32: Powder X-ray diffraction for a composition containing 1 wt % thulium oxide doped HAp prepared by hydrothermal method at 80° C. for 10 hrs;

FIG. 33: SEM images for a composition containing undoped HAp particles prepared by precipitation method at room temperature ((A) and (B) show platelet morphology of particles whilst (C) shows the process by which these platelets might have formed);

FIG. 34: Powder X-ray diffraction for an undoped HAp-containing powder prepared by precipitation method at room temperature;

FIG. 35: SEM images for a composition containing HAp doped with 1 wt % aluminium phosphate prepared by precipitation method at room temperature ((A) and (B) show platelet morphology of particles as well as a random agglomeration of some other particles (C));

FIG. 36: Powder X-ray diffraction for powder containing 1 wt % aluminium phosphate doped HAp prepared by precipitation method at room temperature;

FIG. 37: SEM images for a composition containing HAp doped with 2 wt % aluminium phosphate and 2 wt % calcium fluoride prepared by precipitation method at room temperature ((A) and (B) show platelet morphology of particles while (C) shows the process by which these platelets might have formed);

FIG. 38: Powder X-ray diffraction for a composition containing 2 wt % aluminium phosphate and 2 wt % calcium fluoride doped HAp compared with aluminium phosphate doped HAp;

FIG. 39: SEM images for a composition containing HAp doped with 1 wt % aluminum phosphate and 2 wt % thulium oxide prepared by precipitation method at room temperature ((A) and (B) show platelets morphology of particles while (C) and (D) show the process by which these platelets might have formed);

FIG. 40: Powder X-ray diffraction for a composition containing 1 wt % aluminium phosphate and 2 wt % thulium oxide doped HAp compared with a composition containing aluminium phosphate doped HAp;

FIG. 41: SEM images for a composition containing HAp doped with 2 wt % aluminum phosphate and 2 wt % erbium oxide prepared by precipitation method at room temperature ((A) and (B) show platelet morphology of particles while (C) and (D) show the process by which these platelets might have formed);

FIG. 42: Powder X-ray diffraction for a powder containing 2 wt % aluminium phosphate and 2 wt % erbium oxide doped HAp prepared by precipitation method at room temperature;

FIG. 43: Powder X-ray diffraction for a composition containing 1 wt % aluminium phosphate and 2 wt % thulium oxide doped HAp compared with a composition containing aluminium phosphate doped HAp;

FIG. 44: SEM images for a composition containing HAp doped with 2 wt % aluminum phosphate, 1 wt % erbium oxide and 2 wt % calcium fluoride prepared by precipitation method at room temperature ((A) and (B) show platelets and a random agglomeration of other particles);

FIG. 45: Powder X-ray diffraction of powders containing aluminium phosphate, erbium oxide and calcium fluoride doped HAp precipitated at room temperatures;

FIG. 46: Optical microscopy of a tooth section coated with a composition containing aluminium phosphate doped HAp after a single dip coating. The final image magnification is determined by both the magnification of the objective and the eye-piece (10×);

FIG. 47: SEM images of a tooth section coated with HAp after only a single dip coating;

FIG. 48: SEM images of a tooth section coated with a composition containing $AlPO_4$—$CaF_2$—$Er_2O_3$ doped HAp after a single dip coating;

FIG. 49: ESEM images of a tooth section coated with a composition containing HAp-$AlPO_4$ after a single dip coating (A) without Pt coating (B) with Pt coating. The Pt coating is not for dental enamel but for enhancing the image contrast during microscopic examination in the electron microscope;

FIG. 50: SEM images of pellets of ~2 mm thickness containing thulium oxide doped HAp subjected to 1550 nm pulsed laser showing the sintered area and the change in surface morphology;

FIG. 51: SEM images of pellets of ~2 mm thickness containing aluminium phosphate-calcium fluoride-erbium oxide doped HAp subjected to 980 nm CW laser showing the sintered area and the change in surface morphology;

FIG. 52: SEM images of pellets of ~2 mm thickness containing calcium fluoride doped HAp subjected to 980 nm CW laser showing the sintered area and the change in surface morphology;

FIG. 53: SEM images of an as-prepared tooth section of ~2 mm thickness subjected to 980 nm CW laser showing the surface morphology but no observed laser sintered area;

FIG. 54: SEM images of a tooth section of ~2 mm thickness coated with particles containing undoped HAp and subjected to 980 nm CW laser showing the sintered area and the change in surface morphology of HAp and the sealing of dentinal tubules;

FIG. 55: SEM images of a tooth section of ~2 mm thickness coated with particles containing aluminium phosphate-calcium fluoride-erbium oxide doped HAp and subjected to 980 nm CW laser showing the sintered area and the change in surface morphology by crystal growth and the occlusion of a large area of dentinal tubules;

FIG. 56: The rates of % weight loss versus temperature for the mineral compositions listed in the inset;

FIG. 57: a) A low magnification (scale bar represents 10 µm) SEM image of dentine cross-section etched with 35% v/w phosphoric acid to expose the dentinal tubules microchannels which mimic natural dentine hypersensitivity and b) a 10 times magnified SEM image (scale bar represents 2 µm) showing an average of 1 µm size tubule opening;

FIG. 58: SEM images of tooth sections coated with (a) undoped CaP mineral compositions and (b) doped CaP mineral compositions for 20 seconds. The occlusion of dental tubules is shown with a 20 µm scale bar for each image;

FIG. 59: A comparison of X-Ray powder diffraction data for undoped CaP mineral compositions and doped CaP mineral compositions. The undoped CaP mineral composition shows the presence of monetite whereas the doped CaP mineral composition includes a mixture of monetite, brushite, HAp and undissolved dopants $Er_2O_3$, $AlPO_4$ and $CaF_2$;

FIG. 60: SEM images of platelet-like particles of (a) an undoped CaP mineral composition and (b) a doped CaP mineral composition prepared by the chemical precipitation method at room temperature;

FIG. 61: SEM images of tooth cross-sections coated with an undoped CaP mineral composition and a CaP mineral composition doped with $Er_2O_3$, $AlPO_4$ and $CaF_2$ dopants after treatment with a 980 nm CW laser for 5 minutes: a) showing localisation of melting in the centre of the spot and fragmentation, b) depicting the fragmented CaP droplets on the left of CaP coated dentine representing a poor and non uniform densification, c) showing uniform melting and coalescence in the wake of fragmented droplets and d) showing in the centre the re-crystallized rosette revealing the non-uniform formation of crystal surrounded by exposed dental tubules. Overall surface coverage with the doped CaP mineral composition shown in FIGS. 61c and 61d appears superior to the surface coverage in the undoped CaP mineral composition shown in FIGS. 61a and 61b;

FIG. 62: SEM images of tooth sections coated with a doped CaP mineral composition after being irradiated with 1520 nm pulsed laser irradiation. FIGS. 62a-b represent areas irradiated for 2 minutes showing the crater surrounded by a wave-like feature and a distortion in the coating causing a crack. FIGS. 62c-d represent areas irradiated for 30 seconds showing the crater surrounded by a wave-like feature without any distortion in the coating which could be beneficial in achieving a uniform densification of the CaP layer over the dentine micro channels;

FIG. 63: Cross-sectional SEM of pulsed laser sintered tooth sections with a) a coating of an undoped CaP mineral composition and b) a coating of a doped CaP mineral composition. The overlayer appears less sintered but the tubule occlusion appears quite uniform with doped CaP mineral composition when compared with undoped CaP mineral composition; and FIG. 64: Thermogravimetric analysis measurements of undoped and doped CaP mineral compositions showing the weight loss percentages and the effect of $Er_2O_3$, $AlPO_4$ and $CaF_2$ on thermal stability.

EXAMPLE 1

In Vitro Experimental Methods i) Preparation of a Hypersensitive Surface

Standard dentine sections for in-vitro trials were prepared from clinically extracted human molars. Between extraction and sectioning, the teeth were stored in saline solution at about 4° C. Discs of thickness about 1 mm were cut from a region beneath the enamel dentine junction using a water-cooled diamond-coated cutting wheel. After sectioning, the dentine samples were polished on wet 2500 grit SiC paper to remove grinding marks and washed by means of an ultrasonic bath in distilled water. Etching was then carried out with a 37 vol % phosphoric acid solution for 60 s to remove the natural smear layer. This was followed by a final wash with distilled water under ultrasonic agitation. The discs were then dehydrated progressively by treatment with graded alcohol/water mixtures and finally by treatment in absolute alcohol. This minimised any tissue shrinkage due to direct exposure to alcohol. Samples were then left to dry in air before being transferred to a desiccator and stored under reduced pressure for 24 hours at 20° C. The resultant sections simulate the surface of naturally exposed dentine characteristic of extreme cases of dentine hypersensitivity (see FIG. 1). Sections prepared in this way were used for all particle infiltration trials.

ii) Synthesis of Nanoparticles

A commercially available colloidal silica powder in aqueous suspension comprising 40 nm diameter spherical nanoparticles (Sigma Aldrich, LUDOX® TM-40, 40 wt % in water) was used in initial 'proof-of-principle' trials. The nanoparticle suspensions as received (Fisher Scientific 99.9% Biotech grade) were diluted in methanol to take advantage of the drying qualities of alcohol. The diluted suspensions were prepared by mixing the aqueous silica suspension with methanol in the appropriate quantities to give a loading of about 0.05 volume weight percent (v/w %). This was applied dropwise to the exposed tubules in the prepared dentine disc. Each silica suspension was treated ultrasonically for 5 minutes immediately prior to application. After application, the samples were left to dry in air before drying for a further 24 hours under reduced pressure in a desiccator.

For the hydrothermal synthesis of a mineral composition containing nHAp [$Ca_{10}(PO_4)_6(OH)_2$], 1.0M stock solutions were prepared by dissolving calcium nitrate tetrahydrate ($Ca(NO_3)_2 \cdot 4H_2O$ Fisher Scientific ACS grade) and diammonium hydrogen phosphate (($NH_4)_2HPO_4$ Fisher Scientific, ACS grade) in distilled water (see Pashley et al [supra]). The stock solutions were diluted to 0.1M with distilled water and subsequently mixed by the dropwise addition of the phosphate solution to the calcium solution to yield suspensions with a Ca/P molar ratio of 1.67 corresponding to that of hydroxyapatite. The pH of the mixed suspension was 5.1. The pH was adjusted in the range 5.1 to 12.0 by dropwise addition of concentrated (about 17 M) ammonium hydroxide solution (Fisher Scientific, analytical grade) to control particulate growth.

The suspensions were either transferred to a 125 ml capacity Teflon-lined hydrothermal reactor (Model 4748, Parr Instrument) or placed in a larger 1.6 liter capacity vessel (Model 4570, Parr Instrument). Reactions were carried out over a period of 3 to 72 hours at temperatures between 100° C. and 350° C. The products underwent a thorough wash cycle involving high speed centrifugal sedimentation (6000 rpm) for 5 minutes followed by decanting the supernatant and re-suspending the powder in distilled water via vigorous shaking and agitation using an ultrasonic bath (5 minutes). This cycle was repeated 6 times and the pH of the suspension was monitored using a pH meter (Metier Toledo MP225 pH meter with InLab® 413 electrode). A final wash was performed using methanol (Fisher Scientific 99.9% Biotech grade) to limit agglomeration of the particles. After the final wash and centrifuge cycle in methanol, the supernatant was decanted and the wet sediment was collected, weighed and used for re-suspension at about 0.5 wt %.

Phase analysis of the samples was performed using a Philips X-ray diffractometer in the range 5-70° 2θ at a scan speed of 0.05° $s^{-1}$. Particle size and morphology were determined using field emission scanning electron microscopy (LEO 1530 FEGSEM) at 3 kV with a working distance of 3 mm and further high-resolution analysis by transmission electron microscopy (Phillips CM200 FEGTEM). For each powder batch, 200 particles were measured (length and diameter) and the particle size distribution was plotted.

iii) Trials

Proof-of-principle trials using nanosilica particles to infiltrate and occlude dentine tubules were carried out. The effectiveness of the treatment in blocking the dentinal tubules was investigated using SEM imaging of the central region of each specimen (see FIG. 5).

Before the HAp-containing mineral composition was used to infiltrate dentine tubules, initial trials were carried out to find suitable liquid dispersion media and a surfactant for obtaining a deflocculated suspension during sedimentation. Acetone, distilled water, isopropanol, ethanol, methanol and a 1 wt % solution of sodium metaphosphate [$NaPO_3]_n$ in distilled water were considered.

An etched face of a tooth coated with a layer of nHAp-containing mineral composition (see FIG. 8) was used for a laser irradiation trial to demonstrate that at a non-resonant (no molecular or electronic absorption) wavelength of a femtosecond pulsed laser, the layer can be partially sintered.

The equilibrium diagrams in FIGS. 2a and 2b demonstrate how lanthanide ions can be incorporated into the mineral compositions and whether the incorporation of lanthanide ions yields a thermodynamically stable phase composition. FIG. 2a shows the phase composition with Si which then yields hydrated silica in combination with HAp. FIG. 2b illustrates how F ions in the presence of lanthanum oxide yield a beneficial combination of $LaF_3$, $La_2O_3$ and HAp. The equilibrium conditions demonstrate that rare-earth ions other than lanthanum can be incorporated from the solution phase under hydrothermal processing conditions.

Results and Discussion

SEM imaging of dentine sections after infiltration by nanosilica particles indicated that at least 50% of the tubules were significantly occluded after only one application of the nanoparticles in a dilute (about 0.5 w/v %) suspension in methanol (see FIG. 5b). An indication of the degree of tubule occlusion and depth of particle infiltration was shown by higher magnification imaging of the same sample (see FIG. 5c). Estimates of the depth of infiltration made by tilting the sample stage whilst imaging suggested that the particles were at least 1-3 μm below the tubule opening and possibly deeper. Particle agglomerates had formed during drying and had effectively occluded the tubules.

From initial preliminary results, a hydrothermal reaction temperature of 200° C. was deemed to be the most appropriate for producing crystalline HAp. This was subsequently adopted as the standard temperature for the investigation of reaction time and pH on the particle properties. Treatment times of 3, 12, 18, 24, 48 and 72 hours were investigated for a stock suspension at a pH of 5.1. XRD patterns of the powders after reaction times of 3-12 hours indicated the presence of secondary phases together with the desired HAp phase. Very faint peaks from secondary phases were still evident at 18 hours but a single-phase HAp pattern was obtained on increasing the reaction period to 24 hours (see FIG. 4a). Powders synthesised for longer treatment times 48 and 72 hours (FIG. 4b) indicated the presence of another secondary phase attributed to the mineral monetite ($CaHPO_4$). On this basis, a treatment time of 24 hours was selected as the most favourable reaction period for producing HAp-containing powders at 200° C.

An SEM image showing the rod-shape morphology of the HAp derived from the solution at pH 5.1 after 24 hours is shown in FIG. 3a. Rod lengths varied over a wide range (about 100-600 nm) but there was less variation in particle width (about 30-50 nm). The average length and width from a count of 200 particles was 370 nm and 40 nm respectively Attempts were made to try to synthesise particles less elongated than those shown in FIG. 3a to achieve morphological characteristics similar to those of silica (shown in FIG. 5c). Increasing the pH from 5.1 to 8.0 resulted in a small decrease in mean particle length to about 320 nm and a reduction in diameter to about 30 nm (see FIG. 3b). At pH 10, average particle length was significantly lower (110 nm) but with a similar diameter to pH 8 particles (about 30 nm see FIG. 3c). Increasing the pH to 12 resulted in particles with an average length of 70 nm and diameter of 30 nm (see FIG. 3d). This was the least elongated of the synthesised rods but still far from equiaxed. The variation in particle length for the sample prepared at pH 12 was 30-145 nm and in diameter was 25-35 nm. The average length and width for all of the starting suspensions is shown in FIG. 6 which highlights that the most significant change in particle properties (length) occurred between pH 8 and pH 10. Aspect ratios (average length/diameter) were:

9-10 for powders prepared from suspensions at pH 5.1 to 8 3.8 for powders prepared from a suspension at pH 10 and 2.4 for powders prepared from a suspension at pH 12.

The particles produced at pH 12 were selected for dentine infiltration trials.

Experiments were carried out to determine the most effective dispersion medium for the particles which would be compatible with any future in vivo applications. The latter consideration restricted the pH range and the composition of stabilising agents used. Distilled water with 1 wt % sodium metaphosphate, methanol and ethanol were promising. Most in vitro experiments were conducted using methanol but ethanol may be the preferred choice for future in vivo applications. Some of the experiments described below using methanol were repeated using ethanol as the dispersion medium and the results were comparable. Based on the nanosilica infiltration trials, methanol suspensions were prepared with a solids loading of 0.5 wt %.

The effectiveness of the suspensions in blocking dentinal tubules was investigated using the protocol outlined above for silica. The infiltration results from suspensions of the particles at pH 12 are shown in FIG. 7. Particles (or more specifically agglomerates) of the individual primary nanoparticles penetrated most of the tubule openings and were observed to be located below the surface of the dentine section in a similar manner to the silica trials (see FIG. 5). A survey of many low magnification SEM images indicated that after a single treatment of the 0.5 wt % suspension, about 50% of the tubules were fully occluded and a further about 40% were partially occluded (defined as having at least half of their cross sectional area blocked). Other solids loadings were also investigated. At 5 wt % and greater, a complete coating of particles formed on the dentine surface. In other words, the nHAp-containing mineral composition formed a natural smear layer as shown in FIG. 8.

Laser irradiation experiments were carried out on an extracted tooth with a coating of the HAp-containing mineral composition. In FIGS. 9a to 9d is shown the progression of surface modification leading to regional densification using a 430 mW, 135 fs and 83 MHz source at 800 nm. FIG. 9a is a low magnification scanning electron image showing three different carious regions where the structural modification has occurred on laser irradiation for 30 s, 60 s and 120 s.

FIGS. 9b, 9c and 9d are the corresponding high magnification images of the irradiated regions from which the contrast in surface densification with increasing irradiation time is apparent. The average pulsed power is sub watt (430 mW). The irradiated and photodensified area is 1.5 mm×1.5 mm. The illustrations in FIGS. 9a to 9d demonstrate that using a femtosecond pulsed laser, the energy density and delivery of power may be much more reliably managed than using longer pulsed laser sources (eg pico, nano and microsecond). Qualitative energy dispersive X-ray analysis showed that the composition of mineral phases was unchanged and the peak heights of elements were comparable with the material before laser irradiation.

Conclusions

Example 1 provides critical evidence on the potential for
(1) the use of compositions containing a rare-earth oxide activated nanoscale HAp for the treatment of hypersensitivity, dental caries and tooth wear;
(2) the use of a suspension of a HAp-containing powder for forming a protective layer over a carious and hypersensitive regions; and
(3) the use of ultra-short pulses in near-IR as a proof-of-principle for "filling without drilling".

Single-phase (by XRD) hydroxyapatite particles with a rod-like morphology were synthesized by a hydrothermal method. The potential for infiltrating the tubules in human dentine was assessed and compared with that of spherical nanosilica particles. For the synthesis, an increase from pH 5.1 to pH 12 of the starting suspension used in the hydrothermal reaction gave rise to a decrease in mean average particle length from about 360 nm to about 70 nm with a reduction in diameter from about 40 nm to about 30 nm. The change occurred between pH 8 and 10. TEM analysis showed the particles to be porous and/or display pitting of the surface with feature sizes about 3 nm. Treatment of etched sections of human dentine using particles with average length 70 nm and diameter 30 nm formed at pH12 showed the most promising tubule occlusion which was similar to that achieved using spherical nanosilica with up to 90% of the tubules being partially or fully occluded.

Proof-of principle trials using 800 nm femtosecond laser irradiation showed significant surface modification of the nHAp-containing layer in less than 3 minutes.

EXAMPLE 2

Controlling pH and Temperature

The synthesis of nHAp with rare-earth oxides as photoactivator focused on the following equilibrium which allows better control of pH for a given electrode potential (galvanic potential) for the desired chemical reaction.

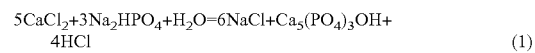

$$5CaCl_2 + 3Na_2HPO_4 + H_2O = 6NaCl + Ca_5(PO_4)_3OH + 4HCl \quad (1)$$

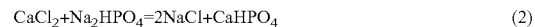

$$CaCl_2 + Na_2HPO_4 = 2NaCl + CaHPO_4 \quad (2)$$

The formation of hydroxyapatite occurs predominantly via reaction 1 in which the NaCl solution is removed from the precipitating hydroxyapatite phase by filtration. In considering the synthesis, the molar ratio of reactants must be controlled otherwise reaction 2 may lead to formation of calcium hydroxyl phosphate (CaHPO$_4$) phase from which the formation of hydroxyapatite via reaction 3 is very difficult.

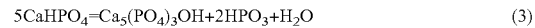

$$5CaHPO_4 = Ca_5(PO_4)_3OH + 2HPO_3 + H_2O \quad (3)$$

The incorporation of a photoactive lanthanide oxide in the HAp structure was carried out in the same manner as in reaction 1 by using a soluble chloride of the lanthanide. In this Example, the lanthanides Ho and Yb were tested.

Five moles of CaCl$_2$ in 125 ml of deionized water was dissolved at room temperature. Three moles of Na$_2$HPO$_4$ were dissolved in 125 ml of deionized water and the two solutions were slowly mixed using a magnetic stirrer. Lanthanide chloride (1-5 wt % of the weighed amounts of the 3 molar parts of Na$_2$HPO$_4$ and 5 molar parts of CaCl$_2$) was added into the solution. In FIG. 10, the shaded area indicates the preferred regime of pH control for close to ±0.1 volt. At higher pH there is a risk of the formation of Ca(OH)$_2$ which with prolonged CO$_2$ exposure will form CaCO$_3$ via bicarbonate. The lanthanide-containing solution was hydrothermally treated in a steel pressure vessel for times ranging from a few hours to a few days at a temperature between room temperature and 200° C. At low temperatures the growth of particles was slow and more rounded than at high temperatures (see FIGS. 11a to 11c). The needles (several micrometers) grown for longer than 12 hours at 200° C. are coarser than those grown at 80° C. for the same time. Average needles sizes were found to be less than 1 micrometer below 80° C. for a 12 hour experiment. Long and fat needles shown in FIGS. 11a-11c are less preferable than the finer more spherical needles. The nHAp-containing mineral composition shown in FIG. 11b is ideal for filling tubules and resurfacing enamel.

Figure 15:
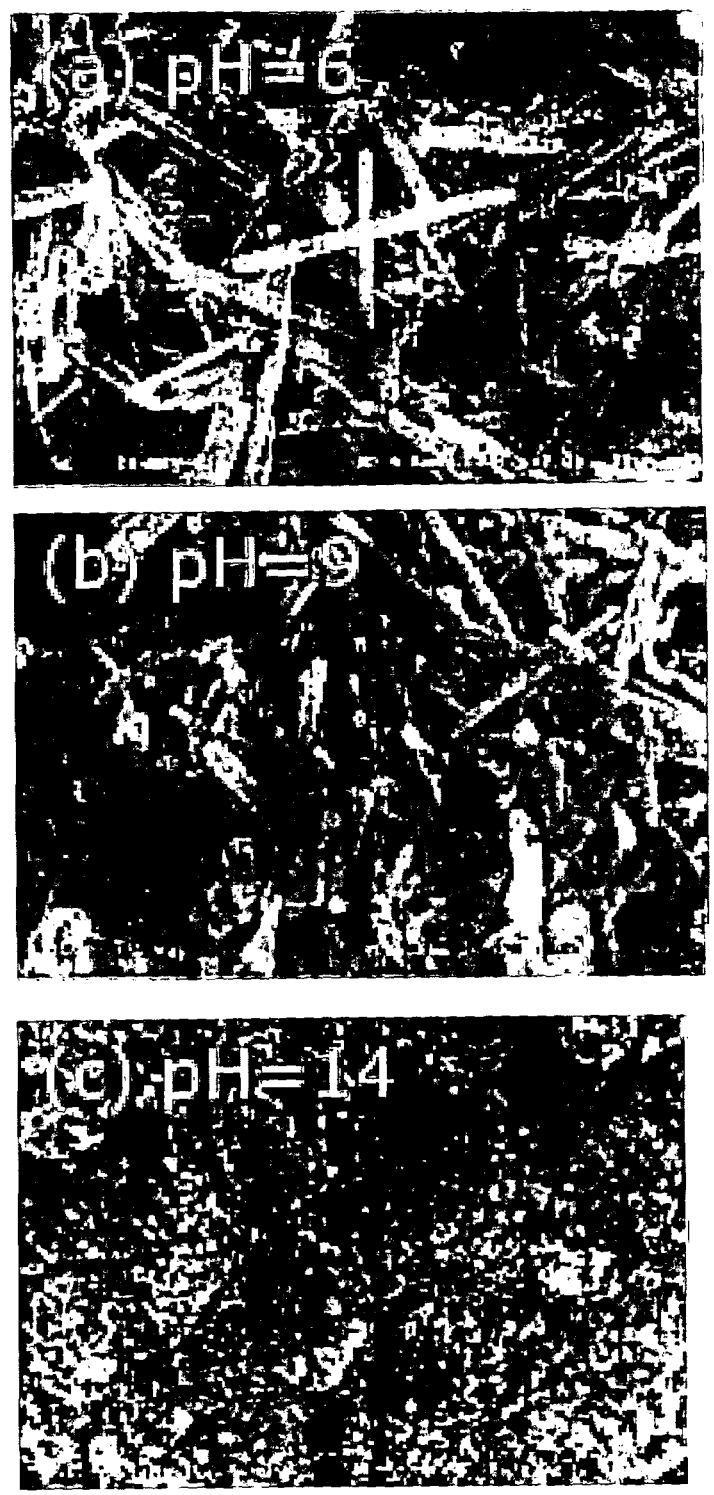

FIG. 15 illustrates SEM micrographs of photoactivated Ho-doped nano-size whiskers and crystals formed at 140° C. and pH 6, 9 and 14.

The sub-micrometer microstructure of HAp without photo-active lanthanide is shown in FIG. 12.

Lanthanide oxides incorporated in the structure were analyzed spectroscopically using Fourier transform infrared (FTIR) and fluorescence spectrometry. In FIG. 13, $Yb^{3+}$ ion absorption occurs at around 1000 $cm^{-1}$ with $OH^-$ first harmonic and fundamental bands at 1450 and 2900 $cm^{-1}$. A weak $Ho^{3+}$ band occurs at around 1400 $cm^{-1}$. FIG. 14 shows fluorescence of a nHAp-containing mineral composition excited with a 980 nm laser diode. The $Ho^{3+}$ electronic states emit at several wavelengths showing the effective absorption of photons and light emission. Emitted photons can be used for imaging the surface of laser treated enamel. $Ho^{3+}$ is also useful for laser absorption at longer wavelength (1900-2050 nm) for sintering.

EXAMPLE 3

(1) Experimental Procedures

Materials which were investigated included HAp-containing powders and HAp-containing powders doped with rare earth compounds (including ytterbium oxide $Yb_2O_3$, thulium oxide $Tm_2O_3$ and holmium oxide $Ho_2O_3$), calcium fluoride, aluminium phosphate and two or more of these compounds together. Reaction time, temperatures and pH values of the prepared solutions were investigated in the ranges 1 to 72 hrs, 25° C. to 300° C. and ~5.0 to 14 respectively. Various starting chemicals at different concentrations were part of the investigation as well as other synthetic treatments such as stirring, powder drying and calcination.

The properties of synthesized powder depend on parameters such as synthesis methodology, temperature and pH of the solutions, addition of chemical compounds, thermal treatments and washing/drying cycles. A hydrothermal method was adopted because of its ability to produce crystalline nHAp without the need for post heat treatment (see Riman R E, Suchanek W L, Byrappa K, Chen C W, Shuk P and Oakes C S. Solid State Ionics 151 393-402 (2002) In J S earl. *In Vitro Study of Dentin Tubule Infiltration by Hydroxyapatite and Silica Nanoparticles* (2007); and Liu J, Ye X, Wang H, Zhu M, Wang B, Yan H. *The influence of pH and temperature on the morphology of hydroxyapatite synthesized by hydrothermal method*. Ceramics International 29 629-633 (2003) In J S earl. In Vitro Study of Dentin Tubule Infiltration by Hydroxyapatite and Silica Nanoparticles (2008)). A chemical precipitation method was also adopted as part of the investigation to study the initial chemical reaction that occurs in the hydrothermal synthesis.

(2) Hydrothermal Synthesis

Hydrothermal synthesis involved preparing fresh 1M (80-250 ml) solutions of calcium nitrate tetrahydrate $(Ca(NO_3)_2.4H_2O)$ and diammonium hydrogen phosphate $((NH_4)_2HPO_4)$ in distilled water at pH ~6.5-7 and diluting the solutions to 0.1M. The solutions were mixed by the dropwise addition of the phosphate solution to the calcium solution to yield suspensions with a Ca/P molar ratio of 1.67 and stirred for 15-60 minutes at a speed of ~400 rpm. The pH of the mixed solutions was measured in the range 5.3-5.7 and adjusted to 8.0-14.0 by dropwise addition of concentrated (~17 M) ammonium hydroxide solution.

80 ml of the mixture was transferred to a 125 ml capacity Teflon-lined hydrothermal reactor. The hydrothermal reactor was placed in a furnace over a period of 6 to 72 hrs and at temperatures between 80° C. and 200° C. at 2° C./min heating rate and natural cooling. The suspension was then transferred to centrifugal tubes to be washed and decanted. This involved centrifugal sedimentation at a speed of 6000 rpm for 5 minutes followed by ultrasonic bathing for 5 minutes. This was repeated 6 times while the pH of the suspension was monitored. The final cycle was carried out using methanol to limit agglomeration of the particles. The wet sediment was re-suspended in methanol, collected, dried in an oven at 80° C. for a period of 2-24 hrs and weighed.

(3) Conditions of Synthesis

Reaction time effect—Hydrothermal reaction was investigated after 24 hrs, 48 hrs and 72 hrs at an initial pH of ~5.3-5.7 and a temperature of 80° C.

Temperature effect—Hydrothermal reaction was investigated at 120° C., 160° C. and 200° C. at an initial pH of ~5.3-5.7 for 24 hrs. Hydrothermal reaction was also investigated at 120° C. and 200° C. at an initial pH of ~5.3-5.7 for 72 hrs.

pH effect—Starting solutions were investigated at a pH of 5.6, 8, 9, 10 and 11 and a temperature of 200° C. for 24 hrs.

Precipitation time effect (aging)—Precipitation time before hydrothermal reaction was investigated after periods of 2 weeks, 4 weeks and 6 weeks at an initial pH of ~5.3-5.7 and a temperature of 200° C. for 24 hrs.

(4) Chemical Precipitation Synthesis

Chemical precipitation synthesis involved the same initial chemical reaction route used in the hydrothermal method. Fresh solutions at 1M (160-250 ml) were prepared and diluted to 0.1M and then mixed dropwise and stirred magnetically at a speed of ~400 rpm for 60 minutes. This produced a milky mixture which was left to stand in a fume cupboard at room temperature for 24 hrs in order to ensure optimum precipitation.

In experiment (A), the solution was divided into two suspensions. One suspension was transferred to centrifugal tubes to be washed and decanted. This involved centrifugal sedimentation at 6000 rpm for 5 minutes and ultrasonic bathing for 5 minutes. The cycles were repeated 6 times while the pH of the suspension was monitored until it reached 6.5-7. The final cycle was carried out using methanol to limit agglomeration of the particles. The wet sediment was collected and dried in an oven at 80° C. for 24 hrs and weighed. The second suspension was decanted physically by removing the solvent using a syringe. The wet precipitant was then dried in an oven at 80° C. for 24 hrs.

In experiment (B), the precipitant was decanted physically by removing the solvent (water) using a syringe and the wet precipitant was then dried in an oven at 80° C. for 24-36 hrs.

4.1 Doping Materials

The addition of elements via different compounds and concentrations under various conditions to substitute for calcium, phosphorous and hydroxide ions in HAp was part of the main objective of the investigation. The compounds which were investigated are listed in Table 7.

TABLE 7

| Rare earth oxides | Other compounds |
|---|---|
| Erbium oxide $Er_2O_3$, Thulium oxide $Tm_2O_3$ and Ytterbium oxide $Yb_2O_3$. | Aluminium phosphate $AlPO_4$ and calcium fluoride $CaF_2$. |

4.2 Preparation of Tooth Sections

Cross sections were prepared from clinically extracted human molars which were collected from the tissue bank in the Leeds Dental Institute after being gamma irradiated. Discs of ~2 mm thickness were cut from a region beneath the enamel dentin junction and the region above using a cutting machine equipped with a diamond string.

After sectioning, the tooth samples were polished by hand to remove any grinding marks using 2500 grit silicon carbide (SiC) paper in the presence of water for 2 minutes per side. After polishing, the sections were again washed with distilled water for 10 s per side and in an ultrasonic bath in distilled water for 1 minute. This was followed by etching with a 35% w/v phosphoric acid solution for 1 minute in a stirred bath to remove the natural smear layer and smear plugs. The sections were washed finally with distilled water in the ultrasonic bath for 1 minute.

The tooth samples were then dehydrated in alcohol/water mixtures containing 50%, 70%, 90% and 100% absolute ethanol for 30 minutes each in order to minimise any tissue shrinkage. Samples were left to dry in air and then under reduced pressure in a vacuum desiccator containing calcium sulphate desiccant for about 24 hrs at room temperature.

The resultant sections mimic the surface of naturally exposed dentin common to extreme cases of dentin hypersensitivity albeit with no fluid present within the tubules as would be the case in vivo (see Jose Renato Prietsch, Maria Antonieta Lopes De Souza, Aisha De Souza Gomes. Case report; *Unusual Dental Erosion Caused by a Cola Drink*. JCO-Online Copyright 2004-Vol 36: No 10: pages (549-552) 2002).

4.3 Tooth Section Coating and Dentinal Tubules Occlusion

Before coating, the powders were suspended in methanol as a liquid dispersion medium and each suspension was treated ultrasonically for 5 minutes. Tooth sections were either dip coated in 5% w/v suspensions for 20 seconds to 5 minutes or the same suspension was applied dropwise onto the tooth sections. After application, the samples were left to dry in air and then under reduced pressure in a desiccator for 24 hrs. Coating of tooth sections was carried out by dip coating and drop coating techniques.

Dip coating: Dipping was done manually by immersing the tooth sections in the 5 w/v % suspension for ~20 seconds for each dip. Dipping and withdrawal of all sections was carried out at a constant speed of ~1 mm per second.

Drop coating: This was carried out using a syringe to apply a drop or two onto the tooth sections on each side and the tooth section was then left to dry in air.

Initial coating was carried out as follows:
Section dipped once with HAp-$AlPO_4$
Section dipped once and drop coated with HAp-$AlPO_4$.$CaF_2$
Section dipped twice with HAp-$AlPO_4$.$Er_2O_3$
Section dipped once and drop coated with HAp-$AlPO_4$.$Er_2O_3$ With the exception of the section coated with HAp-$AlPO_4$, tooth sections were coated twice to provide a thicker and more uniform layer for laser treatment trials. This was due to the fact that it was difficult to determine the thickness and uniformity of the coatings.

A second coating was applied by a single dip in a 5% w/v HAp suspension but for a longer period of 5 minutes per section as follows:
Section dipped once with HAp only
Section dipped once with $AlPO_4$—$CaF_2$—$Er_2O_3$ doped HAp 4.4 Laser Treatment Laser experiments were carried out at the Institute for Materials Research (University of Leeds) and the Department of Physics and Astronomy (University of St. Andrews). Laser treatment trials were performed on synthesized powders as pellets and coated on tooth sections and on uncoated tooth sections using pulsed and continuous (CW) lasers at different beam powers.

CW and pulsed lasers were used on pellets. Tooth sections uncoated and coated with HAp-containing powders and doped HAp-containing powders were subjected to CW laser only. Pellets of ~2 mm thickness were prepared using a manual presser under a pressure of ~10 tons and then subjected to a pulsed laser with beam power of 1550 nm. The coated and uncoated tooth sections were subjected to a CW laser with a beam power of 980 nm as shown in Table 8 and 9.

TABLE 8

| Laser type | Wavelength | Exposure time |
|---|---|---|
| Pulsed laser | 1550 nm | 1 minutes |
| CW laser | 980 nm | 5 minutes |

TABLE 9

| Laser type | | Samples |
|---|---|---|
| Pulsed laser | Pellets | $Tm_2O_3$ doped HAp |
| | | $Er_2O_3$ doped HAp |
| | | $CaF_2$ doped HAp |
| CW laser | Pellets | $CaF_2$ doped HAp |
| | | $AlPO_4$—$CaF_2$—$Er_2O_3$ doped HAp |
| | Tooth sections | Section coated with HAp |
| | | Section coated with $AlPO_4$—$CaF_2$—$Er_2O_3$ doped HAp |

(5) Results

Characterization of the synthesized powders and suspensions involved the use of various thermoanalytic, electron and photo absorption spectroscopy techniques shown in Table 10. The morphology and the crystal structures of some synthesized undoped and doped HAp-containing powders are presented as SEM images and XRD graphs.

TABLE 10

| Spectroscopy | Type and Model | Conditions |
|---|---|---|
| TEM | Philips CM200 FEGTEM plus EDX | Very high resolution |
| SEM | LEO 1530 Gemini FEGSEM plus EDX and Philips XL30 | High resolution and low resolution respectively. |

TABLE 10-continued

| Spectroscopy | Type and Model | Conditions |
|---|---|---|
| Optical microscope | Nikon | AxioCam MRC5, objective magnifications 5, 10, 20, 40 (X10) |
| XRD | X'Pert MPD, Philips | CuKα(1.54 nm), Angles: 5°-90° |
| FTIR | VETEX 70, Bruker | Absorption at wavelength range NIR and MIR, 10000-800 $cm^{-1}$ |
| UV-Vis | Lambda 19, PerkinElmer | Absorption at wavelength range 300-1100 nm |
| DTA | DTA 7, PerkinElmer | From room temperature ~25 C.° up to ~1200 C.° at 5 C.°/min heating rate. |
| TGA | Designed at University of Leeds, IMR. | From room temperature ~25 C.° up to ~1200 C.° at 5 C.°/min heating rate. |

5.1 Hydrothermal Powders
 1. pH effect—FIGS. 16 to 20.
 2. Temperature and time effect—FIGS. 21 to 22.
 3. Ageing effect—FIGS. 23 to 25.
 4. Effect of pH 10—FIGS. 26 to 27.
 5. Aluminium phosphate—FIGS. 28 to 30. Table 11 shows the EDX semi quantitative measurement of a HAp-containing composition doped with 1 wt % aluminium phosphate hydrothermally treated at 80° C. for 10 hrs.

TABLE 11

| Element | Weight % | Atomic % |
|---|---|---|
| C K | 5.29 | 8.29 |
| O K | 57.57 | 67.77 |
| Al K | 16.37 | 11.42 |
| P K | 19.88 | 12.09 |
| Ca K | 0.89 | 0.42 |
| Totals | 100.00 | |

6. Thulium oxide—FIGS. 31 to 32.
5.2 Precipitated Powders
 1. HAp—FIGS. 33 to 34.
 2. Aluminium phosphate—FIGS. 35 to 36.
 3. Aluminium phosphate and calcium fluoride—FIGS. 37 to 38. Table 12 shows EDX semi quantitative measurement for 2 wt % aluminium phosphate and 2 wt % calcium fluoride doped HAp-containing powder prepared by the precipitation method at room temperature.

TABLE 12

| Element | Weight % | Atomic % |
|---|---|---|
| C K | 4.65 | 8.75 |
| O K | 25.66 | 36.26 |
| F K | 4.88 | 5.81 |
| Al K | 49.21 | 41.23 |
| P K | 4.42 | 3.22 |
| Ca K | 6.41 | 3.62 |
| Cu K | 2.34 | 0.83 |
| Pt M | 2.43 | 0.28 |
| Totals | 100.00 | |

4. Aluminum phosphate and thulium oxide—FIGS. 39 to 40. Table 13 shows the EDX semi quantitative measurement of 1 wt % aluminium phosphate and 2 wt % thulium oxide doped HAp-containing composition prepared by precipitation method at room temperature.

TABLE 13

| Element | Weight % | Atomic % |
|---|---|---|
| C K | 4.92 | 17.46 |
| O K | 21.06 | 56.06 |
| Al K | 3.30 | 5.22 |
| P K | 2.04 | 2.81 |
| Ca K | 1.29 | 1.38 |
| Ga K | 0.52 | 0.32 |
| Tm L | 63.97 | 16.13 |
| Pt M | 2.89 | 0.63 |
| Totals | 100.00 | |

5. Aluminum phosphate and erbium oxide—FIGS. 41 to 43. Table 14 shows the EDX semi quantitative measurement of 2 wt % aluminium phosphate and 2 wt % erbium oxide doped HAp-containing composition prepared by precipitation method at room temperature.

TABLE 14

| Element | Weight % | Atomic % |
|---|---|---|
| C K | 8.01 | 15.96 |
| O K | 16.91 | 25.29 |
| Al K | 58.39 | 51.77 |
| P K | 4.46 | 3.45 |
| Ca K | 2.32 | 1.39 |
| Cu K | 3.26 | 1.23 |
| Er L | 4.87 | 0.70 |
| Pt M | 1.76 | 0.22 |
| Totals | 100.00 | |

6. Aluminium phosphate, erbium oxide and calcium fluoride—FIGS. 44 to 45.

(6) Coatings, Dentinal Tubules Occlusion and Laser Effects

Powders for coating tooth sections and laser treatment trials were synthesized by the chemical precipitation process. The powders were modified during synthesis by the addition of aluminum phosphate, erbium oxide and calcium fluoride in order to produce photoactive materials.

The effectiveness of dip coating (single dipping) of dentinal tubules by undoped and doped powders was investigated using optical microscopy, SEM and ESEM imaging. The optical microscope images of HAp-AlPO$_4$ were unclear (see FIG. 46). However the image of 100× magnification revealed an apparent blur which could be due to the diffuse elastic light scattering from the coating.

6.1 Coatings

Although SEM provides much better images and quality than ESEM, the latter was used to confirm the presence of particles on tooth sections which were needed for laser treatment trials. SEM and ESEM images of coatings containing HAp, AlPO$_4$—CaF$_2$—Er$_2$O$_3$ doped HAp and AlPO$_4$ doped HAp are shown in FIGS. 47 to 49.

6.2 Dentinal Tubules Occlusion

The SEM images in FIGS. 47 to 49 show platelets occluding or covering (rather than infiltrating) many dentinal tubules. This could be more useful in terms of laser sintering to achieve uniform melting of particles along the dentine surface and therefore seal the tubules.

6.3 Laser Effects

Initial laser treatments were carried out using pulsed and CW lasers on different samples as shown in Table 15. Samples were ~2 mm pellets and tooth sections uncoated and coated with different HAp-containing powders synthesized by the chemical precipitation method. Powders contained undoped HAp and $AlPO_4$—$CaF_2$—$Er_2O_3$ doped HAp.

The pulsed laser at 1550 nm was used only on ~2 mm pellets containing thulium oxide, erbium oxide and calcium fluoride doped HAp for about 1 minute. However the laser only interacted with a pellet containing thulium doped HAp resulting in what looked like a melting effect as shown in FIG. 50.

Even though a pulsed laser provides more energy than a CW laser, the latter was used on pellets (thickness 2 mm) and tooth sections uncoated and coated with HAp-containing powders as shown in FIGS. 51 to 55. This was conducted in the presence of a thermocouple (being in contact with the backside of the sample) and a temperature reader in order to measure the temperature change as the laser was applied. The temperature changes are shown in Table 15.

TABLE 15

| Sample | Initial temperature T1 | Second temperature T2 | ΔT |
|---|---|---|---|
| Pellets | | | |
| $CaF_2$ doped HAp | 21° C. | 25° C. | 4° C. |
| $AlPO_4$—$CaF_2$—$Er_2O_3$ doped HAp | 20.8° C. | 26° C. | 5.2° C. |
| Tooth sections | | | |
| Tooth section only | 22.8° C. | 26° C. | 3.2° C. |
| Section coated with HAp only | 22.8° C. | 24.9° C. | 2.1° C. |
| Section coated with $AlPO_4$—$CaF_2$—$Er_2O_3$ doped HAp | 22.8° C. | 23.2° C. | 0.4° C. |

The temperature differential in these measurements appears remarkably small in each case and is well below the cell necrosis temperature of 41° C.

6.4 Microhardness

A microhardness test was carried out on different tooth sections (see Table 16). All of the sections were laser treated and included those as-prepared and those coated as follows:
  Tooth section uncoated and CW lasered
  Tooth section coated with undoped HAp-containing composition and CW lasered
  Tooth section coated with $AlPO_4$—$CaF_2$—$Er_2O_3$ doped HAp-containing composition and CW lasered A microhardness test was performed using a computer-controlled Duramin Indenter Machine (Struers A/S, DK 26-10, Ballerup, Denmark). Measurements presented in Table 16 were taken after two indentations per section with a Knoop diamond under a 25 g load for 30 seconds. The indents were measured in microns by image analysis software.

TABLE 16

| Sample | Indent Size/μm | KH | Average | MPa |
|---|---|---|---|---|
| Tooth section | 126.4 | 22.3 | 24.55 | 240.7533 |
| | 115.3 | 26.8 | | |
| Tooth section + HAp only | 71 | 70.5 | 69.5 | 681.5622 |
| | 76 | 68.5 | | |
| Tooth section + Doped HAp | 56.6 | 110.9 | 112.65 | 1104.719 |
| | 55.8 | 114.4 | | |

The combination of reduced $OH^-$ ions and increased fluoride content of the minerals progressively increases the hardness from 240 MPa on the dentinal tubule surface to 1100 MPa in the fluoride coated tooth section.

6.5 OH Content in the Mineral

The presence of $CaF_2$ reduces the hydroxide content in the mineral composition. This becomes apparent when the mineral composition is heated in air. The water vapours released correlate directly with the water of crystallization present in the mineral composition. FIG. 56 shows the rates of % weight loss versus temperature for the mineral compositions listed in the inset. The composition containing HAp without dopant has the highest amount of weight loss above 500° C. which progressively decreases with dopant concentrations ($AlPO_4$, $Er_2O_3$, and $CaF_2$). $AlPO_4$ and $Er_2O_3$ reduce the $OH^-$ ions in the mineral structure by increasing the number of $PO_4^{3-}$ bonds rather than $HPO_4^{2-}$ bonds. The presence of $F^-$ in the form of $CaF_2$ further reduces $OH^-$ bonds by replacing them in the crystalline lattice. This replacement occurs because $F^-$ has the largest electronegativity and therefore attracts $H^+$ and cations more readily than $OH^{2-}$ ions.

(7) Conclusions

The effect of room temperature precipitation of HAp-containing powders on morphological characteristics was compared with powders formed at high-temperature. The particles formed at room temperature are flat and have a large surface area (see FIGS. 33, 35, 37, 39, 41 and 44) in contrast to the needle shape fibres formed at elevated temperature (see FIGS. 16, 21, 23 and 27).

The characteristic differences in the two types of powder arise due to the difference in temperature and the presence of $AlPO_4$ and rare earth oxides. A flat shape is more desirable than a needle shape since it is a better morphology to achieve large surface coverage over hypersensitive and worn teeth. Surface coverage using the room temperature precipitated HAp-containing composition is shown in FIG. 46 (5 mm×5 mm area) and in occluded dental tubules in FIGS. 47 to 49 after a single dip coating. The thickness of the coating may be less than 10 micrometers and may be enhanced by multiple dip coating.

Larger surface area coverage also allows rapid heat dissipation which becomes evident in FIGS. 50 to 55. For heat dissipation and laser sintering, a CW laser at 980 nm was used over different periods for 2 mm thick pellets. The influence of laser induced heating and melting is shown in FIGS. 50 to 55. In FIG. 50 the pellet contains thulium oxide ($Tm_2O_3$) as a photoactive dopant which does not absorb laser light at 980 nm. As a result, little evidence of structural change is apparent when compared with FIG. 44. Loose flakes are apparent on the surface. By contrast, when erbium oxide ($Er_2O_3$) is incorporated in the flakes (see FIG. 51) the sintering and incipient fusion commence readily when irradiated with a CW 980 nm laser. This is because at 980 nm $Er_2O_3$ has much larger absorption than the apparently negligible absorption in $Tm_2O_3$. In the presence of $CaF_2$ (see FIG. 52) the rate of melting increases.

FIGS. 53 to 55 show laser heating, sintering and resultant change in the morphology of dentinal tubule surface. When a 980 nm laser was irradiated on the dentinal tubule surface, there was no change in the structure after prolonged exposure of 5 minutes. In FIG. 54 in the top row, the surface coverage of dentinal tubules with flakes of HAp+$AlPO_4$+$Er_2O_3$ composition is compared with the surface of a 2 mm thick pellet. In the bottom row in FIG. 54, the effect of melting and sintering is compared from which it is seen that the peripheral edge of dentinal tubules is covered with melted flakes. The contrast in the solidified materials on the surface dentinal tubule is greater when comparing the morphologies in FIGS. 54 and 55. In FIG. 55 the HAp-containing composition also contains $CaF_2$. As a result of rapid melting, the rosetted crystals grow and spread to invade the uncovered regions of dentinal tubules. This points towards the fact that adhesion between the underlying natural enamel and the synthetic material may be occurring.

EXAMPLE 4

Powder Synthesis 320 ml of 0.1 molar solutions of calcium nitrate tetrahydrate $Ca(NO_3)_2.4H_2O$ and di-ammonium hydrogen phosphate $(NH_4)_2HPO_4$ (Fisher Scientific) were prepared in distilled water at room temperature. The di-ammonium hydrogen solution was added drop-by-drop into the calcium nitrate tetra-hydrate solution and mixed by stirring to yield a suspension with a Ca/P molar ratio of 1.67.

$Er_2O_3$, $AlPO_4$ and $CaF_2$ (Fisher Scientific) were incorporated in the suspension in powder form at concentrations of 22.3 wt %, 5.5 wt % and 3.7 wt % respectively. The slurry was then stirred for 1 hour at a speed of ~400 rpm to produce a milky mixture which was left to stand at room temperature for 24 hours. This was covered to minimize the absorption of atmospheric $CO_2$. Finally the wet precipitate was collected and dried in an oven at 80° C. for 24 hours.

Preparation of In Vitro Dentine Cross Sections

Tooth sections prepared to mimic the naturally exposed dentine surface characteristic of extreme cases of sensitivity are shown in FIGS. 57a and 57b. The tooth sections were prepared from clinically extracted human premolars/molars which were collected from the tissue bank at the Leeds Dental Institute after being sterilized by γ-ray irradiation. Discs of ~1-2 mm in thickness were cut from a region beneath the enamel-dentine junction using a diamond cutting machine (Well Precision Vertical Diamond Wire Saw, Model 3242). After sectioning, tooth sections were polished by hand using 2500 grit silicon carbide (SiC) paper in the presence of water for 2 minutes on each side. This was followed by washing with distilled water for 20 seconds and then inside an ultrasonic bath with distilled water for 1 minute. The sections were then etched with a 35% w/v phosphoric acid solution for 1 minute in a stirred bath to remove the natural smear layer and smear plugs. This was followed by washing with distilled water in an ultrasonic bath for 1 minute. Finally the sections were dehydrated in alcohol/water mixtures containing 50%, 70%, 90% and 100% absolute ethanol for 30 minutes each in order to minimize any tissue shrinkage by absolute alcohol. The sections were then left to dry in air and then dried by reduced pressure in a vacuum desiccator containing calcium sulphate as desiccant for 24 hours. Dentine sections were characterized by SEM to determine the microscopic structures and Ca:P ratio.

Coating of In Vitro Dentine Cross Sections

Tooth cross sections were coated with undoped and doped CaP mineral compositions and the sections are shown in FIGS. 58a and 58b respectively. The coating process involved the preparation of a 5% w/v suspension of the powder in ethanol as a liquid dispersion medium and treatment ultrasonically for 5 minutes. The dip coating was carried out for between 20 and 300 seconds keeping the dipping and withdrawal of all sections at a constant speed. The suspension with 5% w/v powder was also applied dropwise using a syringe onto the tooth sections (1 drop on each side). After application, the sections were left to dry in air and then dried under reduced pressure in a desiccator for 24 hours. The coating thickness was estimated to be larger than 30 μm. This was estimated from the regions unaffected by the laser radiation during which the pulsed laser spot was fixed (shown in FIGS. 63a and 63b described below).

In Vitro Laser Irradiation Treatments

Laser irradiation and sintering experiments were carried out with two wavelength bands around 980 nm and 1500 nm. In these regions, $Er_2O_3$ has strong absorption bands due to its electronic structure. By employing two different laser sources the resulting structural changes in the mineral compositions were investigated using SEM. Using a 980 nm CW source with an average output power of 160 mW, the coated tooth sections and CaP pellets were irradiated for up to 5 minutes. The femtosecond laser was operated at a centre wavelength of 1520 nm with a pulse duration of 100 fs, repetition rate of 2.5 GHz and an average output power of 130 mW. The laser output parameters correspond to a pulse energy of 52 pJ/pulse and a peak power of 520 W. For measuring the temperature change during irradiation, a chromel-alumel thermocouple was attached to the back of the sections.

Results and Discussion

The synthesized powders and treated tooth sections were characterized using X-ray powder diffraction, scanning electron microscopy and thermal gravimetric analysis. This included the determination of temperature change during laser irradiation and the micro-hardness of the sintered surface. The analysis used a range of techniques necessary for determining the post-laser sintering phase and the resulting morphological changes which may help in improving the occluded surface for acid and wear resistance and hardness.

XRD analyses were performed using monochromatic CuKα 0.1542 nm radiation (X'Pert MPD, Philips). XRD patterns of undoped and doped CaP mineral compositions showed the formation of monetite phases (di-CaP phase) as well as the presence of undissolved dopant crystalline phases ($Er_2O_3$, $AlPO_4$ and $CaF_2$) which is confirmed in FIG. 59. The presence of undissolved crystalline dopants might have been due to the room temperature synthesis at which supersaturation with respect to $Er_2O_3$, aluminium phosphate and $CaF_2$ might exist. The thermodynamic equilibrium limits for mineral phase precipitation and the lack of dissolution of dopants during the synthesis of CaP mineral compositions at room temperature have not been fully characterised. The XRD patterns of undoped CaP mineral compositions show a pure monetite phase which is in good agreement with the JCPDS card number 01-070-1425, whilst $Er_2O_3.AlPO_4.CaF_2$ doped CaP mineral compositions showed the presence of monetite and brushite, together with HAp and undissolved dopant phases ($Er_2O_3$, $AlPO_4$ and $CaF_2$).

The addition of $AlPO_4$ resulted in a monetite-$AlPO_4$ phase mixture with reduced intensities of the monetite peaks while the addition of $CaF_2$ to the monetite-$AlPO_4$ mixture resulted in the formation of brushite confirmed by its major peak at 2θ=11.6° along with the $CaF_2$ phase (not shown). By comparison, the major peak for HAp is at 2θ=31.7°. In the presence of all three dopants, the major peaks for monetite were at 2θ values at 26.5°, 30.1° and 32.5° which preferentially decreased compared with the minor peaks at 2θ values at 36°, 40°, 43°, 50°, 53°, 70°, 79°, 81.5° and 87.6° the intensities of which increased significantly. In comparison with the standard JCPDS data, the dopants may have contributed to a significant change in the disproportionate amounts of HAp, brushite and monetite and the intensity changes may also reflect in the platelet-like structures of the mineral composition.

Energy dispersive analysis for determining the elemental distribution in the phases present in undoped and doped CaP mineral compositions and natural dentine were carried out using SEM and are compared in Table 17. From the ratio Ca:P the mineral phases for doped and undoped CaP were determined. For the undoped CaP composition, the CaP phase was found to be octacalcium phosphate (OCP) $Ca_8H_2(PO_4)_6 \cdot 5H_2O$ with a Ca:P ratio of 1.32 [Y. X. Pang and X. Bao, "*Influence of temperature, ripening time and calcination on the morphology and crystallinity of hydroxyapatite Nanoparticles*", J European Ceramic Society, vol. 23, pp. 1697-1704, 2003; and L. C. Palmer, C. J. Newcomb, S. R. Kaltz, E. D. Spoerke and S. I. Stupp, "*Biomimetic systems for hydroxyapatite mineralization inspired by Bone and Enamel*". Chem. Rev, vol. 108, no. 11, pp. 4754-4783, 2008]. In the case of the doped CaP mineral composition, the CaP phase is predominantly dicalcium phosphate dihydrate (DCPD) (brushite) $CaHPO_4 \cdot 2H_2O$ with a Ca:P ratio of 1.0. The doped mineral composition showed a ratio of (Ca.Al.Er):(P) of 1.78 which is comparable with the value of 1.67 cation-anion ratio in fluorinated HAp and 1.77 in HAp with carbonates.

irradiation at 980 nm for 5 minutes was examined using SEM. It was found that due to the high density of pellets compared with a CaP mineral layer over the exposed dentine tubules, the melting process did not commence even after 5 minutes of irradiation with 980 nm laser with a 0.5 mm spot size. By contrast, when both undoped and doped CaP mineral compositions were irradiated with the 980 nm laser for 5 minutes, significant changes occurred suggesting that heat accumulation in the doped mineral composition layer was much higher than that in the doped CaP pellets. The resulting microstructures of 980 nm CW laser induced melting are compared in FIGS. 61a to 61d. Little morphological change was observed after 1 minute of laser irradiation. In FIGS. 61a and 61b, the melting behaviour of undoped CaP pellets is shown with pockets of fragmented droplets showing little continuum of surface. By contrast, the doped CaP dentine surface when irradiated with 980 nm CW laser for 5 minutes showed a continuum of melted surface (left region in FIG. 61c) on the right of a fragmented region which might have coalesced due to the presence of $CaF_2$, $AlPO_4$ and $Er_2O_3$. On further examination at a higher magnification in SEM, the solidification front is evidenced with a rosette like crystal growth in FIG. 61d which might be related to the formation of complex fluoride phosphate based crystals.

By comparing the results from the irradiation of doped CaP with the CW 980 nm and 1520 nm femtosecond pulsed

TABLE 17

EDX- weight % elements in undoped and doped CaP powders and dentine

| | Weight % of elements | | | | | | | W % Ratio | |
|---|---|---|---|---|---|---|---|---|---|
| Sample | Ca | P | O | C | Al | Er | F | Ca:P | Ca.Al.Er:P |
| CaP- only | 22.4 | 16.9 | 56.4 | 4.4 | — | — | — | 1.32 | — |
| CaP-$AlPO_4 \cdot Er_2O_3 \cdot CaF_2$ | 13 | 12.4 | 41.9 | 4.6 | 4.4 | 4.7 | 16.3 | 1.04 | 1.78 |
| Dentine | 19.6 | 11.1 | 44.2 | 23.9 | — | — | — | 1.77 | — |

FIGS. 60a and 60b show a platelet-like morphology of undoped and doped CaP particles prepared by the chemical precipitation method at room temperature. Platelet-like particles of doped CaP seem to be crystalline compared with those of undoped CaP. The particles were of different sizes with average dimensions of 10-15 μm but submicrometer thickness. The distribution of particulate area was 5 μm² to 150 μm². It has been reported that spherical or rounded particles were excellent in infiltrating dentinal tubules [J. S. Earl, S. J. Milne, and D. J. Wood, "*In Vitro Study of dentin tubule infiltration by hydroxyapatite and Silica Nanoparticles*", pp 1-16, 2008; N. S. Resende, M. Nele and V. M. M. Salim, "*Effects of anion substitution on the acid properties of hydroxyapatite*", Thermochimica Acta, vol. 451, no. 1-2, pp. 16-21, 2006; and E. Boanini, M. Gazzano and A. Bigi, "*Ionic substitutions in calcium phosphates synthesized at low temperature*", Acta Biomaterialia, vol. 6, pp. 1882-1894, 2010]. However the platelet-like particles shown in FIGS. 60a and 60b seem to be superior as these particles may be capable of providing larger surface occlusion, rapid heat transfer and large sintering area during laser irradiation treatments.

Laser Irradiation Results

The effects of irradiation using a CW laser at 980 nm and a femtosecond pulsed laser at 1520 nm on the CaP particles in the form of pellets and coatings on dentine sections were characterized by SEM and are shown in FIGS. 61 to 63. The effect of 980 nm CW laser irradiation on CaP particles was studied by pressing pellets of <2 mm in thickness which were then irradiated for 1 to 5 minutes. The effect of laser lasers, the morphological and chemical changes in the structures were characterised in detail by analysing the localized melting, sintering and phase change. Radiation absorption is through the presence in the doped CaP mineral composition of $Er^{3+}$ ions which have a maximum absorption in the range 1480-1530 nm.

The doped CaP mineral composition coated tooth sections were irradiated with the 1520 nm pulsed laser for time periods varying from 30 seconds to 5 minutes and the corresponding SEM micrographs are shown in FIGS. 62a to 62d. In these figures, different types of microstructural features emerge when compared with the micrographs in FIGS. 61a to 61d.

Initially the irradiation periods between 30 seconds to 300 seconds were investigated and irradiation times longer than 120 seconds appeared to be unsuitable for future application because of the beam damage of the sintered area. The damage occurs due to the high power density confined over a small cross-section of 500 μm because of the lack of laser beam rastering across the whole coated surface. The micron bar in FIGS. 62a to 62d corresponds to a 200 μm scale. FIGS. 62a and 62b are the low and high magnification areas of a CaP coated surface which was irradiated for 120 seconds. It is apparent from FIG. 62b that the central spot of the focussed beam which shows a hole and an arc shaped crack is of the order of 500 μm. On the left hand side of this figure there is a much smoother region than that which is on the right hand side of the arced crack. Unlike in FIGS. 61a to 61d, a continuum of dense region except cracks is seen which has arisen due to over exposure of a coated region.

However when the doped CaP coating was irradiated for only 30 seconds as compared with FIGS. 62c and 62d, the post irradiation coating was quite uniform with a ridge-like feature around the centre of the spot size represented by the white circle in FIG. 62c. The densified regions in FIGS. 62c and 62d exhibit a much improved surface than those shown in FIGS. 62a and 62b which were obtained after 120 seconds of irradiation. The occluded region in the micrographs 62a-62d appears to extend over several hundreds of micrometers giving an opportunity for more detailed clinical investigation in terms of long term erosion and acid resistance of the laser sintered CaP mineral compositions.

Further investigations were carried out by preparing the cross-sections of the coated and occluded region to determine the efficacy of the pulsed laser sintering techniques. FIGS. 63a and 63b show a comparative microstructural investigation on interfacial adherence of undoped and doped CaP mineral compositions. From the comparison, it can be concluded that the densification of doped and undoped CaP mineral compositions using pulsed laser does not follow melting and solidification as observed in FIGS. 61a to 61d. In FIGS. 63a and 63b, there is clear evidence of the formation of a two-layer structure, the first layer of which is an approximately 10 μm thick occluded region which seems to be dense and continuous. FIG. 63a with undoped CaP mineral composition has more defects than the coating occluded with the doped CaP mineral composition shown in FIG. 63b. The second layer over the occluded 10 μm layer is a partially dense overlayer which appears to extend across the micrograph with brighter undissolved $Er_2O_3$ particles.

Measurements of the Temperature During 980 nm CW Laser Irradiation

The temperature change during irradiation by the 980 nm CW laser was measured using a chromel-alumel thermocouple with an electronic temperature reader attached to the back of the tooth section. The measured data are given in Table 18 for uncoated and coated sections. The effect of heat localization in doped CaP mineral compositions over the tooth section is apparent which is why the temperature differential is much smaller than in the tooth sections which were either uncoated or coated with undoped CaP mineral compositions. The localization of thermal load in doped CaP mineral compositions confirms that the presence of dopants ($Er_2O_3$, $AlPO_4$ and $CaF_2$) increases the uniformity of fusion which means that the heat generated due to laser irradiation is not wasted in raising the temperature of the surrounding tissue leading to heat loss. The analysis of heat loss is quite critical because any surgical procedure using laser irradiation must be safe for clinical trials and it must not cause healthy tissue damage and cell necrosis which occurs irreversibly above 40° C.

TABLE 18

Temperature change $\Delta T = (T_1 - T_2)$ measured during 980 nm CW laser irradiation for 5 minutes on uncoated and coated tooth sections.

| Sample | Temperature change ($\Delta T$) measured during 980 nm CW laser irradiation for 5 minutes | | |
|---|---|---|---|
| | Initial temperature $T_1$ | Final temperature $T_2$ | $T_1 - T_2$ |
| Tooth section uncoated | 22.8° C. | 26° C. | 3.2° C. |
| Tooth section coated with CaP— only | 22.8° C. | 24.9° C. | 2.1° C. |
| Tooth section coated with CaP—$Er_2O_3$•$AlPO_4$•$CaF_2$ | 22.8° C. | 23.2° C. | 0.4° C. |

Micro-Hardness Measurements

Micro-hardness measurements on a laser sintered surface were carried out on uncoated tooth sections and tooth sections coated with undoped and doped CaP mineral composition using a computer-controlled indenter (Struers A/S, DK 26-10, Ballerup, Denmark). The surface hardness was measured under applied forces of ≤1 kgf (ASTM standards) for 10 to 15 seconds. The indents were measured in micrometers by using image analysis software and the data are compared in Table 19. The measurements indicate that the laser irradiated tooth section coated with doped CaP mineral composition had the highest hardness number (1100 MPa) which is almost twice that of a laser irradiated tooth section coated with undoped CaP mineral composition (680 MPa) and four times that of a dentine surface (240 MPa). By comparison, it should be noted that natural enamel has a hardness of 3500 MPa.

TABLE 19

Micro-hardness measurements after 980 nm CW laser irradiation treatment

| Sample | Indent Size/μm | KH | Average | MPa |
|---|---|---|---|---|
| Tooth section uncoated | 126.4 | 22.3 | 24.55 | 240 |
| | 115.3 | 26.8 | | |
| Tooth section coated with CaP only | 71 | 70.5 | 69.5 | 680 |
| | 76 | 68.5 | | |
| Tooth section coated with CaP—$Er_2O_3$•$AlPO_4$•$CaF_2$ | 56.6 | 110.9 | 112.65 | 1100 |
| | 55.8 | 114.4 | | |

Residual $OH^-$ Ion Analysis for CaP Mineral Compositions

Figure 64:
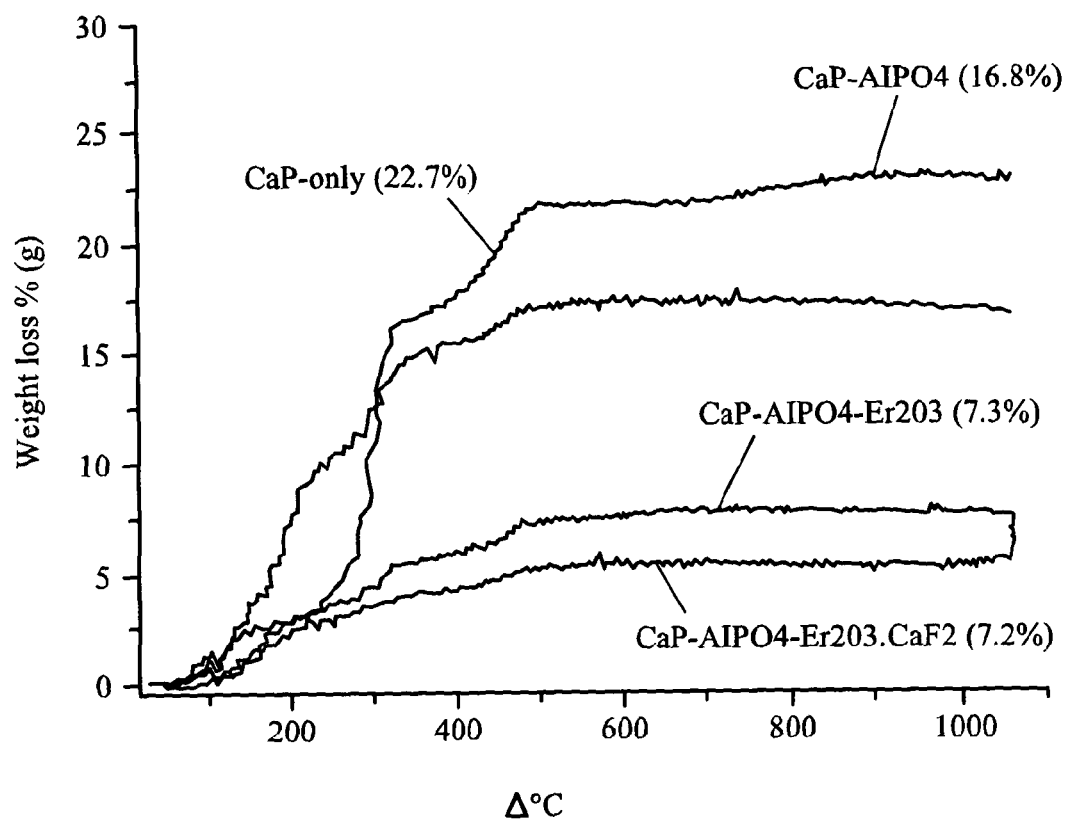

Residual $OH^-$ ions and any free water present in the doped and undoped CaP mineral compositions were analyzed using the thermogravimetric (TG) technique by heating the mineral composition from room temperature to 1100° C. at a rate of 5° C./min to determine the rate of change in weight relative to the change in temperature. FIG. 64 shows the percentage weight loss and reveals that the doped CaP mineral composition has the lowest percentage weight loss in comparison with undoped CaP mineral composition. This indicates that the overall $OH^-$ concentrations have significantly reduced. In the figure legend, the data in small parentheses represent the corresponding overall weight loss. The TG data implies that the presence of fluoride ions may have helped in releasing the OH and free water because HAp and related calcium phosphate phases have a range of complex $OH^-$ ions in their crystalline structure. The presence of fluorides in the mineral structure blocks the pathway for anion exchange between $OH^-$ and bicarbonates.

CONCLUSIONS

Rare-earth oxide and aluminium phosphate doping increases the photo activation and acid resistance of calcium phosphate mineral compositions. The dopants modify the morphology of the calcium phosphate mineral composition at room temperature from the classic needle shape in hydroxyapatite to a flaky morphology which enhances dental tubule occlusion as shown in FIG. 60. The trivalent ions increase the formation of monetite whereas the addition of $CaF_2$ increases the phase volume fraction of brushite (see FIG. 59). The presence of aluminium phosphate, rare-earth oxide and $CaF_2$ in the structure of calcium phosphate reduces the overall OH ions and water of crystallisation (determined by the thermogravimetric analysis shown in FIG. 64) and therefore decreases the propensity for carbonate and bicarbonate formation.

The laser irradiation of an occluded surface using a 980 nm CW source demonstrates that the temperature rise in dentinal tubule structure varies between less than 1° to 4° C. for doped and undoped materials as shown in Table 18. This suggests that the maximum temperature on the surface never exceeds 26 to 27° C. The limited number of systematic analyses in Table 19 on micro-hardness measurements shows that the surface hardness increases from 240 MPa to 1.1 GPa on the doped calcium phosphate surface.

The microstructural analysis of the interface and irradiated surfaces in FIGS. 60 and 61 reveal that with the CW irradiation melting occurs and the surface coverage in the undoped mineral composition due to non-uniform absorption of radiation is poorer than in the doped mineral composition. By contrast, the pulsed laser irradiated surface yields a much more continuous interface between the dentinal tubules and the top enamel layer. The occlusion of tubules with doped mineral composition is much better than is exhibited by a mineral composition without doping (see FIG. 63). The mechanism of sintering of CaP mineral composition with high repetition rate pulsed laser shown in FIGS. 63a-63d does not appear to involve localized heat generation as observed during melting shown in FIG. 61a-61d.

The invention claimed is:

1. A photosensitive composition, comprising:
   i. synthetic nanocrystalline hydroxyapatite doped with each of (a) a rare earth ion, (b) an aluminum ion, and (c) a fluoride ion;
   ii. monetite; and
   iii. brushite.

2. The photosensitive composition as claimed in claim 1, wherein the rare earth ion exhibits absorption bands which substantially match or overlap one or more absorption bands of the synthetic nanocrystalline hydroxyapatite.

3. The photosensitive composition as claimed in claim 1, wherein the rare earth ion is an erbium, ytterbium, holmium or thulium ion.

4. An aqueous, ketonic or alcoholic dispersion of a photosensitive composition as claimed in claim 1.

5. The photosensitive composition as defined in claim 1 for use in restorative or cosmetic dentistry.

6. A solid form of the photosensitive composition as defined in claim 1.

7. A process for preparing a photosensitive composition comprising:
   (a) preparing an aqueous mixture of calcium, phosphate, fluoride, aluminum, and rare earth ions at a pH in the range 5 to 14;
   (b) mixing the aqueous mixture to form photosensitive composition comprising:
      i. synthetic nanocrystalline hydroxyapatite doped with each of (a) the rare earth ion (b) the aluminum ion, and (c) the fluoride ions;
      ii. monetite; and
      iii. brushite;
   (c) isolating the photosensitive composition.

8. A cosmetic method for whitening or veneering a tooth of a human or non-human animal subject comprising:
   (1) applying an amount of a photosensitive composition as defined in claim 1 to a surface of the tooth other than a dentinal surface; and
   (2) irradiating the amount of the photosensitive composition with laser irradiation so as to promote densification.

9. A method for generating an image of an exposed dentinal surface of a tooth of a human or non-human animal subject comprising:
   (A) administering an amount of a photosensitive composition as defined in claim 1 to the exposed dentinal surface;
   (B) irradiating the photosensitive composition or physiologically tolerable formulation thereof with irradiation;
   (C) capturing the radiation emitted by the photosensitive composition or physiologically tolerable formulation thereof; and
   (D) generating from the radiation emitted by the photosensitive composition or physiologically tolerable formulation thereof an image of the exposed dentinal surface.

* * * * *